United States Patent
Li et al.

(10) Patent No.: US 10,576,453 B2
(45) Date of Patent: *Mar. 3, 2020

(54) MEMBRANE FABRICATION METHODS USING ORGANOSILICA MATERIALS AND USES THEREOF

(71) Applicant: ExxonMobil Research and Engineering Company, Annandale, NJ (US)

(72) Inventors: Quanchang Li, Dayton, NJ (US); Dhaval Ajit Bhandari, East Brunswick, NJ (US); Benjamin A. McCool, Annandale, NJ (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 265 days.

This patent is subject to a terminal disclaimer.

(21) Appl. No.: 14/966,445

(22) Filed: Dec. 11, 2015

(65) Prior Publication Data
US 2016/0168485 A1 Jun. 16, 2016

Related U.S. Application Data

(60) Provisional application No. 62/091,071, filed on Dec. 12, 2014, provisional application No. 62/091,077, filed on Dec. 12, 2014.

(51) Int. Cl.
*B01D 69/10* (2006.01)
*B01D 71/70* (2006.01)
(Continued)

(52) U.S. Cl.
CPC ............ *B01J 20/262* (2013.01); *B01D 15/00* (2013.01); *B01D 53/02* (2013.01); *B01D 53/047* (2013.01);
(Continued)

(58) Field of Classification Search
CPC ............ B01D 67/0039; B01D 67/0079; B01D 67/0069; B01D 67/0088; B01D 67/0083;
(Continued)

(56) References Cited

U.S. PATENT DOCUMENTS 3,178,392 A 4/1965 Kriner
4,218,308 A 8/1980 Itoh et al.
(Continued)

FOREIGN PATENT DOCUMENTS

CN 101804335 A 8/2010
CN 101980013 A 2/2011
(Continued)

OTHER PUBLICATIONS

Matheron et al. Stabilization of well-organized transient micellar phases in CTAB-templated silica and organosilica thin films. Soft Matter, 2007, 3, 223-229. (Year: 2007).*

(Continued)

*Primary Examiner* — Katherine Zalasky McDonald
(74) *Attorney, Agent, or Firm* — Andrew T. Ward; Priya G. Prasad

(57) ABSTRACT

Methods for fabricating a membrane with an organosilica material which is a polymer comprising independent units of Formula $[Z^3Z^4SiCH_2]_3$ (I), wherein each $Z^3$ represents a hydroxyl group, a $C_1$-$C_4$ alkoxy group or an oxygen atom bonded to a silicon atom of another unit or an active site on the support and each $Z^4$ represents a hydroxyl group, a $C_1$-$C_4$ alkoxy group, a $C_1$-$C_4$ alkyl group, an oxygen atom bonded to a silicon atom of another unit or an active site on the support are provided. Methods of removing a contaminant from a hydrocarbon stream are also provided.

34 Claims, 8 Drawing Sheets

(51) Int. Cl.

| | | |
|---|---|---|
| *B01J 20/26* | (2006.01) | |
| *B01J 20/10* | (2006.01) | |
| *B01J 20/32* | (2006.01) | |
| *B01D 53/02* | (2006.01) | |
| *C10G 45/00* | (2006.01) | |
| *C10G 31/09* | (2006.01) | |
| *B01J 20/02* | (2006.01) | |
| *B01J 20/18* | (2006.01) | |
| *B01J 20/28* | (2006.01) | |
| *C10G 25/00* | (2006.01) | |
| *B01J 20/08* | (2006.01) | |
| *C01B 37/00* | (2006.01) | |
| *C10G 45/44* | (2006.01) | |
| *B01J 20/286* | (2006.01) | |
| *C10G 45/04* | (2006.01) | |
| *C10G 50/00* | (2006.01) | |
| *C10G 45/64* | (2006.01) | |
| *C08G 77/60* | (2006.01) | |
| *B01J 20/06* | (2006.01) | |
| *C10G 47/02* | (2006.01) | |
| *B01D 15/00* | (2006.01) | |
| *C10G 35/06* | (2006.01) | |
| *C10G 45/34* | (2006.01) | |
| *B01J 20/30* | (2006.01) | |
| *C10G 45/46* | (2006.01) | |
| *C10K 1/32* | (2006.01) | |
| *C10G 45/60* | (2006.01) | |
| *B01J 23/42* | (2006.01) | |
| *B01D 53/22* | (2006.01) | |
| *B01J 31/12* | (2006.01) | |
| *B01J 37/03* | (2006.01) | |
| *C07F 7/08* | (2006.01) | |
| *B01D 53/04* | (2006.01) | |
| *B01D 53/047* | (2006.01) | |
| *B01D 67/00* | (2006.01) | |
| *B01J 20/16* | (2006.01) | |
| *B01J 20/22* | (2006.01) | |
| *B01J 23/44* | (2006.01) | |
| *B01J 31/02* | (2006.01) | |
| *B01J 35/10* | (2006.01) | |
| *B01J 37/02* | (2006.01) | |
| *C08G 77/26* | (2006.01) | |
| *C10G 45/52* | (2006.01) | |
| *C10M 101/02* | (2006.01) | |
| *C23C 16/56* | (2006.01) | |

(52) U.S. Cl.
CPC ....... *B01D 53/0462* (2013.01); *B01D 53/228* (2013.01); *B01D 67/0088* (2013.01); *B01D 69/10* (2013.01); *B01D 71/70* (2013.01); *B01J 20/0229* (2013.01); *B01J 20/0237* (2013.01); *B01J 20/06* (2013.01); *B01J 20/08* (2013.01); *B01J 20/10* (2013.01); *B01J 20/103* (2013.01); *B01J 20/16* (2013.01); *B01J 20/18* (2013.01); *B01J 20/22* (2013.01); *B01J 20/264* (2013.01); *B01J 20/286* (2013.01); *B01J 20/28011* (2013.01); *B01J 20/28057* (2013.01); *B01J 20/28061* (2013.01); *B01J 20/28064* (2013.01); *B01J 20/28066* (2013.01); *B01J 20/28069* (2013.01); *B01J 20/28071* (2013.01); *B01J 20/28073* (2013.01); *B01J 20/28076* (2013.01); *B01J 20/28078* (2013.01); *B01J 20/28083* (2013.01); *B01J 20/3042* (2013.01); *B01J 20/3204* (2013.01); *B01J 20/3212* (2013.01); *B01J 20/3236* (2013.01); *B01J 20/3238* (2013.01); *B01J 20/3272* (2013.01); *B01J 23/42* (2013.01); *B01J 23/44* (2013.01); *B01J 31/0274* (2013.01); *B01J 31/125* (2013.01); *B01J 31/127* (2013.01); *B01J 35/1019* (2013.01); *B01J 35/1023* (2013.01); *B01J 35/1028* (2013.01); *B01J 35/1061* (2013.01); *B01J 37/0213* (2013.01); *B01J 37/0236* (2013.01); *B01J 37/036* (2013.01); *C01B 37/00* (2013.01); *C07F 7/081* (2013.01); *C07F 7/0807* (2013.01); *C07F 7/0818* (2013.01); *C08G 77/26* (2013.01); *C08G 77/60* (2013.01); *C10G 25/003* (2013.01); *C10G 31/09* (2013.01); *C10G 35/06* (2013.01); *C10G 45/00* (2013.01); *C10G 45/04* (2013.01); *C10G 45/34* (2013.01); *C10G 45/44* (2013.01); *C10G 45/46* (2013.01); *C10G 45/52* (2013.01); *C10G 45/60* (2013.01); *C10G 45/64* (2013.01); *C10G 47/02* (2013.01); *C10G 50/00* (2013.01); *C10K 1/32* (2013.01); *C10M 101/02* (2013.01); *C23C 16/56* (2013.01); *B01D 2253/20* (2013.01); *B01D 2253/25* (2013.01); *B01D 2256/245* (2013.01); *B01D 2257/302* (2013.01); *B01D 2257/304* (2013.01); *B01D 2257/40* (2013.01); *B01D 2257/504* (2013.01); *B01D 2257/80* (2013.01); *B01J 2220/86* (2013.01); *B01J 2231/641* (2013.01); *B01J 2231/646* (2013.01)

(58) Field of Classification Search
CPC .... B01D 69/10; B01D 71/70; B01D 2323/14; B01D 2323/48; B01D 53/04; B01D 53/0462; B01J 20/262; B01J 20/10; B01J 20/32; B01J 20/3202; B01J 20/3297; B01J 20/3231; B01J 20/3234
See application file for complete search history.

(56) References Cited

U.S. PATENT DOCUMENTS

| | | | |
|---|---|---|---|
| 5,365,003 A | 11/1994 | Chang et al. | |
| 5,630,937 A | 5/1997 | Betz et al. | |
| 5,719,322 A | 2/1998 | Lansbarkis et al. | |
| 5,858,457 A * | 1/1999 | Brinker | B01D 67/0048 427/162 |
| 7,300,905 B2 | 11/2007 | Keefer et al. | |
| 7,497,965 B2 | 3/2009 | Wariishi et al. | |
| 7,538,065 B2 | 5/2009 | McCarthy et al. | |
| 7,682,502 B2 | 3/2010 | McCarthy et al. | |
| 7,705,062 B2 | 4/2010 | Markowitz et al. | |
| 7,754,330 B2 | 7/2010 | Hamada et al. | |
| 7,767,620 B2 | 8/2010 | Whitnall et al. | |
| 7,947,799 B2 | 5/2011 | Landskron et al. | |
| 8,110,692 B2 | 2/2012 | Bellussi et al. | |
| 8,211,498 B2 | 7/2012 | Ku et al. | |
| 8,277,600 B2 | 10/2012 | Hamada et al. | |
| 8,277,661 B2 | 10/2012 | Sah et al. | |
| 8,425,762 B2 | 4/2013 | McCarthy et al. | |
| 8,441,006 B2 | 5/2013 | Mchalak et al. | |
| 8,470,074 B2 | 6/2013 | Baugh et al. | |
| 8,545,694 B2 | 10/2013 | McCarthy et al. | |
| 8,562,856 B2 | 10/2013 | Giannantonio et al. | |
| 8,568,520 B2 | 10/2013 | Ohashi et al. | |
| 8,598,070 B1 | 12/2013 | Baugh et al. | |
| 8,598,071 B1 | 12/2013 | Baugh et al. | |
| 8,809,561 B2 | 8/2014 | Bellussi et al. | |
| 9,181,282 B2 | 11/2015 | Ide et al. | |
| 2003/0188991 A1 | 10/2003 | Shan et al. | |
| 2005/0093189 A1 | 5/2005 | Vo | |
| 2006/0058565 A1 | 3/2006 | DeWild | |

(56) References Cited

U.S. PATENT DOCUMENTS

| | | |
|---|---|---|
| 2006/0070917 A1 | 4/2006 | McCarthy et al. |
| 2006/0165574 A1 | 7/2006 | Sayari |
| 2007/0034992 A1 | 2/2007 | Wariishi et al. |
| 2007/0054136 A1 | 3/2007 | Takahashi et al. |
| 2007/0112242 A1* | 5/2007 | Edmiston ............... C02F 1/28 588/249 |
| 2007/0173401 A1 | 7/2007 | Landskron et al. |
| 2009/0071334 A1* | 3/2009 | Ryu ...................... B01D 53/228 95/117 |
| 2009/0130412 A1 | 5/2009 | Hatton et al. |
| 2009/0215612 A1 | 8/2009 | McCarthy et al. |
| 2009/0294922 A1 | 12/2009 | Hamada et al. |
| 2010/0155302 A1 | 6/2010 | Kaminsky et al. |
| 2010/0233482 A1 | 9/2010 | Hamada et al. |
| 2011/0139685 A1 | 6/2011 | McCarthy et al. |
| 2011/0190115 A1 | 8/2011 | Ciriminna et al. |
| 2012/0059181 A1 | 3/2012 | Bellussi et al. |
| 2012/0160742 A1 | 6/2012 | Sohn et al. |
| 2013/0075876 A1 | 3/2013 | Goethals et al. |
| 2013/0078172 A1 | 3/2013 | Li et al. |
| 2013/0249049 A1 | 9/2013 | Michalak et al. |
| 2014/0004358 A1 | 1/2014 | Blackwell et al. |
| 2014/0186246 A1 | 7/2014 | Calabro et al. |
| 2014/0208753 A1 | 7/2014 | Liu et al. |
| 2015/0011787 A1 | 1/2015 | Bellussi et al. |
| 2016/0167015 A1 | 6/2016 | Podsiadlo et al. |
| 2016/0167016 A1 | 6/2016 | Li et al. |
| 2016/0167032 A1 | 6/2016 | Podsiadlo et al. |
| 2016/0168171 A1 | 6/2016 | Li et al. |
| 2016/0168172 A1 | 6/2016 | Li et al. |
| 2016/0168173 A1 | 6/2016 | Li et al. |
| 2016/0168174 A1 | 6/2016 | Li et al. |
| 2016/0168333 A1 | 6/2016 | Podsiadlo et al. |
| 2016/0168484 A1 | 6/2016 | Weigel et al. |
| 2016/0229959 A1 | 8/2016 | Li et al. |
| 2017/0306068 A1 | 10/2017 | Holtcamp et al. |
| 2017/0313791 A1 | 11/2017 | Mertens et al. |
| 2017/0320971 A1 | 11/2017 | Holtcamp et al. |
| 2017/0320977 A1 | 11/2017 | Holtcamp et al. |
| 2017/0327604 A1 | 11/2017 | Holtcamp et al. |
| 2017/0354961 A1 | 12/2017 | Podsiadlo et al. |
| 2017/0355822 A1 | 12/2017 | Calabro et al. |
| 2017/0355823 A1 | 12/2017 | Peterson et al. |
| 2018/0142066 A1 | 5/2018 | Falkowski et al. |

FOREIGN PATENT DOCUMENTS

| | | |
|---|---|---|
| CN | 102052713 A | 5/2011 |
| CN | 102643429 A | 8/2012 |
| CN | 103157362 A | 6/2013 |
| CN | 103495340 A | 1/2014 |
| CN | 103613975 A | 3/2014 |
| CN | 104117343 A | 10/2014 |
| EP | 1995214 A2 | 11/2008 |
| JP | H10151343 A | 6/1998 |
| JP | H11295284 A | 10/1999 |
| JP | 2003167233 A | 6/2003 |
| JP | 2006083311 A | 3/2006 |
| JP | 2006095512 A | 4/2006 |
| JP | 2007070520 A | 3/2007 |
| JP | 2007238761 A | 9/2007 |
| JP | 2008045060 A | 2/2008 |
| JP | 2008062138 A | 3/2008 |
| JP | 2010100492 A | 5/2010 |
| JP | 2011025201 A | 2/2011 |
| JP | 2012149138 A | 8/2012 |
| JP | 2014057941 A | 4/2014 |
| JP | 5544672 B1 | 7/2014 |
| RU | 2291878 C1 | 1/2007 |
| WO | 9610537 A1 | 4/1996 |
| WO | 2006032140 A1 | 3/2006 |
| WO | 2007081212 A1 | 7/2007 |
| WO | 2011145933 A1 | 11/2011 |
| WO | 2013093022 A1 | 6/2013 |
| WO | 2014010512 A1 | 1/2014 |
| WO | 2014090757 A1 | 6/2014 |

OTHER PUBLICATIONS

Cagnol et al. Humidity-controlled mesostructuration in CTAB-templated silica thin film processing. The existence of a modulable steady state. J. Mater. Chem., 2003, 13, 61-66. (Year: 2003).*

Grosso et al. Fundamentals of mesostructing through evaporation-induced self-assembly. Adv. Funct. Mater. 2004, 14, No. 4, 309-322. (Year: 2004).*

Wang et al. Pore-size Tuning of Highly Selective Organic-norganic Hybrid Silica Membranes by Solid-phase Post-treatment at Low Temperature. Chem. Lett. 2012, 41, 1663-1665 (Year: 2012).*

Agirre et al. Hybrid organosilica membranes and processes: Status and outlook. Separation and Purification Technology 121 (2014, published online Aug. 8, 2013) 2-12. (Year: 2013).*

Wu et al. Properties of sol±gel derived scratch-resistant nano-porous silica films by a mixed atmosphere treatment. Journal of Non-Crystalline Solids 275 (2000) 169-174. (Year: 2000).*

Liu et al. Simple Surfactant-Free Route to Mesoporous Organic-Inorganic Hybrid Silicas Containing Covalently Bound Cyclodextrins. J. Org. Chem. 2004, 69, 2213-2216. (Year: 2004).*

Chemtob et al. Macroporous organosilica films via a template-free photoinduced sol-gel process. J. Mater. Chem., 2010, 20, 9104-9112. (Year: 2010).*

Canck, Els De. Versatile Hybrid Nanomaterials: Periodic Mesoporous Organosilicas as adsorbent and catalyst. Dissertation, Ghent University (2013) 1-245. Available online Dec. 3, 2013. (Year: 2013).*

Hatton et al. Spin-coated periodic mesoporous organosilica thin films—Towards a new generation of low-dielectric-constant materials. Adv. Funct. Mater. (2005) 15, No. 5, May, 823-829. (Year: 2005).*

Castricum et al. Tailoring the separation behavior of hybrid organosilica membranes by adjusting the structure of the organic bridging group. Adv. Funct. Mater. (2011) 21, 2319-2329. (Year: 2011).*

Topchiev et al., "Preparation of hexa alkoxy derivatives of cyclotrimethylenesilane", Doklady Akademii Nauk SSSR, 1955, pp. 95-96. vol. 103.

Kriner, "The preparation of cyclic siliconmethylene compounds", Journal of Organic Chemistry, Jun. 1964, pp. 1601-1606, vol. 29.

Kuivila et al., "Trimethylsilyl-substituted norbornenes, norbornanes, and nortricyclene", Journal of Organic Chemistry, Oct. 1964, pp. 2845-2851, vol. 29.

Vidal-Madjar et al., "Fast Analysis of Geometrical Isomers of Complex Compounds by Gas-Solid Chromatography", Gas Chromatography, Sep. 28, 1970-Oct. 2, 1970, pp. 381-386.

Niemeyer et al., "Effects of $CO_2$ Sorption on the Rotational Reorientation Dynamics of a Model Solute Dissolved in Molten Poly(dimethylsiloxane)", Macromolecules, Jan. 13, 1998, pp. 77-85, vol. 31.

Shinji et al., "Novel Mesoporous Materials with a Uniform Distribution of Organic Groups and Inorganic Oxide in Their Frameworks", Journal of the American Chemical Society, Oct. 4, 1999, pp. 9611-9614, vol. 121.

Melde et al., "Mesoporous Sieves with Unified Hybrid Inorganic/Organic Frameworks", Chemistry of Materials, Oct. 9, 1999, pp. 3302-3308, vol. 11.

Eliseeva et al., "Antifoaming additive for alkaline absorption solutions for removal of carbon dioxide from synthesis gas", Khimicheskaya Promyshlennost, 1999, pp. 632-633, vol. 10.

Brondani, et al., "Polyfunctional carbosilanes and organosilicon compounds. Synthesis via Grignard reactions", Tetrahedron Letters, Mar. 2, 2001, pp. 2111-2114, vol. 34.

Gilman et al., "Reactions of triphenylsilyllithium with some dichloropropenes", Journal of Organometallic Chemistry, Apr. 13, 2001, pp. 293-303, vol. 2.

Landskron et al., "Periodic Mesoporous Organosilicas Containing Interconnected [Si(CH2)]3 Rings", Science, Oct. 10, 2003, pp. 266-269, vol. 302.

(56) References Cited

OTHER PUBLICATIONS

Harlick et al., "Applications of Pore-Expanded Mesoporous Silica. 5. Triamine Grafted Material with Exceptional CO2 Dynamic and Equilibrium Adsorption Performance", Industrial & Engineering Chemistry Research, Dec. 20, 2006, pp. 446-458 vol. 46.
Grudzien et al., "Cage-like ordered mesoporous organosilicas with isocyanurate bridging groups: Synthesis, template removal and structural properties", Microporous and Mesoporous Materials, pp. 68-77, vol. 118, No. 1-3.
Walcarius et al., "Mesoporous organosilica adsorbents: nanoengineered materials for removal of organic and inorganic pollutants", Journal of Materials Chemistry, Jan. 1, 2010, pp. 4478-4511, vol. 20, No. 22.
Vidal et al., "Adsorption of polycyclic aromatic hydrocarbons from aqueous solutions by modified periodic mesoporous organosilica", Journal of Colloid and Interface Science, Feb. 3, 2011, pp. 466-473, vol. 357, No. 2.
Goethals et al., "Ultra-low-k cyclic carbon-bridged PMO films with a high chemical resistance", Journal of Materials Chemistry, Feb. 21, 2012, pp. 8281-8286, vol. 22.
PCT/US2015/065258 Partial International Search Report and Written Opinion dated Mar. 16, 2016.
PCT/US2015/065194 International Search Report and Written Opinion dated Mar. 29, 2016.
PCT/US2015/065191 International Search Report and Written Opinion dated Mar. 29, 2016.
PCT/US2015/065306 International Search Report and Written Opinion dated Mar. 29, 2016.
PCT/US2015/065219 International Search Report and Written Opinion dated Apr. 5, 2016.
PCT/US2015/065283 International Search Report and Written Opinion dated Apr. 6, 2016.
PCT/US2015/065199 International Search Report and Written Opinion dated Apr. 8, 2016.
PCT/US2015/065204 International Search Report and Written Opinion dated Apr. 8, 2016.
PCT/US2015/065225 International Search Report and Written Opinion dated Apr. 8, 2016.
Grudzien et al., "Cage-like mesoporous organosilicas with isocyanurate bridging groups synthesized by soft templating with poly(ethylene oxide)-poly(butylene oxide)-poly(ethylene oxide) block copolymer", Journal of Colloid and Interface Science, May 1, 2009, pp. 354-362, vol. 333, No. 1, Elsevier.
Grudzien et al., "Periodic Mesoporous Organosilicas with Im3m Symmetry and Large Isocyanurate Bridging Groups", The Journal of Physical Chemistry B, Feb. 1, 2006, pp. 2972-2975, vol. 110, No. 7, ACS Publications.
Olkhovyk et al., "Periodic Mesoporous Organosilica with Large Heterocyclic Bridging Groups", Journal of American Chemical Society, Jan. 1, 2005, pp. 60-61, vol. 127, No. 1, ACS Publications.
Poli et al., "Different Routes for Preparing Mesoporous Organosilicas Containing the Troger's Base and Their Textural and Catalytic Implications", The Journal of Physical Chemistry C, Apr. 21, 2011, pp. 7573-7585, vol. 115, No. 15, ACS Publications.
PCT/US2015/065208 International Search Report and Written Opinion dated May 17, 2016.
PCT/US2015/065200 Partial International Search Report and Written Opinion dated May 23, 2016.
Diaz et al., "Hybrid organic-inorganic catalytic porous materials synthesized at neutral pH in absence of structural directing agents", Journal of Materials Chemistry, Jan. 1, 2009, pp. 5970-5979, vol. 19, No. 33, Royal Society of Chemistry.
Reale et al., "A fluoride-catalyzed sol-gel route to catalytically active non-ordered mesoporous silica materials in the absence of surfactants", Journal of Materials Chemistry, Jan. 1, 2005, pp. 1742-1754, vol. 15, No. 17, Royal Society of Chemistry.
PCT/US2015/065200 Partial International Search Report and Written Opinion dated Jul. 18, 2016.
Goethals, et al., "A new procedure to seal the pores of mesoporous low-k films with precondensed organosilica oligomers", Chemical Communications, 2012, pp. 2797-2799, vol. 48, No. 22, Royal Society of Chemistry.
Goethals et al., "Sealed ultra low-k organosilica films with improved electrical, mechanical and chemical properties", Journal of Materials Chemistry C, 2013, vol. 1, No. 25, Royal Society of Chemistry.
Goethals et al., "Hydrophobic high quality ring PMOs with an extremely high stability", Journal of Materials Chemistry, 2010, pp. 1709-1716, vol. 20, No. 9, Royal Society of Chemistry.
Landskron et al., "Periodic Mesoporous Organosilicas: Self-Assembly from Bridged Cyclic Silsesquioxane Precursors", Angewandte Chemie, International Edition, 2005, pp. 2107-2109, vol. 44, No. 14, Wiley-VCH Verlag GmbH & Co. KgaA.

\* cited by examiner

Effect of MO concentration in coating solution on coating quality (L to R: 5.1 wt.%, 5.4 wt.%, 5.6 wt.% PMO)

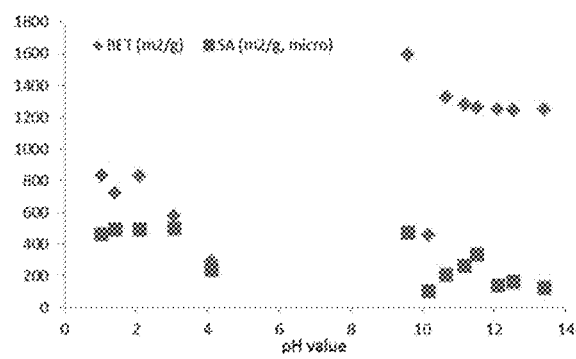 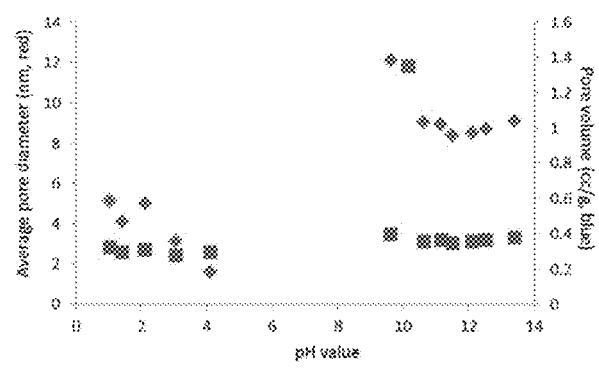
Fig. 4a                     Fig. 4b

MEMBRANE FABRICATION METHODS USING ORGANOSILICA MATERIALS AND USES THEREOF

CROSS-REFERENCE TO RELATED APPLICATIONS

This application claims priority to U.S. Provisional Application Ser. No. 62/091,071 filed Dec. 12, 2014 and U.S. Provisional Application Ser. No. 62/091,077 filed Dec. 12, 2014, which are herein incorporated by reference in their entirety.

This application is also related to several other co-pending U.S. applications, filed on even date herewith and bearing U.S. patent application Ser. Nos. 14/965,992 (entitled "Organosilica Materials and Uses Thereof"), Ser. No. 14/966,001 (entitled "Methods of Producing Organosilica Materials and Uses Thereof"), Ser. No. 14/966,071 (entitled "Aromatic Hydrogenation Catalysts and Uses Thereof"), Ser. No. 14/965,984 (entitled "Organosilica Materials and Uses Thereof"), (entitled "Organosilica Materials and Uses Thereof"), Ser. No. 14/966,383 (entitled "Organosilica Materials and Uses Thereof"), Ser. No. 14/966,284 (entitled "Organosilica Materials and Uses Thereof"), Ser. No. 14/966,407 (entitled "Coating Method Using Organosilica Materials and Uses Thereof"), Ser. No. 14/966,534 (entitled "Adsorbent for Heteroatom Species Removal and Uses Thereof"), and Ser. No. 14/966,790 (entitled "Method for Separating Aromatic Compounds from Lube Basestocks"), the entire disclosures of each of which are incorporated by reference herein.

Additionally, this application is further related to several other co-pending U.S. applications, filed on even date herewith and bearing Ser. No. 15/526,512 (entitled "Organosilica Materials for Use as Adsorbents for Oxygenate Removal"), Ser. No. 15/526,524 (entitled "Supported Catalyst for Olefin Polymerization"), Ser. No. 15/526,529 (entitled "Supported Catalyst for Olefin Polymerization"), Ser. No. 15/526,513 (entitled "Supported Catalyst for Olefin Polymerization"), and Ser. No. 15/526,521 (entitled "Supported Catalyst for Olfin Polymerization"), the entire disclosures of each of which are incorporated by reference herein.

FIELD OF THE INVENTION

The present invention relates to methods of fabricating membranes using organosilica materials and processes for liquid separation.

BACKGROUND OF THE INVENTION

Membranes have various potential industrial applications including gas, water and hydrocarbon separations. However, to be more competitive with other separation processes, such as distillation, adsorption and cryogenic separations, membranes have to demonstrate economical scalability and stability in harsh chemical, thermal and mechanical environments. While membranes exist for natural gas and water desalination applications, there is a lack of suitable membranes for hydrocarbon and crude oil separations (e.g., liquid separations) due to challenges such as low flux, poor economics and fouling potential of the membranes. For example, performance of polymeric membranes, such as polytetrafluoroethylene (PTFE) and polyimides, is limited by low flux and low operating temperatures. Furthermore, such polymers are prone to plasticize (i.e., swell) upon exposure to aromatic/naphthenic liquids at high-pressure, thereby making them unselective. Carbon molecular sieve membranes, offer much higher selectivity and the materials do not plasticize when compared to conventional polymeric membranes for separations; however, carbon molecular sieve membranes can suffer from scalability challenges and low permeability due to sub-structure collapse during pyrolysis. Sintered metals provide chemical, thermal and mechanical robustness, but cost of manufacturing such membranes remains prohibitively high.

Further, microporous and mesoporous silica materials have challenges with hydrothermal stability, and require a surfactant-templated route which is cost and energy intensive. Conventional ceramic membranes ($TiO_2$, $Al_2O_3$) have been proposed for these challenging applications since they provide stability and selectivity, however to fabricate membranes of small pore sizes (2-10 nm) require multiple intermediate layers which reduce their flux (productivity) and the fabricated membranes have a low surface area/volume. Also, surface defects on the ceramic membranes cause low selectivity for separation work, and limit their applications. Thus, it remains highly desirable to develop a membrane with chemical, thermal and mechanical robustness with high rejection (selectivity), flux (productivity), tunable surface properties while still being economically scalable.

Therefore, there is a need for improved methods of fabricating improved membranes using organosilica materials that can be prepared by a method that can be practiced in the absence of a structure directing agent, a porogen or surfactant.

SUMMARY OF THE INVENTION

It has been found that membranes with chemical, thermal and mechanical robustness with high rejection (selectivity), flux (productivity) and tunable surface properties can be successfully fabricated using organosilica materials without the need for a structure directing agent, a porogen or surfactant.

Thus, in one aspect, embodiments of the invention provide a method method for fabricating a membrane, the method comprising: adding at least one compound of Formula $[Z^1Z^2SiCH_2]_3$ (Ia) into an aqueous mixture that contains essentially no structure directing agent or porogen to form a solution, wherein each $Z^1$ represents a hydroxyl group, a $C_1$-$C_4$ alkoxy group or an oxygen bonded to a silicon atom of another compound and each $Z^2$ represents, a hydroxyl group, a $C_1$-$C_4$ alkoxy group, a $C_1$-$C_4$ alkyl group or an oxygen bonded to a silicon atom of another compound; coating the solution onto a support to form a coated support; aging the coated support; and drying the coated support to obtain a membrane comprising an organosilica material which is a polymer comprising independent units of Formula $[Z^3Z^4SiCH_2]_3$ (I), wherein each $Z^3$ represents a hydroxyl group, a $C_1$-$C_4$ alkoxy group or an oxygen atom bonded to a silicon atom of another unit or an active site on the support and each $Z^4$ represents a hydroxyl group, a $C_1$-$C_4$ alkoxy group, a $C_1$-$C_4$ alkyl group, an oxygen atom bonded to a silicon atom of another unit or an active site on the support.

In still another aspect, embodiments of the invention provide a membrane made according to the methods described herein.

In still another aspect, embodiments of the invention provide a method of removing microcarbon residue from a crude oil, the method comprising filtering a crude oil through a membrane made according to the method of claim 1.

Other embodiments, including particular aspects of the embodiments summarized above, will be evident from the detailed description that follows.

BRIEF DESCRIPTION OF THE DRAWINGS

FIG. 4a illustrates BET surface area and microporous surface area for samples made with varying pHs.

FIG. 4b illustrates pore volume and average pore radius for samples made with varying pHs.

DETAILED DESCRIPTION OF THE INVENTION

Figure 1:
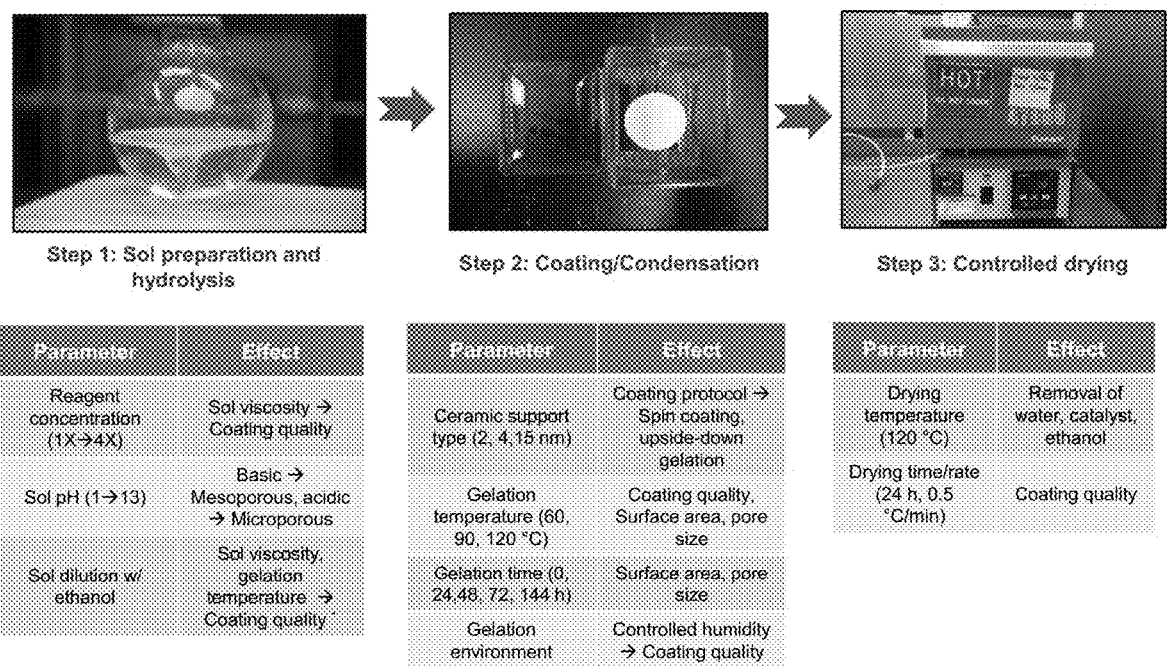
FIG. 1 illustrates the procedure for preparing mesoporous organosilica (MO) membranes and the effects of different parameters on the membranes.

In various aspects of the invention, methods for coating a support, organosilica material-coated supports and gas and separation processes using the organosilica material-coated supports are provided.

I. Definitions

For purposes of this invention and the claims hereto, the numbering scheme for the Periodic Table Groups is according to the IUPAC Periodic Table of Elements.

The term "and/or" as used in a phrase such as "A and/or B" herein is intended to include "A and B", "A or B", "A", and "B".

The terms "substituent", "radical", "group", and "moiety" may be used interchangeably.

As used herein, and unless otherwise specified, the term "$C_n$" means hydrocarbon(s) having n carbon atom(s) per molecule, wherein n is a positive integer.

As used herein, and unless otherwise specified, the term "hydrocarbon" means a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different values of n.

As used herein, and unless otherwise specified, the term "alkyl" refers to a saturated hydrocarbon radical having from 1 to 12 carbon atoms (i.e. $C_1$-$C_{12}$ alkyl), particularly from 1 to 8 carbon atoms (i. e. $C_1$-$C_8$ alkyl), particularly from 1 to 6 carbon atoms (i.e. $C_1$-$C_6$ alkyl), and particularly from 1 to 4 carbon atoms (i.e. $C_1$-$C_4$ alkyl). Examples of alkyl groups include, but are not limited to, methyl, ethyl, propyl, butyl, pentyl, hexyl, heptyl, octyl, decyl, and so forth. The alkyl group may be linear, branched or cyclic. "Alkyl" is intended to embrace all structural isomeric forms of an alkyl group. For example, as used herein, propyl encompasses both n-propyl and isopropyl; butyl encompasses n-butyl, sec-butyl, isobutyl and tert-butyl and so forth. As used herein, "$C_1$ alkyl" refers to methyl (—$CH_3$), "$C_2$ alkyl" refers to ethyl (—$CH_2CH_3$), "$C_3$ alkyl" refers to propyl (—$CH_2CH_2CH_3$) and "$C_4$ alkyl" refers to butyl (e.g. —$CH_2CH_2CH_2CH_3$, —$(CH_3)CHCH_2CH_3$, —$CH_2CH(CH_3)_2$, etc.). Further, as used herein, "Me" refers to methyl, and "Et" refers to ethyl, "i-Pr" refers to isopropyl, "t-Bu" refers to tert-butyl, and "Np" refers to neopentyl.

As used herein, and unless otherwise specified, the term "alkylene" refers to a divalent alkyl moiety containing 1 to 12 carbon atoms (i.e. $C_1$-$C_{12}$ alkylene) in length and meaning the alkylene moiety is attached to the rest of the molecule at both ends of the alkyl unit. For example, alkylenes include, but are not limited to, —$CH_2$—, —$CH_2CH_2$—, —$CH(CH_3)CH_2$—, —$CH_2CH_2CH_2$—, etc. The alkylene group may be linear or branched.

As used herein, and unless otherwise specified, the term "nitrogen-containing alkyl" refers to an alkyl group as defined herein wherein one or more carbon atoms in the alkyl group is substituted with a nitrogen atom or a nitrogen-containing cyclic hydrocarbon having from 2 to 10 carbon atoms (i.e., a nitrogen-containing cyclic $C_2$-$C_{10}$ hydrocarbon), particularly having from 2 to 5 carbon atoms (i.e., a nitrogen-containing cyclic $C_2$-$C_5$ hydrocarbon), and particularly having from 2 to 5 carbon atoms (i.e., a nitrogen-containing cyclic $C_2$-$C_5$ hydrocarbon). The nitrogen-containing cyclic hydrocarbon may have one or more nitrogen atoms. The nitrogen atom(s) may optionally be substituted with one or two $C_1$-$C_6$ alkyl groups. The nitrogen-containing alkyl can have from 1 to 12 carbon atoms (i.e. $C_1$-$C_{12}$ nitrogen-containing alkyl), particularly from 1 to 10 carbon atoms (i.e. $C_1$-$C_{10}$ nitrogen-containing alkyl), particularly from 2 to 10 carbon atoms (i.e. $C_2$-$C_{10}$ nitrogen-containing alkyl), particularly from 3 to 10 carbon atoms (i.e. $C_3$-$C_{10}$ nitrogen-containing alkyl), and particularly from 3 to 8 carbon atoms (i.e. $C_1$-$C_{10}$ nitrogen-containing alkyl). Examples of nitrogen-containing alkyls include, but are not limited to,

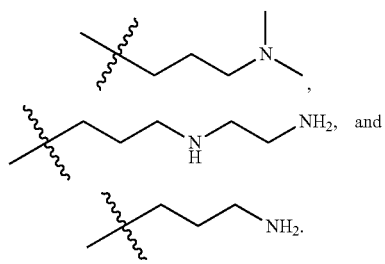

As used herein, and unless otherwise specified, the term "nitrogen-containing alkylene" refers to an alkylene group as defined herein wherein one or more carbon atoms in the alkyl group is substituted with a nitrogen atom. The nitrogen atom(s) may optionally be substituted with one or two $C_1$-$C_6$ alkyl groups. The nitrogen-containing alkylene can have from 1 to 12 carbon atoms (i.e. $C_1$-$C_{12}$ nitrogen-containing alkylene), particularly from 2 to 10 carbon atoms (i.e. $C_2$-$C_{10}$ nitrogen-containing alkylene), particularly from 3 to 10 carbon atoms (i.e. $C_3$-$C_{10}$ nitrogen-containing alkylene), particularly from 4 to 10 carbon atoms (i.e. $C_4$-$C_{10}$ nitrogen-containing alkylene), and particularly from 3 to 8 carbon atoms (i.e. $C_3$-$C_8$ nitrogen-containing alkyl). Examples of nitrogen-containing alkylenes include, but are not limited to,

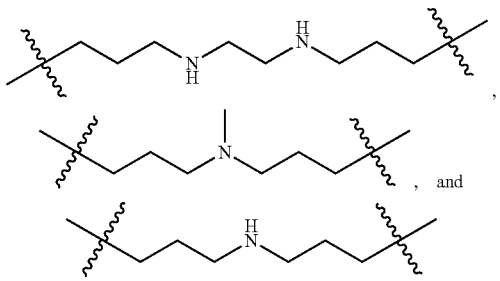

As used herein, and unless otherwise specified, the term "alkenyl" refers to an unsaturated hydrocarbon radical having from 2 to 12 carbon atoms (i.e., $C_2$-$C_{12}$ alkenyl), particularly from 2 to 8 carbon atoms (i.e., $C_2$-$C_8$ alkenyl), particularly from 2 to 6 carbon atoms (i.e., $C_2$-$C_6$ alkenyl), and having one or more (e.g., 2, 3, etc.) carbon-carbon double bonds. The alkenyl group may be linear, branched or cyclic. Examples of alkenyls include, but are not limited to ethenyl (vinyl), 2-propenyl, 3-propenyl, 1,4-pentadienyl, 1,4-butadienyl, 1-butenyl, 2-butenyl and 3-butenyl. "Alkenyl" is intended to embrace all structural isomeric forms of an alkenyl. For example, butenyl encompasses 1,4-butadienyl, 1-butenyl, 2-butenyl and 3-butenyl, etc.

As used herein, and unless otherwise specified, the term "alkenylene" refers to a divalent alkenyl moiety containing 2 to about 12 carbon atoms (i.e. $C_2$-$C_{12}$ alkenylene) in length and meaning that the alkenylene moiety is attached to the rest of the molecule at both ends of the alkyl unit. For example, alkenylenes include, but are not limited to, —CH=CH—, —CH=CHCH$_2$—, —CH=CH=CH—, —CH$_2$CH$_2$CH=CHCH$_2$—, etc.
—CH$_2$CH$_2$—, —CH(CH$_3$)CH$_2$—, —CH$_2$CH$_2$CH$_2$—, etc. The alkenylene group may be linear or branched.

As used herein, and unless otherwise specified, the term "alkynyl" refers to an unsaturated hydrocarbon radical having from 2 to 12 carbon atoms (i.e., $C_2$-$C_{12}$ alkynyl), particularly from 2 to 8 carbon atoms (i.e., $C_2$-$C_8$ alkynyl), particularly from 2 to 6 carbon atoms (i.e., $C_2$-$C_6$ alkynyl), and having one or more (e.g., 2, 3, etc.) carbon-carbon triple bonds. The alkynyl group may be linear, branched or cyclic. Examples of alkynyls include, but are not limited to ethynyl, 1-propynyl, 2-butynyl, and 1,3-butadiynyl. "Alkynyl" is intended to embrace all structural isomeric forms of an alkynyl. For example, butynyl encompassses 2-butynyl, and 1,3-butadiynyl and propynyl encompasses 1-propynyl and 2-propynyl (propargyl).

As used herein, and unless otherwise specified, the term "alkynylene" refers to a divalent alkynyl moiety containing 2 to about 12 carbon atoms (i.e. $C_2$-$C_{12}$ alkenylene) in length and meaning that the alkylene moiety is attached to the rest of the molecule at both ends of the alkyl unit. For example, alkenylenes include, but are not limited to, —C≡C—, —C≡CCH$_2$—, —C≡CCH$_2$C≡C—, —CH$_2$CH$_2$C≡CCH$_2$—, etc.
—CH$_2$CH$_2$—, —CH(CH$_3$)CH$_2$—, —CH$_2$CH$_2$CH$_2$—, etc. The alkynlene group may be linear or branched.

As used herein, and unless otherwise specified, the term "alkoxy" refers to —O-alkyl containing from 1 to about 10 carbon atoms. The alkoxy may be straight-chain or branched-chain. Non-limiting examples include methoxy, ethoxy, propoxy, butoxy, isobutoxy, tert-butoxy, pentoxy, and hexoxy. "$C_1$ alkoxy" refers to methoxy, "$C_2$ alkoxy" refers to ethoxy, "$C_3$ alkoxy" refers to propoxy and "$C_4$ alkoxy" refers to butoxy. Further, as used herein, "OMe" refers to methoxy and "OEt" refers to ethoxy.

As used herein, and unless otherwise specified, the term "aromatic" refers to unsaturated cyclic hydrocarbons having a delocalized conjugated π system and having from 5 to 20 carbon atoms (aromatic $C_5$-$C_{20}$ hydrocarbon), particularly from 5 to 12 carbon atoms (aromatic $C_5$-$C_{12}$ hydrocarbon), and particularly from 5 to 10 carbon atoms (aromatic $C_5$-$C_{12}$ hydrocarbon). Exemplary aromatics include, but are not limited to benzene, toluene, xylenes, mesitylene, ethylbenzenes, cumene, naphthalene, methylnaphthalene, dimethylnaphthalenes, ethylnaphthalenes, acenaphthalene, anthracene, phenanthrene, tetraphene, naphthacene, benzanthracenes, fluoranthrene, pyrene, chrysene, triphenylene, and the like, and combinations thereof. Additionally, the aromatic may comprise one or more heteroatoms. Examples of heteroatoms include, but are not limited to, nitrogen, oxygen, and/or sulfur. Aromatics with one or more heteroatom include, but are not limited to furan, benzofuran, thiophene, benzothiophene, oxazole, thiazole and the like, and combinations thereof. The aromatic may comprise monocyclic, bicyclic, tricyclic, and/or polycyclic rings (in some embodiments, at least monocyclic rings, only monocyclic and bicyclic rings, or only monocyclic rings) and may be fused rings.

As used herein, and unless otherwise specified, the term "aryl" refers to any monocyclic or polycyclic cyclized carbon radical containing 6 to 14 carbon ring atoms, wherein at least one ring is an aromatic hydrocarbon. Examples of aryls include, but are not limited to phenyl, naphthyl, pyridinyl, and indolyl.

As used herein, and unless otherwise specified, the term "aralkyl" refers to an alkyl group substituted with an aryl group. The alkyl group may be a $C_1$-$C_{10}$ alkyl group, particularly a $C_1$-$C_6$, particularly a $C_1$-$C_4$ alkyl group, and particularly a $C_1$-$C_3$ alkyl group. Examples of aralkyl groups include, but are not limited to phenymethyl, phenylethyl, and naphthylmethyl. The aralkyl may comprise one or more heteroatoms and be referred to as a "heteroaralkyl." Examples of heteroatoms include, but are not limited to, nitrogen (i.e., nitrogen-containing heteroaralkyl), oxygen (i.e., oxygen-containing heteroaralkyl), and/or sulfur (i.e., sulfur-containing heteroaralkyl). Examples of heteroaralkyl groups include, but are not limited to, pyridinylethyl, indolylmethyl, furylethyl, and quinolinylpropyl.

As used herein, and unless otherwise specified, the term "heterocyclo" refers to fully saturated, partially saturated or unsaturated or polycyclic cyclized carbon radical containing from 4 to 20 carbon ring atoms and containing one or more heteroatoms atoms. Examples of heteroatoms include, but are not limited to, nitrogen (i.e., nitrogen-containing heterocyclo), oxygen (i.e., oxygen-containing heterocyclo), and/or sulfur (i.e., sulfur-containing heterocyclo). Examples of heterocyclo groups include, but are not limited to, thienyl, furyl, pyrrolyl, piperazinyl, pyridyl, benzoxazolyl, quinolinyl, imidazolyl, pyrrolidinyl, and piperidinyl.

As used herein, and unless otherwise specified, the term "heterocycloalkyl" refers to an alkyl group substituted with a heterocyclo group. The alkyl group may be a $C_1$-$C_{10}$ alkyl group, particularly a $C_1$-$C_6$, particularly a $C_1$-$C_4$ alkyl group, and particularly a $C_1$-$C_3$ alkyl group. Examples of heterocycloalkyl groups include, but are not limited to thienylmethyl, furylethyl, pyrrolylmethyl, piperazinylethyl, pyridylmethyl, benzoxazolylethyl, quinolinylpropyl, and imidazolylpropyl.

As used herein, the term "hydroxyl" refers to an —OH group.

As used herein, the term "mesoporous" refers to solid materials having pores that have a diameter within the range of from about 2 nm to about 50 nm.

As used herein, the term "organosilica" refers to an organosiloxane compound that comprises one or more organic groups bound to two or more Si atoms.

As used herein, the term "silanol" refers to a Si—OH group.

As used herein, the term "silanol content" refers to the percent of the Si—OH groups in a compound and can be calculated by standard methods, such as NMR.

As used herein, the terms "structure directing agent," "SDA," and/or "porogen" refer to one or more compounds added to the synthesis media to aid in and/or guide the polymerization and/or polycondensing and/or organization of the building blocks that form the organosilica material framework. Further, a "porogen" is understood to be a compound capable of forming voids or pores in the resultant organosilica material framework. As used herein, the term "structure directing agent" encompasses and is synonymous and interchangeable with the terms "templating agent" and "template."

As used herein, and unless otherwise specified, the term "adsorption" includes physisorption, chemisorption, and condensation onto a solid material and combinations thereof.

II. Methods For Fabricating A Membrane

The invention relates to methods for manufacturing a membrane, the method comprising:
(a) adding at least one compound of Formula $[Z^1Z^2SiCH_2]_3$ (Ia) into an aqueous mixture that contains essentially no structure directing agent or porogen to form a solution, wherein each $Z^1$ represents a hydroxyl group, a $C_1$-$C_4$ alkoxy group or an oxygen bonded to a silicon atom of another compound and each $Z^2$ represents, a hydroxyl group, a $C_1$-$C_4$ alkoxy group, a $C_1$-$C_4$ alkyl group or an oxygen bonded to a silicon atom of another compound;
(b) coating the solution onto a support to form a coated support;
(c) aging the coated support; and
(d) drying the coated support to obtain a membrane comprising an organosilica material which is a polymer comprising independent units of Formula $[Z^3Z^4SiCH_2]_3$ (I), wherein each $Z^3$ represents a hydroxyl group, a $C_1$-$C_4$ alkoxy group or an oxygen atom bonded to a silicon atom of another unit or an active site on the support and each $Z^4$ represents a hydroxyl group, a $C_1$-$C_4$ alkoxy group, a $C_1$-$C_4$ alkyl group, an oxygen bonded to a silicon atom of another unit or an active site on the support.

As used herein, and unless otherwise specified, "an oxygen atom bonded to a silicon atom of another unit or an active site on the support" means that the oxygen atom can advantageously displace a moiety (particularly an oxygen-containing moiety such as a hydroxyl, an alkoxy or the like), if present, on a silicon atom of another unit or a moiety (particularly an oxygen-containing moiety such as a hydroxyl, an alkoxy or the like), if present, on an active site of the support so the oxygen atom may be bonded directly to the silicon atom of another unit thereby connecting the two units, e.g., via a Si—O—Si linkage or the oxygen atom may be bonded directly to the active site on the support thereby connecting the unit to the support. As used herein, and unless otherwise specified, "a bond to a silicon atom of another unit or an active site on the support" means that the bond can advantageously displace a moiety (particularly an oxygen-containing moiety such as a hydroxyl, an alkoxy or the like), if present, on a silicon atom of another unit or a moiety (particularly an oxygen-containing moiety such as a hydroxyl, an alkoxy or the like), if present, on an active site of the support so there may be a bond directly to the silicon atom of another unit thereby connecting the two units, e.g., via a Si—O—Si linkage or a bond directly to the active site on the support thereby connecting the unit to the support. For clarity, in this bonding scenario, the "another unit" can be a unit of the same type or a unit of a different type. Active sites on a support can include, but are not limited to alumina, SiC, mixed-metal oxide, Yitria, Ti atoms, Si atoms, Zr atoms, and combinations thereof. Many metal oxides surface can be an active site. Additionally or alternatively, it understood herein, that other heteroatoms (e.g., N, S) in addition to oxygen may be bridge the Si atoms of the polymer to the active sites of the support.

II.A. Aqueous Mixture

The aqueous mixture contains essentially no added structure directing agent and/or no added porogen.

As used herein, "no added structure directing agent," and "no added porogen" means either (i) there is no component present in the synthesis of the organosilica material that aids in and/or guides the polymerization and/or polycondensing and/or organization of the building blocks that form the framework of the organosilica material; or (ii) such component is present in the synthesis of the organosilica material in a minor, or a non-substantial, or a negligible amount such that the component cannot be said to aid in and/or guide the polymerization and/or polycondensing and/or organization of the building blocks that form the framework of the organosilica material. Further, "no added structure directing agent" is synonymous with "no added template" and "no added templating agent."

1. Structure Directing Agent

Examples of a structure directing agent can include, but are not limited to, non-ionic surfactants, ionic surfactants, cationic surfactants, silicon surfactants, amphoteric surfactants, polyalkylene oxide surfactants, fluorosurfactants, colloidal crystals, polymers, hyper branched molecules, star-shaped molecules, macromolecules, dendrimers, and combinations thereof. Additionally or alternatively, the surface directing agent can comprise or be a poloxamer, a triblock polymer, a tetraalkylammonium salt, a nonionic polyoxyethylene alkyl, a Gemini surfactant, or a mixture thereof. Examples of a tetraalkylammonium salt can include, but are not limited to, cetyltrimethylammonium halides, such as cetyltrimethylammonium chloride (CTAC), cetyltrimethylammonium bromide (CTAB), and octadecyltrimethylammonium chloride. Other exemplary surface directing agents can additionally or alternatively include hexadecyltrimethylammonium chloride and/or cetylpyridinium bromide.

Poloxamers are block copolymers of ethylene oxide and propylene oxide, more particularly nonionic triblock copolymers composed of a central hydrophobic chain of polyoxypropylene (poly(propylene oxide)) flanked by two hydrophilic chains of polyoxyethylene (poly(ethylene oxide)). Specifically, the term "poloxamer" refers to a polymer having the formula $HO(C_2H_4))a(C_3H_6O)_b(C_2H_4O)_aH$ in which "a" and "b" denote the number of polyoxyethylene and polyoxypropylene units, respectively. Poloxamers are also known by the trade name Pluronic®, for example Pluronic® 123 and Pluronic® F127. An additional triblock polymer is B50-6600.

Nonionic polyoxyethylene alkyl ethers are known by the trade name Brij®, for example Brij® 56, Brij® 58, Brij® 76, Brij® 78. Gemini surfactants are compounds having at least two hydrophobic groups and at least one or optionally two hydrophilic groups per molecule have been introduced.

2. Porogen

A porogen material is capable of forming domains, discrete regions, voids and/or pores in the organosilica material. As used herein, porogen does not include water. An example of a porogen is a block copolymer (e.g., a di-block polymer). Examples of polymer porogens can include, but are not limited to, polyvinyl aromatics, such as polystyrenes, polyvinylpyridines, hydrogenated polyvinyl aromatics, polyacrylonitriles, polyalkylene oxides, such as polyethylene oxides and polypropylene oxides, polyethylenes, polylactic acids, polysiloxanes, polycaprolactones, polycaprolactams, polyurethanes, polymethacrylates, such as polymethylmethacrylate or polymethacrylic acid, polyacrylates, such as polymethylacrylate and polyacrylic acid, polydienes such as polybutadienes and polyisoprenes, polyvinyl chlorides, polyacetals, and amine-capped alkylene oxides, as well as combinations thereof Additionally or alternatively, porogens can be thermoplastic homopolymers and random (as opposed to block) copolymers. As used herein, "homopolymer" means compounds comprising repeating units from a single monomer. Suitable thermoplastic materials can include, but are not limited to, homopolymers or copolymers of polystyrenes, polyacrylates, polymethacrylates, polybutadienes, polyisoprenes, polyphenylene oxides, polypropylene oxides, polyethylene oxides, poly(dimethylsiloxanes), polytetrahydrofurans, polyethylenes, polycyclohexylethylenes, polyethyloxazolines, polyvinylpyridines, polycaprolactones, polylactic acids, copolymers of these materials and mixtures of these materials. Examples of polystyrene include, but are not limited to anionic polymerized polystyrene, syndiotactic polystyrene, unsubstituted and substituted polystyrenes (for example, poly(α-methyl styrene)). The thermoplastic materials may be linear, branched, hyperbranched, dendritic, or star like in nature.

Additionally or alternatively, the porogen can be a solvent. Examples of solvents can include, but are not limited to, ketones (e.g., cyclohexanone, cyclopentanone, 2-heptanone, cycloheptanone, cyclooctanone, cyclohexylpyrrolidinone, methyl isobutyl ketone, methyl ethyl ketone, acetone), carbonate compounds (e.g., ethylene carbonate, propylene carbonate), heterocyclic compounds (e.g., 3-methyl-2-oxazolidinone, dimethylimidazolidinone, N-methylpyrrolidinone, pyridine), cyclic ethers (e.g., dioxane, tetrahydrofuran), chain ethers (e.g., diethyl ether, ethylene glycol dimethyl ether, propylene glycol dimethyl ether, tetraethylene glycol dimethyl ether, polyethylene glycol dimethyl ether, ethylene glycol monomethyl ether, ethylene glycol monoethyl ether, propylene glycol monomethyl ether (PGME), triethylene glycol monobutyl ether, propylene glycol monopropyl ether, triethylene glycol monomethyl ether, diethylene glycol ethyl ether, diethylene glycol methyl ether, dipropylene glycol methyl ether, dipropylene glycol dimethyl ether, propylene glycol phenyl ether, tripropylene glycol methyl ether), alcohols (e.g., methanol, ethanol), polyhydric alcohols (e.g., ethylene glycol, propylene glycol, polyethylene glycol, polypropylene glycol, glycerin, dipropylene glycol), nitrile compounds (e.g., acetonitrile, glutarodinitrile, methoxyacetonitrile, propionitrile, benzonitrile), esters (e.g., ethyl acetate, butyl acetate, methyl lactate, ethyl lactate, methyl methoxypropionate, ethyl ethoxypropionate, methyl pyruvate, ethyl pyruvate, propyl pyruvate, 2-methoxyethyl acetate, ethylene glycol monoethyl ether acetate, propylene glycol monomethyl ether acetate (PGMEA), butyrolactone, phosphoric acid ester, phosphonic acid ester), aprotic polar substances (e.g., dimethyl sulfoxide, sulfolane, dimethylformamide, dimethylacetamide), nonpolar solvents (e.g., toluene, xylene, mesitylene), chlorine-based solvents (e.g., methylene dichloride, ethylene dichloride), benzene, dichlorobenzene, naphthalene, diphenyl ether, diisopropylbenzene, triethylamine, methyl benzoate, ethyl benzoate, butyl benzoate, monomethyl ether acetate hydroxy ethers such as dibenzylethers, diglyme, triglyme, and mixtures thereof.

3. Base/Acid

In various embodiments, the aqueous mixture used in methods provided herein can comprise a base and/or an acid.

In certain embodiments where the aqueous mixture comprises a base, the aqueous mixture can have a pH from about 8 to about 15, from about 8 to about 14.5, from about 8 to about 14, from about 8 to about 13.5, from about 8 to about 13, from about 8 to about 12.5, from about 8 to about 12, from about 8 to about 11.5, from about 8 to about 11, from about 8 to about 10.5, from about 8 to about 10, from about 8 to about 9.5, from about 8 to about 9, from about 8 to about 8.5, from about 8.5 to about 15, from about 8.5 to about 14.5, from about 8.5 to about 14, from about 8.5 to about 13.5, from about 8.5 to about 13, from about 8.5 to about 12.5, from about 8.5 to about 12, from about 8.5 to about 11.5, from about 8.5 to about 11, from about 8.5 to about 10.5, from about 8.5 to about 10, from about 8.5 to about 9.5, from about 8.5 to about 9, from about 9 to about 15, from about 9 to about 14.5, from about 9 to about 14, from about 9 to about 13.5, from about 9 to about 13, from about 9 to about 12.5, from about 9 to about 12, from about 9 to about 11.5, from about 9 to about 11, from about 9 to about 10.5, from about 9 to about 10, from about 9 to about 9.5, from about 9.5 to about 15, from about 9.5 to about 14.5, from about 9.5 to about 14, from about 9.5 to about 13.5, from about 9.5 to about 13, from about 9.5 to about 12.5, from about 9.5 to about 12, from about 9.5 to about 11.5, from about 9.5 to about 11, from about 9.5 to about 10.5, from about 9.5 to about 10, from about 10 to about 15, from about 10 to about 14.5, from about 10 to about 14, from about 10 to about 13.5, from about 10 to about 13, from about 10 to about 12.5, from about 10 to about 12, from about 10 to about 11.5, from about 10 to about 11, from about 10 to about 10.5, from about 10.5 to about 15, from about 10.5 to about 14.5, from about 10.5 to about 14, from about 10.5 to about 13.5, from about 10.5 to about 13, from about 10.5 to about 12.5, from about 10.5 to about 12, from about 10.5 to about 11.5, from about 10.5 to about 11, from about 11 to about 15, from about 11 to about 14.5, from about 11 to about 14, from about 11 to about 13.5, from about 11 to about 13, from about 11 to about 12.5, from about 11 to about 12, from about 11 to about 11.5, from about 11.5 to about 15, from about 11.5 to about 14.5, from about 11.5 to about 14, from about 11.5 to about 13.5, from about 11.5 to about 13, from about 11.5 to about 12.5, from about 11.5 to about 12, from about 12 to about 15, from about 12 to about 14.5, from about 12 to about 14, from about 12 to about 13.5, from about 12 to about 13, from about 12 to about 12.5, from about 12.5 to about 15, from about 12.5 to about 14.5, from about 12.5 to about 14, from about 12.5 to about 13.5, from about 12.5 to about 13, from about 12.5 to about 15, from about 12.5 to about 14.5, from about 12.5 to about 14, from about 12.5 to about 13.5, from about 12.5 to about 13, from about 13 to about 15, from about 13 to about 14.5, from about 13 to about 14, from about 13 to about 13.5, from about 13.5 to about 15, from about 13.5 to about 14.5, from about 13.5 to about 14, from about 14 to about 15, from about 14 to about 14.5, and from about 14.5 to about 15.

In a particular embodiment comprising a base, the pH can be from about 9 to about 15, from about 9 to about 14, from about 8 to about 15, or from about 8 to about 14.

Exemplary bases can include, but are not limited to, sodium hydroxide, potassium hydroxide, lithium hydroxide, pyridine, pyrrole, piperazine, pyrrolidine, piperidine, picoline, monoethanolamine, diethanolamine, dimethylmonoethanolamine, monomethyldiethanolamine, triethanolamine, diazabicyclooctane, diazabicyclononane, diazabicycloundecene, tetramethylammonium hydroxide, tetraethylammonium hydroxide, tetrapropylammonium hydroxide, tetrabutylammonium hydroxide, ammonia, ammonium hydroxide, methylamine, ethylamine, propylamine, butylamine, pentylamine, hexylamine, octylamine, nonylamine, decylamine, N,N-dimethylamine, N,N-diethylamine, N,N-dipropylamine, N,N-dibutylamine, trimethylamine, triethylamine, tripropylamine, tributylamine, cyclohexylamine, trimethylimidine, 1-amino-3-methylbutane, dimethylglycine, 3-amino-3-methylamine, and the like. These bases may be used either singly or in combination. In a particular embodiment, the base can comprise or be sodium hydroxide and/or ammonium hydroxide.

In certain embodiments where the aqueous mixture comprises an acid, the aqueous mixture can have a pH from about 0.01 to about 6.0, from about 0.01 to about 5, from about 0.01 to about 4, from about 0.01 to about 3, from about 0.01 to about 2, from about 0.01 to about 1, from about 0.1 to about 6.0, about 0.1 to about 5.5, about 0.1 to about 5.0, from about 0.1 to about 4.8, from about 0.1 to about 4.5, from about 0.1 to about 4.2, from about 0.1 to about 4.0, from about 0.1 to about 3.8, from about 0.1 to about 3.5, from about 0.1 to about 3.2, from about 0.1 to about 3.0, from about 0.1 to about 2.8, from about 0.1 to about 2.5, from about 0.1 to about 2.2, from about 0.1 to about 2.0, from about 0.1 to about 1.8, from about 0.1 to about 1.5, from about 0.1 to about 1.2, from about 0.1 to about 1.0, from about 0.1 to about 0.8, from about 0.1 to about 0.5, from about 0.1 to about 0.2, about 0.2 to about 6.0, about 0.2 to about 5.5, from about 0.2 to about 5, from about 0.2 to about 4.8, from about 0.2 to about 4.5, from about 0.2 to about 4.2, from about 0.2 to about 4.0, from about 0.2 to about 3.8, from about 0.2 to about 3.5, from about 0.2 to about 3.2, from about 0.2 to about 3.0, from about 0.2 to about 2.8, from about 0.2 to about 2.5, from about 0.2 to about 2.2, from about 0.2 to about 2.0, from about 0.2 to about 1.8, from about 0.2 to about 1.5, from about 0.2 to about 1.2, from about 0.2 to about 1.0, from about 0.2 to about 0.8, from about 0.2 to about 0.5, about 0.5 to about 6.0, about 0.5 to about 5.5, from about 0.5 to about 5, from about 0.5 to about 4.8, from about 0.5 to about 4.5, from about 0.5 to about 4.2, from about 0.5 to about 4.0, from about 0.5 to about 3.8, from about 0.5 to about 3.5, from about 0.5 to about 3.2, from about 0.5 to about 3.0, from about 0.5 to about 2.8, from about 0.5 to about 2.5, from about 0.5 to about 2.2, from about 0.5 to about 2.0, from about 0.5 to about 1.8, from about 0.5 to about 1.5, from about 0.5 to about 1.2, from about 0.5 to about 1.0, from about 0.5 to about 0.8, about 0.8 to about 6.0, about 0.8 to about 5.5, from about 0.8 to about 5, from about 0.8 to about 4.8, from about 0.8 to about 4.5, from about 0.8 to about 4.2, from about 0.8 to about 4.0, from about 0.8 to about 3.8, from about 0.8 to about 3.5, from about 0.8 to about 3.2, from about 0.8 to about 3.0, from about 0.8 to about 2.8, from about 0.8 to about 2.5, from about 0.8 to about 2.2, from about 0.8 to about 2.0, from about 0.8 to about 1.8, from about 0.8 to about 1.5, from about 0.8 to about 1.2, from about 0.8 to about 1.0, about 1.0 to about 6.0, about 1.0 to about 5.5, from about 1.0 to about 5.0, from about 1.0 to about 4.8, from about 1.0 to about 4.5, from about 1.0 to about 4.2, from about 1.0 to about 4.0, from about 1.0 to about 3.8, from about 1.0 to about 3.5, from about 1.0 to about 3.2, from about 1.0 to about 3.0, from about 1.0 to about 2.8, from about 1.0 to about 2.5, from about 1.0 to about 2.2, from about 1.0 to about 2.0, from about 1.0 to about 1.8, from about 1.0 to about 1.5, from about 1.0 to about 1.2, about 1.2 to about 6.0, about 1.2 to about 5.5, from about 1.2 to about 5.0, from about 1.2 to about 4.8, from about 1.2 to about 4.5, from about 1.2 to about 4.2, from about 1.2 to about 4.0, from about 1.2 to about 3.8, from about 1.2 to about 3.5, from about 1.2 to about 3.2, from about 1.2 to about 3.0, from about 1.2 to about 2.8, from about 1.2 to about 2.5, from about 1.2 to about 2.2, from about 1.2 to about 2.0, from about 1.2 to about 1.8, from about 1.2 to about 1.5, about 1.5 to about 6.0, about 1.5 to about 5.5, from about 1.5 to about 5.0, from about 1.5 to about 4.8, from about 1.5 to about 4.5, from about 1.5 to about 4.2, from about 1.5 to about 4.0, from about 1.5 to about 3.8, from about 1.5 to about 3.5, from about 1.5 to about 3.2, from about 1.5 to about 3.0, from about 1.5 to about 2.8, from about 1.5 to about 2.5, from about 1.5 to about 2.2, from about 1.5 to about 2.0, from about 1.5 to about 1.8, about 1.8 to about 6.0, about 1.8 to about 5.5, from about 1.8 to about 5.0, from about 1.8 to about 4.8, from about 1.8 to about 4.5, from about 1.8 to about 4.2, from about 1.8 to about 4.0, from about 1.8 to about 3.8, from about 1.8 to about 3.5, from about 1.8 to about 3.2, from about 1.8 to about 3.0, from about 1.8 to about 2.8, from about 1.8 to about 2.5, from about 1.8 to about 2.2, from about 1.8 to about 2.0, about 2.0 to about 6.0, about 2.0 to about 5.5, from about 2.0 to about 5.0, from about 2.0 to about 4.8, from about 2.0 to about 4.5, from about 2.0 to about 4.2, from about 2.0 to about 4.0, from about 2.0 to about 3.8, from about 2.0 to about 3.5, from about 2.0 to about 3.2, from about 2.0 to about 3.0, from about 2.0 to about 2.8, from about 2.0 to about 2.5, from about 2.0 to about 2.2, about 2.2 to about 6.0, about 2.2 to about 5.5, from about 2.2 to about 5.0, from about 2.2 to about 4.8, from about 2.2 to about 4.5, from about 2.2 to about 4.2, from about 2.2 to about 4.0, from about 2.2 to about 3.8, from about 2.2 to about 3.5, from about 2.2 to about 3.2, from about 2.2 to about 3.0, from about 2.2 to about 2.8, from about 2.2 to about 2.5, about 2.5 to about 6.0, about 2.5 to about 5.5, from about 2.5 to about 5.0, from about 2.5 to about 4.8, from about 2.5 to about 4.5, from about 2.5 to about 4.2, from about 2.5 to about 4.0, from about 2.5 to about 3.8, from about 2.5 to about 3.5, from about 2.5 to about 3.2, from about 2.5 to about 3.0, from about 2.5 to about 2.8, from about 2.8 to about 6.0, from about 2.8 to about 5.5, from about 2.8 to about 5.0, from about 2.8 to about 4.8, from about 2.8 to about 4.5, from about 2.8 to about 4.2, from about 2.8 to about 4.0, from about 2.8 to about 3.8, from about 2.8 to about 3.5, from about 2.8 to about 3.2, from about 2.8 to about 3.0, from about 3.0 to about 6.0, from about 3.5 to about 5.5, from about 3.0 to about 5.0, from about 3.0 to about 4.8, from about 3.0 to about 4.5, from about 3.0 to about 4.2, from about 3.0 to about 4.0, from about 3.0 to about 3.8, from about 3.0 to about 3.5, from about 3.0 to about 3.2, from about 3.2 to about 6.0, from about 3.2 to about 5.5, from about 3.2 to about 5, from about 3.2 to about 4.8, from about 3.2 to about 4.5, from about 3.2 to about 4.2, from about 3.2 to about 4.0, from about 3.2 to about 3.8, from about 3.2 to about 3.5, from about 3.5 to about 6.0, from about 3.5 to about 5.5, from about 3.5 to about 5, from about 3.5 to about 4.8, from about 3.5 to about 4.5, from about 3.5 to about 4.2, from about 3.5 to about 4.0, from about 3.5 to about 3.8, from about 3.8 to about 5, from about 3.8 to about 4.8, from about 3.8 to about 4.5, from about 3.8 to about 4.2, from about 3.8 to about 4.0, from about 4.0 to about 6.0, from about 4.0 to about 5.5, from about 4.0 to about 5, from about 4.0 to about 4.8, from about 4.0 to about 4.5, from about 4.0 to about 4.2, from about 4.2 to about 5, from about 4.2 to about 4.8, from about 4.2 to about 4.5, from about 4.5 to about 5, from about 4.5 to about 4.8, or from about 4.8 to about 5.

In a particular embodiment comprising an acid, the pH can be from about 0.01 to about 6.0, about 0.2 to about 6.0, about 0.2 to about 5.0 or about 0.2 to about 4.5.

Exemplary acids can include, but are not limited to, inorganic acids such as hydrochloric acid, nitric acid, sulfuric acid, hydrofluoric acid, phosphoric acid, boric acid and oxalic acid; and organic acids such as acetic acid, propionic acid, butanoic acid, pentanoic acid, hexanoic acid, heptanoic acid, octanoic acid, nonanoic acid, decanoic acid, oxalic acid, maleic acid, methylmalonic acid, adipic acid, sebacic acid, gallic acid, butyric acid, mellitic acid, arachidonic acid, shikimic acid, 2-ethylhexanoic acid, oleic acid, stearic acid, linoleic acid, linolenic acid, salicylic acid, benzoic acid, p-amino-benzoic acid, p-toluenesulfonic acid, benzenesulfonic acid, monochloroacetic acid, dichloroacetic acid, trichloroacetic acid, trifluoroacetic acid, formic acid, malonic acid, sulfonic acid, phthalic acid, fumaric acid, citric acid, tartaric acid, succinic acid, itaconic acid, mesaconic acid, citraconic acid, malic acid, a hydrolysate of glutaric acid, a hydrolysate of maleic anhydride, a hydrolysate of phthalic anhydride, and the like. These acids may be used either singly or in combination. In a particular embodiment, the acid can comprise or be hydrochloric acid.

In various aspects, adjusting the pH of the aqueous mixture can affect the total surface area, microporous surface area and pore volume of the organosilica material made. Thus, the porosity of the organosilica material may be adjusted by adjusting the pH of the aqueous mixture.

For example, when the aqueous mixture is basic and has a pH between about 8 to about 14, in particular about 9 to about 14, the organosilica material made may have one or more of the following characteristics:
(i) a total surface area of about 200 $m^2/g$ to about 1800 $m^2/g$, particularly about 300 $m^2/g$ to about 1700 $m^2/g$, and particularly about 400 $m^2/g$ to about 1700 $m^2/g$;
(ii) a microporous surface area of about 0 $m^2/g$ to about 700 $m^2/g$, and particularly about 0 $m^2/g$ to about 700 $m^2/g$;
(iii) a pore volume of about 0.2 $cm^3/g$ to about 3 $cm^3/g$, and particularly of about 0.8 $cm^3/g$ to about 1.4 $cm^3/g$.

Additionally or alternatively, when the aqueous mixture is acidic and has a pH between about 0.1 to about 7, particularly about 0.1 to about 5, particularly about 0.1 to about 4.5, the organosilica material made may have one or more of the following characteristics:
(iv) a total surface area of about 100 $m^2/g$ to about 1500 $m^2/g$, particularly about 100 $m^2/g$ to about 900 $m^2/g$, and particularly about 200 $m^2/g$ to about 900 $m^2/g$;
(v) a microporous surface area of about 100 $m^2/g$ to about 600 $m^2/g$, and particularly about 0 $m^2/g$ to about 500 $m^2/g$;
(vi) a pore volume of about 0.1 $cm^3/g$ to about 1.2 $cm^3/g$, and particularly of about 0.1 $cm^3/g$ to about 0.6 $cm^3/g$.

Thus, the total surface area of an organosilica material made with a basic aqueous mixture may increase when compared to an organosilica material made with an acidic aqueous mixture. Further, the pore volume of an organosilica material made with a basic aqueous mixture may increase when compared to an organosilica material made with an acidic aqueous mixture. However, the microporous surface area of an organosilica material made with a basic aqueous mixture may decrease when compared to an organosilica material made with an acidic aqueous mixture.

II.B. Compounds of Formula (Ia)

The methods provided herein comprise the step of adding at least one compound of Formula $[Z^1Z^2SiCH_2]_3$ (Ia) into the aqueous mixture to form a solution, wherein each $Z^1$ can be a hydroxyl group, a $C_1$-$C_4$ alkoxy group, or an oxygen atom bonded to a silicon atom of another compound and each $Z^2$ can be a hydroxyl group, a $C_1$-$C_4$ alkoxy group or a $C_1$-$C_4$ alkyl group, or an oxygen atom bonded to a silicon atom of another compound.

As used herein, and unless otherwise specified, "a bond to a silicon atom of another compound" means the bond can advantageously displace a moiety (particularly an oxygen-containing moiety such as a hydroxyl, an alkoxy or the like), if present, on a silicon atom of the another compound so there may be a bond directly to the silicon atom of the another compound thereby connecting the two compounds, e.g., via a Si—O—Si linkage. As used herein, and unless otherwise specified, "an oxygen atom bonded to a silicon atom of another compound" means that the oxygen atom can advantageously displace a moiety (particularly an oxygen-containing moiety such as a hydroxyl), if present, on a silicon atom of the another compound so the oxygen atom may be bonded directly to the silicon atom of the another compound thereby connecting the two compounds, e.g., via a Si—O—Si linkage. For clarity, in these bonding scenarios, the "another compound" can be a compound of the same type or a compound of a different type.

In one embodiment, each $Z^1$ can be a hydroxyl group.

Additionally or alternatively, each $Z^1$ can comprise a $C_1$-$C_3$ alkoxy or methoxy or ethoxy.

Additionally or alternatively, each $Z^1$ can be a hydroxyl group or a $C_1$-$C_2$ alkoxy group.

Additionally or alternatively, each $Z^1$ can be an oxygen atom bonded to a silicon atom of another compound.

Additionally or alternatively, each $Z^1$ can be a hydroxyl group, a $C_1$-$C_2$ alkoxy group or an oxygen atom bonded to a silicon atom of another compound.

Additionally or alternatively, each $Z^2$ can be a hydroxyl group.

Additionally or alternatively, each $Z^2$ can comprise a $C_1$-$C_4$ alkoxy, a $C_1$-$C_3$ alkoxy or methoxy or ethoxy. Additionally or alternatively, each $Z^2$ can comprise methyl, ethyl or propyl, such as a methyl or ethyl.

Additionally or alternatively, each $Z^2$ can be a hydroxyl group, a $C_1$-$C_2$ alkoxy group or a $C_1$-$C_2$ alkyl group.

Additionally or alternatively, each $Z^1$ can be an oxygen atom bonded to a silicon atom of another compound.

Additionally or alternatively, each $Z^2$ can be a hydroxyl group, a $C_1$-$C_2$ alkoxy group, a $C_1$-$C_2$ alkyl group or an oxygen atom bonded to a silicon atom of another compound.

Additionally or alternatively, each $Z^1$ can be a hydroxyl group, a $C_1$-$C_2$ alkoxy group or an oxygen atom bonded to a silicon atom of another compound and each $Z^2$ can be a hydroxyl group, a $C_1$-$C_2$ alkoxy group, a $C_1$-$C_2$ alkyl group or an oxygen atom bonded to a silicon atom of another compound.

Additionally or alternatively, each $Z^1$ can a $C_1$-$C_2$ alkoxy group and each $Z^2$ can be a $C_1$-$C_2$ alkoxy group or a $C_1$-$C_2$ alkyl group.

Additionally or alternatively, each $Z^1$ can be hydroxyl, methoxy, ethoxy or an oxygen atom bonded to a silicon atom of another compound and each $Z^2$ can be methyl or ethyl.

In a particular embodiment, each $Z^1$ and each $Z^2$ can be ethoxy, such that the compound corresponding to Formula (Ia) can be 1,1,3,3,5,5-hexaethoxy-1,3,5-trisilacyclohexane, $[(EtO)_2SiCH_2]_3$.

In a particular embodiment, each $Z^1$ can be ethoxy and each $Z^2$ can be methyl, such that compound corresponding to Formula (Ia) can be 1,3,5-trimethyl-1,3,5-triethoxy-1,3,5-trisilacyclohexane, $[EtOCH_3SiCH_2]_3$.

In various aspects, more than one compound of Formula (Ia) (e.g., same or different compound) may be added to the aqueous mixture to form a solution. For example, $[(EtO)_2SiCH_2]_3$ and $[EtOCH_3SiCH_2]_3$ may both be added to the aqueous mixture to form a solution.

When more than one compound of Formula (Ia) is used, the respective compounds may be used in a wide variety of molar ratios. For example, if two compounds of Formula (Ia) are used, the molar ratio of each compound may vary from 1:99 to 99:1, such as from 10:90 to 90:10. The use of different compounds of Formula (Ia) allows to tailor the properties of the organosilica materials made by the process of the invention, as will be further explained in the examples and in the section of this specification describing the properties of the organosilicas made by the present processes.

II.C. Compounds of Formula (II)

In additional embodiments, the methods provided herein can further comprise adding to the aqueous solution a compound of Formula $R^1OR^2R^3R^4Si$ (II), wherein each $R^1$ can be a hydrogen atom, a $C_1$-$C_6$ alkyl group or a bond to a silicon atom of another compound, and $R^2$, $R^3$ and $R^4$ each independently can be selected from the group consisting of a hydrogen atom, a $C_1$-$C_6$ alkyl group, a $C_1$-$C_6$ alkoxy group, a nitrogen-containing $C_1$-$C_{10}$ alkyl group, a nitrogen-containing heteroaralkyl group, a nitrogen-containing optionally substituted heterocycloalkyl group, and an oxygen atom bonded to a silicon atom of another compound.

In one embodiment, $R^1$ can be a hydrogen atom.

Additionally or alternatively, each $R^1$ can be a $C_1$-$C_5$ alkyl group, a $C_1$-$C_4$ alkyl group, a $C_1$-$C_3$ alkyl group, a $C_1$-$C_2$ alkyl group, or methyl. In particular, each $R^1$ can be methyl or ethyl.

Additionally or alternatively, each $R^1$ can be a bond to a silicon atom of another compound Additionally or alternatively, $R^2$, $R^3$ and $R^4$ can be each independently a $C_1$-$C_5$ alkyl group, a $C_1$-$C_4$ alkyl group, a $C_1$-$C_3$ alkyl group, a $C_1$-$C_2$ alkyl group, or methyl.

Additionally or alternatively, each $R^1$ can be a $C_1$-$C_2$ alkyl group and $R^2$, $R^3$ and $R^4$ can be each independently a $C_1$-$C_2$ alkyl group.

Additionally or alternatively, $R^2$, $R^3$ and $R^4$ can be each independently a $C_1$-$C_5$ alkoxy group, a $C_1$-$C_4$ alkoxy group, a $C_1$-$C_3$ alkoxy group, a $C_1$-$C_2$ alkoxy group, or methoxy.

Additionally or alternatively, each $R^1$ can be a $C_1$-$C_2$ alkyl group and $R^2$, $R^3$ and $R^4$ can be each independently a $C_1$-$C_2$ alkoxy group.

Additionally or alternatively, each $R^1$ can be a $C_1$-$C_2$ alkyl group and $R^2$, $R^3$ and $R^4$ can be each independently a $C_1$-$C_2$ alkyl group or a $C_1$-$C_2$ alkoxy group.

Additionally or alternatively, $R^2$, $R^3$ and $R^4$ can be each independently a nitrogen-containing $C_1$-$C_9$ alkyl group, a nitrogen-containing $C_1$-$C_8$ alkyl group, a nitrogen-containing $C_1$-$C_7$ alkyl group, a nitrogen-containing $C_1$-$C_6$ alkyl group, a nitrogen-containing $C_1$-$C_5$ alkyl group, a nitrogen-containing $C_1$-$C_4$ alkyl group, a nitrogen-containing $C_1$-$C_3$ alkyl group, a nitrogen-containing $C_1$-$C_2$ alkyl group, or a methylamine. In particular, $R^2$, $R^3$ and $R^4$ can be each independently a nitrogen-containing $C_2$-$C_{10}$ alkyl group, a nitrogen-containing $C_3$-$C_{10}$ alkyl group, a nitrogen-containing $C_3$-$C_9$ alkyl group, or a nitrogen-containing $C_3$-$C_8$ alkyl group. The aforementioned nitrogen-containing alkyl groups may have one or more nitrogen atoms (e.g., 2, 3, etc.). Examples of nitrogen-containing $C_1$-$C_{10}$ alkyl groups include, but are not limited to,

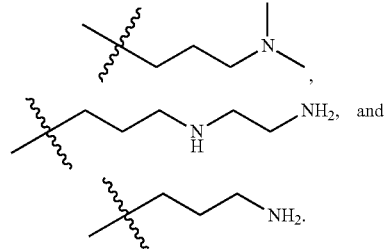

Additionally or alternatively, each $R^1$ can be a $C_1$-$C_2$ alkyl group and $R^2$, $R^3$ and $R^4$ can be each independently a nitrogen-containing $C_3$-$C_8$ alkyl group.

Additionally or alternatively, each $R^1$ can be a $C_1$-$C_2$ alkyl group and $R^2$, $R^3$ and $R^4$ can be each independently a $C_1$-$C_2$ alkyl group, a $C_1$-$C_2$ alkoxy group or a nitrogen-containing $C_3$-$C_8$ alkyl group.

Additionally or alternatively, $R^2$, $R^3$ and $R^4$ can be each independently a nitrogen-containing heteroaralkyl group. The nitrogen-containing heteroaralkyl group can be a nitrogen-containing $C_4$-$C_{12}$ heteroaralkyl group, a nitrogen-containing $C_4$-$C_{10}$ heteroaralkyl group, or a nitrogen-containing $C_4$-$C_8$ heteroaralkyl group. Examples of nitrogen-containing heteroaralkyl groups include but are not limited to pyridinylethyl, pyridinylpropyl, pyridinylmethyl, indolylmethyl, pyrazinylethyl, and pyrazinylpropyl. The aforementioned nitrogen-containing heteroaralkyl groups may have one or more nitrogen atoms (e.g., 2, 3, etc.).

Additionally or alternatively, each $R^1$ can be a $C_1$-$C_2$ alkyl group and $R^2$, $R^3$ and $R^4$ can be each independently a nitrogen-containing heteroaralkyl group.

Additionally or alternatively, each $R^1$ can be a $C_1$-$C_2$ alkyl group and $R^2$, $R^3$ and $R^4$ can be each independently a $C_1$-$C_2$ alkyl group, a $C_1$-$C_2$ alkoxy group, a nitrogen-containing $C_3$-$C_8$ alkyl group or a nitrogen-containing heteroaralkyl group.

Additionally or alternatively, $R^2$, $R^3$ and $R^4$ can be each independently a nitrogen-containing heterocycloalkyl group, wherein the heterocycloalkyl group may be optionally substituted with a $C_1$-$C_6$ alkyl group, particularly a $C_1$-$C_4$ alkyl group. The nitrogen-containing heterocycloalkyl group can be a nitrogen-containing $C_4$-$C_{12}$ heterocycloalkyl group, a nitrogen-containing $C_4$-$C_{10}$ heterocycloalkyl group, or a nitrogen-containing $C_4$-$C_8$ heterocycloalkyl group. Examples of nitrogen-containing heterocycloalkyl groups include but are not limited to piperazinylethyl, piperazinylpropyl, piperidinylethyl, piperidinylpropyl. The aforementioned nitrogen-containing heterocycloalkyl groups may have one or more nitrogen atoms (e.g., 2, 3, etc.).

Additionally or alternatively, each $R^1$ can be a $C_1$-$C_2$ alkyl group and $R^2$, $R^3$ and $R^4$ can be each independently a nitrogen-containing optionally substituted heterocycloalkyl group.

Additionally or alternatively, each $R^1$ can be a $C_1$-$C_2$ alkyl group and $R^2$, $R^3$ and $R^4$ can be each independently a $C_1$-$C_2$ alkyl group, a $C_1$-$C_2$ alkoxy group, a nitrogen-containing $C_3$-$C_8$ alkyl group, a nitrogen-containing heteroaralkyl group, or a nitrogen-containing optionally substituted heterocycloalkyl group.

Additionally or alternatively, $R^2$, $R^3$ and $R^4$ can be each independently an oxygen atom bonded to a silicon atom of another compound.

Additionally or alternatively, each $R^1$ can be a hydrogen atom, a $C_1$-$C_2$ alkyl group or a bond to a silicon atom of another compound and $R^2$, $R^3$ and $R^4$ can be each independently a $C_1$-$C_2$ alkyl group, $C_1$-$C_2$ alkoxy group, a nitrogen-containing $C_3$-$C_{10}$ alkyl group, a nitrogen-containing $C_4$-$C_{10}$ heteroaralkyl group, a nitrogen-containing optionally substituted $C_4$-$C_{10}$ heterocycloalkyl group, or an oxygen atom bonded to a silicon atom of another compound.

Additionally or alternatively, each $R^1$ can be a $C_1$-$C_2$ alkyl group and $R^2$, $R^3$ and $R^4$ can be each independently a $C_1$-$C_2$ alkyl group, $C_1$-$C_2$ alkoxy group, a nitrogen-containing $C_3$-$C_{10}$ alkyl group, a nitrogen-containing $C_4$-$C_{10}$ heteroaralkyl group, or a nitrogen-containing optionally substituted $C_4$-$C_{10}$ heterocycloalkyl group In a particular embodiment, each $R^1$ can be ethyl and each $R^2$, $R^3$ and $R^4$ can be ethoxy, such that the compound corresponding to Formula (II) can be tetraethyl orthosilicate (TEOS) $((EtO)_4Si)$.

In another particular embodiment, each $R^1$ can be ethyl, each $R^2$ can be methyl and each $R^3$ and $R^4$ can be ethoxy, such that the compound corresponding to Formula (II) can be methyltriethoxysilane (MTES) $((EtO)_3CH_3Si)$.

In another particular embodiment, each $R^1$ can be ethyl, each $R^2$ and $R^3$ can be ethoxy and each $R^4$ can be

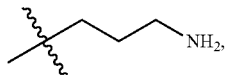

such that the compound corresponding to Formula (II) can be (3-aminopropyl)triethoxysilane $(H_2N(CH_2)_3 (EtO)_3Si)$.

In another particular embodiment, each $R^1$ can be methyl, each $R^2$ and $R^3$ can be methoxy and each $R^4$ can be

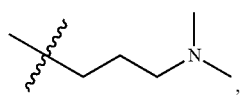

such that the compound corresponding to Formula (II) can be (N,N-dimethylaminopropyl)trimethoxysilane $(((CH_3)_2N(CH_2)_3)(MeO)_3Si)$.

In another particular embodiment, each $R^1$ can be ethyl, each $R^2$ and $R^3$ can be ethoxy and each $R^4$ can be

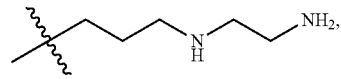 [SMILES: *CCCNCCN]

such that the compound corresponding to Formula (II) can be (N-(2-aminoethyl)-3-aminopropyltriethoxysilane $((H_2N(CH_2)_2NH(CH_2)_3)(EtO)_2Si)$.

In another particular embodiment, each $R^1$ can be ethyl, each $R^2$ and $R^3$ can be ethoxy and each $R^4$ can be

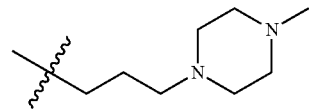

such that the compound corresponding to Formula (II) can be 4-methyl-1-(3-triethoxysilylpropyl)-piperazine.

In another particular embodiment, each $R^1$ can be ethyl, each $R^2$ and $R^3$ can be ethoxy and each $R^4$ can be

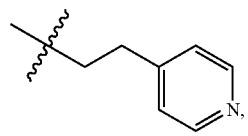

such that the compound corresponding to Formula (II) can be 4-(2-(triethoxysilyl)ethyl)pyridine.

In another particular embodiment, each $R^1$ can be ethyl, each $R^2$ and $R^3$ can be ethoxy and $R^4$ can be

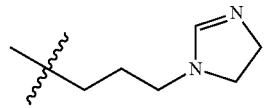

such that the compound corresponding to Formula (II) can be 1-(3-(triethoxysilyl)propyl)-4,5-dihydro-1H-imidazole.

The molar ratio of compound of Formula (Ia) to compound of Formula (II) may vary within wide limits, such as from about 99:1 to about 1:99, from about 1:5 to about 5:1, from about 4:1 to about 1:4 or from about 3:2 to about 2:3. For example, a molar ratio of compound of Formula (Ia) to compound of Formula (II) can be from about 4:1 to 1:4 or from about 2.5:1 to about 1:2.5, about 2:1 to about 1:2, such as about 1.5:1 to about 1.5:1.

II.D. Compounds of Formula (III)

In additional embodiments, the methods provided herein can further comprise adding to the aqueous solution a compound of Formula $Z^5Z^6Z^7Si$—R—$SiZ^5Z^6Z^7$ (III), wherein each $Z^5$ independently can be a hydroxyl group, a $C_1$-$C_4$ alkoxy group or an oxygen atom bonded to a silicon atom of another compound; each $Z^6$ and $Z^7$ independently can be a hydroxyl group, a $C_1$-$C_4$ alkoxy group, a $C_1$-$C_4$ alkyl group or an oxygen atom bonded to a silicon atom of another compound; and each R can be selected from the group consisting a $C_1$-$C_8$ alkylene group, a $C_2$-$C_8$ alkenylene group, a $C_2$-$C_8$ alkynylene group, a nitrogen-containing $C_1$-$C_{10}$ alkylene group, an optionally substituted $C_6$-$C_{20}$ aralkyl group, and an optionally substituted $C_4$-$C_{20}$ heterocycloalkyl group.

In one embodiment, each $Z^5$ can be a hydroxyl group.

Additionally or alternatively, each $Z^5$ can be a $C_1$-$C_3$ alkoxy group, a $C_1$-$C_2$ alkoxy group, or methoxy.

Additionally or alternatively, each $Z^5$ can be an oxygen atom bonded to a silicon atom of another compound.

Additionally or alternatively, each $Z^6$ and $Z^7$ independently can be a hydroxyl group.

Additionally or alternatively, each $Z^6$ and $Z^7$ independently can be a $C_1$-$C_3$ alkoxy group, a $C_1$-$C_2$ alkoxy group, or methoxy.

Additionally or alternatively, each $Z^5$ can be a $C_1$-$C_2$ alkoxy group and each $Z^6$ and $Z^7$ independently can be a $C_1$-$C_2$ alkoxy group.

Additionally or alternatively, each $Z^6$ and $Z^7$ independently can be a $C_1$-$C_3$ alkyl group, a $C_1$-$C_2$ alkyl group, or methyl.

Additionally or alternatively, each $Z^5$ can be a $C_1$-$C_2$ alkoxy group and each $Z^6$ and $Z^7$ independently can be a $C_1$-$C_2$ alkyl group.

Additionally or alternatively, each $Z^6$ and $Z^7$ independently can be an oxygen atom bonded to a silicon atom of another compound.

Additionally or alternatively, each $Z^5$ can be a hydroxyl group, a $C_1$-$C_2$ alkoxy group or an oxygen atom bonded to a silicon atom of another compound and each $Z^6$ and $Z^7$ independently can be a hydroxyl group, a $C_1$-$C_2$ alkoxy group, a $C_1$-$C_2$ alkyl group or an oxygen atom bonded to a silicon atom of another compound.

Additionally or alternatively, each $Z^5$ can be a $C_1$-$C_2$ alkoxy group and each $Z^6$ and $Z^7$ independently can be a $C_1$-$C_2$ alkoxy group or a $C_1$-$C_2$ alkyl group.

Additionally or alternatively, each R can be a $C_1$-$C_7$ alkylene group, a $C_1$-$C_6$ alkylene group, a $C_1$-$C_5$ alkylene group, a $C_1$-$C_4$ alkylene group, a $C_1$-$C_3$ alkylene group, a $C_1$-$C_2$ alkylene group, or —$CH_2$—.

Additionally or alternatively, each $Z^5$ can be a $C_1$-$C_2$ alkoxy group; each $Z^6$ and $Z^7$ independently can be a $C_1$-$C_2$ alkoxy group or a $C_1$-$C_2$ alkyl group; and each R can be a $C_1$-$C_2$ alkylene group.

Additionally or alternatively, each R can be a $C_2$-$C_7$ alkenylene group, a $C_1$-$C_6$ alkenylene group, a $C_2$-$C_5$ alkenylene group, a $C_2$-$C_4$ a alkenylene group, a $C_2$-$C_3$ alkenylene group, or —CH═CH—.

Additionally or alternatively, each $Z^5$ can be a $C_1$-$C_2$ alkoxy group; each $Z^6$ and $Z^7$ independently can be a $C_1$-$C_2$ alkoxy group or a $C_1$-$C_2$ alkyl group; and each R can be a $C_1$-$C_2$ alkenylene group.

Additionally or alternatively, each $Z^5$ can be a $C_1$-$C_2$ alkoxy group; each $Z^6$ and $Z^7$ independently can be a $C_1$-$C_2$ alkoxy group or a $C_1$-$C_2$ alkyl group; and each R can be a $C_1$-$C_2$ alkylene group or a $C_1$-$C_2$ alkenylene group.

Additionally or alternatively, each R can be a $C_2$-$C_7$ alkynylene group, a $C_1$-$C_6$ alkynylene group, a $C_2$-$C_5$ alkynylene group, a $C_2$-$C_4$ a alkynylene group, a $C_2$-$C_3$ alkynylene group, or —C≡C—.

Additionally or alternatively, each $Z^5$ can be a $C_1$-$C_2$ alkoxy group; each $Z^6$ and $Z^7$ independently can be a $C_1$-$C_2$ alkoxy group or a $C_1$-$C_2$ alkyl group; and each R can be a $C_2$-$C_4$ alkynylene group.

Additionally or alternatively, each $Z^5$ can be a $C_1$-$C_2$ alkoxy group; each $Z^6$ and $Z^7$ independently can be a $C_1$-$C_2$ alkoxy group or a $C_1$-$C_2$ alkyl group; and each R can be a $C_2$-$C_4$ alkylene group, a $C_2$-$C_4$ alkenylene group or a $C_2$-$C_4$ alkynylene group.

Additionally or alternatively, each R can be a nitrogen-containing $C_2$-$C_{10}$ alkylene group, a nitrogen-containing $C_3$-$C_{10}$ alkylene group, a nitrogen-containing $C_4$-$C_{10}$ alkylene group, a nitrogen-containing $C_4$-$C_9$ alkylene group, a nitrogen-containing $C_4$-$C_8$ alkylene group, or nitrogen containing $C_3$-$C_8$ alkylene group. The aforementioned nitrogen-containing alkylene groups may have one or more nitrogen atoms (e.g., 2, 3, etc.). Examples of nitrogen-containing alkylene groups include, but are not limited to,

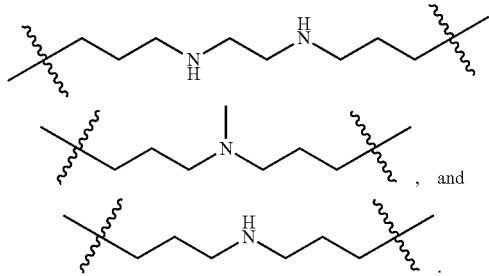

, and

.

Additionally or alternatively, each $Z^5$ can be a $C_1$-$C_2$ alkoxy group; each $Z^6$ and $Z^7$ independently can be a $C_1$-$C_2$ alkoxy group or a $C_1$-$C_2$ alkyl group; and each R can be a nitrogen-containing $C_4$-$C_{10}$ alkylene group.

Additionally or alternatively, each $Z^5$ can be a $C_1$-$C_2$ alkoxy group; each $Z^6$ and $Z^7$ independently can be a $C_1$-$C_2$ alkoxy group or a $C_1$-$C_2$ alkyl group; and each R can be a $C_2$-$C_4$ alkylene group, a $C_2$-$C_4$ alkenylene group, a $C_2$-$C_4$ alkynylene group or a nitrogen-containing $C_4$-$C_{10}$ alkylene group.

Additionally or alternatively, each R can be an optionally substituted $C_6$-$C_{20}$ aralkyl, an optionally substituted $C_6$-$C_{14}$ aralkyl, or an optionally substituted $C_6$-$C_{10}$ aralkyl. Examples of $C_6$-$C_{20}$ aralkyls include, but are not limited to, phenymethyl, phenylethyl, and naphthylmethyl. The aralkyl may be optionally substituted with a $C_1$-$C_6$ alkyl group, particularly a $C_1$-$C_4$ alkyl group.

Additionally or alternatively, each $Z^5$ can be a $C_1$-$C_2$ alkoxy group; each $Z^6$ and $Z^7$ independently can be a $C_1$-$C_2$ alkoxy group or a $C_1$-$C_2$ alkyl group; and each R can be an optionally substituted $C_6$-$C_{10}$ aralkyl.

Additionally or alternatively, each $Z^5$ can be a $C_1$-$C_2$ alkoxy group; each $Z^6$ and $Z^7$ independently can be a $C_1$-$C_2$ alkoxy group or a $C_1$-$C_2$ alkyl group; and each R can be a $C_2$-$C_4$ alkylene group, a $C_2$-$C_4$ alkenylene group, a $C_2$-$C_4$ alkynylene group, a nitrogen-containing $C_4$-$C_{10}$ alkylene group, or an optionally substituted $C_6$-$C_{10}$ aralkyl.

Additionally or alternatively, each R can be an optionally substituted $C_4$-$C_{20}$ heterocycloalkyl group, an optionally substituted $C_4$-$C_{16}$ heterocycloalkyl group, an optionally substituted $C_4$-$C_{12}$ heterocycloalkyl group, or an optionally substituted $C_4$-$C_{10}$ heterocycloalkyl group. Examples of $C_4$-$C_{20}$ heterocycloalkyl groups include, but are not limited to, thienylmethyl, furylethyl, pyrrolylmethyl, piperazinylethyl, pyridylmethyl, benzoxazolylethyl, quinolinylpropyl, and imidazolylpropyl. The heterocycloalkyl may be optionally substituted with a $C_1$-$C_6$ alkyl group, particularly a $C_1$-$C_4$ alkyl group.

Additionally or alternatively, each $Z^5$ can be a $C_1$-$C_2$ alkoxy group; each $Z^6$ and $Z^7$ independently can be a $C_1$-$C_2$ alkoxy group or a $C_1$-$C_2$ alkyl group; and each R can be an optionally substituted $C_4$-$C_{12}$ heterocycloalkyl group.

Additionally or alternatively, each $Z^5$ can be a hydroxyl group, a $C_1$-$C_2$ alkoxy group or an oxygen atom bonded to a silicon atom or another compound; each $Z^6$ and $Z^7$ independently can be a hydroxyl group, a $C_1$-$C_2$ alkoxy group or a $C_1$-$C_2$ alkyl group or an oxygen atom bonded to a silicon atom or another compound; and each R can be a $C_2$-$C_4$ alkylene group, a $C_2$-$C_4$ alkenylene group, a $C_2$-$C_4$ alkynylene group, a nitrogen-containing $C_4$-$C_{10}$ alkylene group, an optionally substituted $C_6$-$C_{10}$ aralkyl, or an optionally substituted $C_4$-$C_{12}$ heterocycloalkyl group.

Additionally or alternatively, each $Z^5$ can be a $C_1$-$C_2$ alkoxy group; each $Z^6$ and $Z^7$ independently can be a $C_1$-$C_2$ alkoxy group or a $C_1$-$C_2$ alkyl group; and each R can be a $C_2$-$C_4$ alkylene group, a $C_2$-$C_4$ alkenylene group, a $C_2$-$C_4$ alkynylene group, a nitrogen-containing $C_4$-$C_{10}$ alkylene group, an optionally substituted $C_6$-$C_{10}$ aralkyl, or an optionally substituted $C_4$-$C_{12}$ heterocycloalkyl group.

In a particular embodiment, each $Z^5$ and $Z^6$ can be ethoxy, each $Z^7$ can be methyl and each R can be —$CH_2CH_2$—, such that compound corresponding to Formula (III) can be 1,2-bis(methyldiethoxysilyl)ethane ($CH_3$ $(EtO)_2Si$—$CH_2CH_2$—$Si(EtO)_2CH_3$).

In a particular embodiment, each $Z^5$, $Z^6$ and $Z^7$ can be ethoxy and each R can be —$CH_2$—, such that compound corresponding to Formula (III) can be bis(triethoxysilyl)methane (($EtO)_3Si$—$CH_2$—$Si(EtO)_3$).

In a particular embodiment, each $Z^5$, $Z^6$ and $Z^7$ can be ethoxy and each R can be
—HC=CH—, such that compound corresponding to Formula (III) can be 1,2-bis(triethoxysilyl)ethylene (($EtO)_3Si$—HC=CH—$Si(EtO)_3$).

In a particular embodiment, each $Z^5$, $Z^6$ and $Z^7$ can be methoxy and each R can be

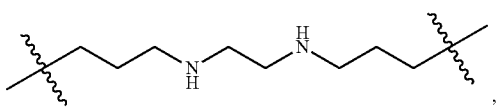 [SMILES: *CCCNCCNCCC*], such that compound corresponding to Formula (III) can be N,N'-bis[(3-trimethoxysilyl)propyl]ethylenediamine.

In a particular embodiment, each $Z^5$ and $Z^6$ can be ethoxy, each $Z^7$ can be methyl and each R can be

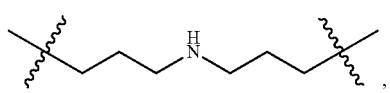 [SMILES: *CCCNCCC*], such that compound corresponding to Formula (III) can be bis[(methyldiethoxysilyl)propyl]amine.

In a particular embodiment, each $Z^5$ and $Z^6$ can be methoxy, each $Z^7$ can be methyl and each R can be

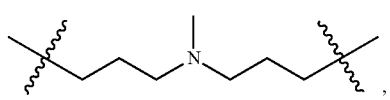 [SMILES: *CCCN(C)CCC*], such that compound corresponding to Formula (III) can be bis[(methyldimethoxysilyl)propyl]-N-methylamine.

The molar ratio of compound of Formula (Ia) to compound of Formula (III) may vary within wide limits, such as from about 99:1 to about 1:99, from about 1:5 to about 5:1, from about 4:1 to about 1:4 or from about 3:2 to about 2:3. For example, a molar ratio of compound of Formula (Ia) to compound of Formula (III) can be from about 4:1 to about 1:4 or from about 2.5:1 to 1:2.5, about 2:1 to about 1:2, such as about 1.5:1 to about 1.5:1.

II.E. Trivalent Metal Oxide Sources

In additional embodiments, the methods provided herein can further comprise adding to the aqueous solution sources of a trivalent metal oxide.

Sources of trivalent metal oxides can include, but are not limited to, corresponding salts, alkoxides, oxides, and/or hydroxides of the trivalent metal, e.g., aluminum sulphate, aluminum nitrate, colloidal alumina, aluminum trihydroxide, hydroxylated alumina, $Al_2O_3$, aluminum halides (e.g., $AlCl_3$), $NaAlO_2$, boron nitride, $B_2O_3$ and/or $H_3BO_3$.

In various aspects, the source of trivalent metal oxide may be a compound of formula $M^1(OZ^8)_3$ (IV), wherein $M^1$ can be a Group 13 metal and each $Z^8$ independently can be a hydrogen atom, a $C_1$-$C_6$ alkyl group or a bond to a silicon atom of another compound.

In one embodiment, $M^1$ can be B, Al, Ga, In, Il, or Uut. In particular, $M^1$ can be Al or B.

Additionally or alternatively, each $Z^8$ can a hydrogen atom.

Additionally or alternatively, each $Z^8$ can be a $C_1$-$C_6$ alkyl group, a $C_1$-$C_5$ alkyl group, a $C_1$-$C_4$ alkyl group, a $C_1$-$C_3$ alkyl group, a $C_1$-$C_2$ alkyl group or methyl. In particular, each $Z^8$ can be methyl, ethyl, propyl or butyl.

Additionally or alternatively, each $Z^8$ can a bond to a silicon atom of another compound.

Additionally or alternatively, $M^1$ can be Al or B and each $Z^8$ can be, a hydrogen atom, methyl, ethyl, propyl butyl or a bond to a silicon atom of another compound.

Additionally or alternatively, $M^1$ can be Al or B and each $Z^8$ can be methyl, ethyl, propyl or butyl.

In a particular embodiment, $M^1$ can be Al and each $Z^8$ can be methyl, such that compound corresponding to Formula (IV) can be aluminum trimethoxide.

In a particular embodiment, $M^1$ can be Al and each $Z^8$ can be ethyl, such that compound corresponding to Formula (IV) can be aluminum triethoxide.

In a particular embodiment, $M^1$ can be Al and each $Z^8$ can be propyl, such that compound corresponding to Formula (IV) can be aluminum isopropoxide.

In a particular embodiment, $M^1$ can be Al and each $Z^8$ can be butyl, such that compound corresponding to Formula (IV) can be aluminum tri-sec-butoxide.

Additionally or alternatively, the source of trivalent metal oxide may be a compound of Formula $(Z^9O)_2M^2$—O—Si$(OZ^{10})_3$ (V), wherein $M^2$ can be a Group 13 metal and $Z^9$ and $Z^{10}$ each independently can be a hydrogen atom, a $C_1$-$C_6$ alkyl group or a bond to silicon atom of another compound.

In one embodiment, $M^2$ can be B, Al, Ga, In, Il, or Uut. In particular, $M^1$ can be Al or B.

Additionally or alternatively, $Z^9$ and $Z^{10}$ each independently can be a hydrogen atom.

Additionally or alternatively, $Z^9$ and $Z^{10}$ each independently can be a $C_1$-$C_6$ alkyl group, a $C_1$-$C_5$ alkyl group, a $C_1$-$C_4$ alkyl group, a $C_1$-$C_3$ alkyl group, a $C_1$-$C_2$ alkyl group or methyl. In particular, $Z^9$ and $Z^{10}$ each independently can be methyl, ethyl, propyl or butyl.

Additionally or alternatively, $Z^9$ and $Z^{10}$ each independently can be a bond to silicon atom of another compound.

Additionally or alternatively, $M^1$ can be Al or B and $Z^9$ and $Z^{10}$ each independently can be a hydrogen atom, methyl, ethyl, propyl, butyl or a bond to silicon atom of another compound.

Additionally or alternatively, $M^1$ can be Al or B and $Z^9$ and $Z^{10}$ each independently can be methyl, ethyl, propyl or butyl.

Additionally or alternatively, the source of a trivalent metal oxide may be a source of a compound of Formula (IV) (e.g., $AlCl_3$), and/or a source of a compound of Formula (V).

The molar ratio of compound of Formula (Ia) to trivalent metal oxide may vary within wide limits, such as from about 99:1 to about 1:99, from about 30:1 to about 1:1, from about 25:1 to about 1:1, from about 20:1 to about 3:1 or from about 20:1 to about 5:1.

II.F. Compounds of Formula (VI)

In additional embodiments, the methods provided herein can further comprise adding to the aqueous solution a compound of Formula at least one cyclic compound of Formula

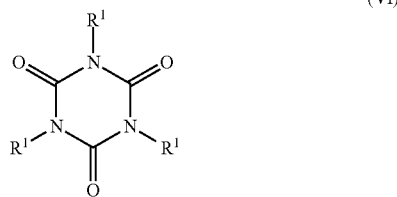

(VI)

into the aqueous mixture to form a solution, wherein each $R^1$ independently can be a $X^1OX^2X^3SiX^4$ group, wherein each $X^1$ can be a hydrogen atom, a $C_1$-$C_4$ alkyl group or a bond to a silicon atom of another compound; $X^2$ and $X^3$ each independently can be a hydroxyl group, a $C_1$-$C_4$ alkyl group, a $C_1$-$C_4$ alkoxy group or an oxygen atom bonded to a silicon atom of another compound; and each $X^4$ can be a $C_1$-$C_8$ alkylene group bonded to a nitrogen atom of the cyclic compound.

In various embodiments, each $X^1$ can be a hydrogen atom.

Additionally or alternatively, each $X^1$ can be a $C_1$-$C_4$ alkyl, a $C_1$-$C_3$ alkyl, a $C_1$-$C_2$ alkyl or methyl.

Additionally or alternatively, each $X^1$ can be a bond to a silicon atom of another compound.

Additionally or alternatively, each $X^2$ and $X^3$ each independently can be a hydroxyl group.

Additionally or alternatively, each $X^2$ and $X^3$ each independently can be a $C_1$-$C_4$ alkyl group, a $C_1$-$C_3$ alkyl group, a $C_1$-$C_2$ alkyl group or methyl.

Additionally or alternatively, each $X^2$ and $X^3$ each independently can be a $C_1$-$C_4$ alkoxy group, a $C_1$-$C_3$ alkoxy group, a $C_1$-$C_2$ alkoxy group or methoxy.

Additionally or alternatively, each $X^2$ and $X^3$ each independently can be a $C_1$-$C_2$ alkyl group or a $C_1$-$C_2$ alkoxy group.

Additionally or alternatively, each $X^2$ and $X^3$ each independently can be an oxygen atom bonded to a silicon atom of another compound.

Additionally or alternatively, each $X^1$ can be a hydrogen atom, a $C_1$-$C_2$ alkyl group or a bond to a silicon atom of another compound; and $X^2$ and $X^3$ each independently can be a hydroxyl group, a $C_1$-$C_2$ alkyl group, a $C_1$-$C_2$ alkoxy group or an oxygen atom bonded to a silicon atom of another compound.

Additionally or alternatively, each $X^1$ can be $C_1$-$C_2$ alkyl group; and $X^2$ and $X^3$ each independently can be a $C_1$-$C_2$ alkyl group or a $C_1$-$C_2$ alkoxy group.

Additionally or alternatively, each $X^4$ can be a $C_1$-$C_7$ alkylene group bonded to a nitrogen atom of the cyclic compound, a $C_1$-$C_7$ alkylene group bonded to a nitrogen atom of the cyclic compound, a $C_1$-$C_6$ alkylene group bonded to a nitrogen atom of the cyclic compound, a $C_1$-$C_4$ alkylene group bonded to a nitrogen atom of the cyclic compound, a $C_1$-$C_3$ alkylene group bonded to a nitrogen atom of the cyclic compound, a $C_1$-$C_2$ alkylene group bonded to a nitrogen atom of the cyclic compound, or —$CH_2$— bonded to a nitrogen atom of the cyclic compound.

Additionally or alternatively, each $X^1$ can be a hydrogen atom, a $C_1$-$C_2$ alkyl group or a bond to a silicon atom of another compound; $X^2$ and $X^3$ each independently can be a hydroxyl group, a $C_1$-$C_2$ alkyl group, a $C_1$-$C_2$ alkoxy group or an oxygen atom bonded to a silicon atom of another compound; and $X^4$ can be a $C_1$-$C_4$ alkylene group bonded to a nitrogen atom of the cyclic compound.

Additionally or alternatively, each $X^1$ can be a $C_1$-$C_2$ alkyl group; $X^2$ and $X^3$ each independently can be a $C_1$-$C_2$ alkyl group or a $C_1$-$C_2$ alkoxy group; and $X^4$ can be a $C_1$-$C_4$ alkylene group bonded to a nitrogen atom of the cyclic compound.

In a particular embodiment, each $X^1$ can be methyl; $X^2$ and $X^3$ each independently can be methoxy; and $X^4$ can be —$CH_2CH_2CH_2$—, such that the compound corresponding to Formula (Ia) can be tris(3-trimethoxysilylpropyl)isocyanurate.

In some embodiments, only a compound of Formula (VI) (e.g., tris(3-trimethoxysilylpropyl)isocyanurate) may be added to the aqueous mixture and no other compounds of Formulas (I)-(V) are added. Additionally or alternatively, only a compound of Formula (VI) (e.g., tris(3-trimethoxysilylpropyl)isocyanurate) and a compound of Formula (II) (e.g., tetraethyl orthosilicate (TEOS) $((EtO)_4Si)$ may be added to the aqueous mixture and no other compounds of Formulas (I) and (III)-(V) are added.

II. G. The Solution

In various embodiments, the solution may containing varying amounts of compounds of Formulas (Ia), (II), (III), (IV), (V) and/or (VI). For the example, the solution may contain Formulas (Ia), (II), (III), (IV), (V) and/or (VI) in an amount of about 1 wt. % to about 50 wt. %, about 1 wt. % to about 45 wt. %, about 1 wt. % to about 40 wt. %, about 1 wt. % to about 35 wt. %, about 1 wt. % to about 30 wt. %, about 1 wt. % to about 25 wt. %, about 1 wt. % to about 20 wt. %, about 1 wt. % to about 15 wt. %, about 1 wt. % to about 10 wt. %, about 1 wt. % to about 8 wt. %, about 1 wt. % to about 6 wt. %, about 4 wt. % to about 50 wt. %, about 4 wt. % to about 45 wt. %, about 4 wt. % to about 40 wt. %, about 4 wt. % to about 35 wt. %, about 4 wt. % to about 30 wt. %, about 4 wt. % to about 25 wt. %, about 4 wt. % to about 20 wt. %, about 4 wt. % to about 15 wt. %, about 4 wt. % to about 10 wt. %, about 4 wt. % to about 8 wt. %, about 4 wt. % to about 6 wt. %, or about 5 wt. % to about 6 wt. %. In particular, the solution may contain Formula (Ia) in an amount of about 1 wt. % to about 20 wt. % or about 4 wt. % to about 6 wt. %.

II.H. Metal Chelate Sources

In additional embodiments, the methods provided herein can further comprise adding to the aqueous solution a sources of metal chelate compounds.

Examples of metal chelate compounds, when present, can include titanium chelate compounds such as triethoxy.mono(acetylacetonato) titanium, tri-n-propoxy.mono(acetylacetonato)titanium, tri-i-propoxy.mono(acetylacetonato)titanium, tri-n-butoxy.mono(acetylacetonato)titanium, tri-sec-butoxy.mono(acetylacetonato)titanium, tri-t-butoxy.mono(acetylacetonato)titanium, diethoxy.bis(acetylacetonato)titanium, di-n-propoxy.bis(acetylacetonato)titanium, di-i-propoxy.bis(acetylacetonato)titanium, di-n-butoxy.bis(acetylacetonato)titanium, di-sec-butoxy.bis(acetylacetonato)titanium, di-t-butoxy.bis(acetylacetonato)titanium, monoethoxy.tris(acetylacetonato)titanium, mono-n-propoxy.tris(acetylacetonato) titanium, mono-i-propoxy.tris(acetylacetonato)titanium, mono-n-butoxy. tris(acetylacetonato)titanium, mono-sec-butoxy.tris(acetylacetonato)titanium, mono-t-butoxy-tris(acetylacetonato)titanium, tetrakis(acetylacetonato)titanium, triethoxy. mono(ethylacetoacetaato)titanium, tri-n-propoxy.mono(ethylacetoacetato)titanium, tri-i-propoxy.mono(ethylacetoacetato) titanium, tri-n-butoxy.mono(ethylacetoacetato) titanium, tri-sec-butoxy.mono(ethylacetoacetato) titanium, tri-t-butoxy-mono(ethylacetoacetato)titanium, diethoxy.bis(ethylacetoacetato)titanium, di-n-propoxy.bis(ethylacetoacetato)titanium, di-i-propoxy.bis(ethylacetoacetato)titanium, di-n-butoxy.bis(ethylacetoacetato)titanium, di-sec-butoxy.bis(ethylacetoacetato)titanium, di-t-butoxy.bis(ethylacetoacetato)titanium, monoethoxy.tris(ethylacetoacetato)titanium, mono-n-propoxy.tris(ethylacetoaetato)titanium, mono-i-propoxy.tris(ethylacetoacetato) titanium, mono-n-butoxy.tris(ethylacetoacetato)titanium, mono-sec-butoxy. tris(ethylacetoacetato)titanium, mono-t-butoxy.tris(ethylacetoacetato)titanium, tetrakis(ethylacetoacetato) titanium, mono(acetylacetonato)tris(ethylacetoacetato) titanium, bis(acetylacetonato)bis(ethylacetoacetato)titanium, and tris(acetylacetonato)mono(ethylacetoacetato)titanium; zirconium chelate compounds such as triethoxy.mono(acetylacetonato)zirconium, tri-n-propoxy.mono(acetylacetonato) zirconium, tri-i-propoxy.mono(acetylacetonato)zirconium, tri-n-butoxy. mono(acetylacetonato)zirconium, tri-sec-butoxy.mono(acetylacetonato)zirconium, tri-t-butoxy.mono(acetylacetonato)zirconium, diethoxy.bis(acetylacetonato) zirconium, di-n-propoxy.bis(acetylacetonato)zirconium, di-i-propoxy.bis(acetylacetonato)zirconium, di-n-butoxy.bis(acetylacetonato)zirconium, di-sec-butoxy.bis(acetylacetonato)zirconium, di-t-butoxy.bis(acetylacetonato)zirconium, monoethoxy.tris(acetylacetonato)zirconium, mono-n-propoxy.tris(acetylacetonato)zirconium, mono-i-propoxy.tris(acetylacetonato) zirconium, mono-n-butoxy.tris(acetylacetonato)zirconium, mono-sec-butoxy. tris(acetylacetonato)zirconium, mono-t-butoxy.tris(acetylacetonato)zirconium, tetrakis(acetylacetonato) zirconium, triethoxy.mono(ethylacetoacetato)zirconium, tri-n-propoxy.mono(ethylacetoacetato)zirconium, tri-i-propoxy.mono(ethylacetoacetato) zirconium, tri-n-butoxy.mono(ethylacetoacetato)zirconium, tri-sec-butoxy. mono(ethylacetoacetato)zirconium, tri-t-butoxy.mono(ethylacetoacetato)zirconium, diethoxy.bis(ethylacetoacetato)zirconium, di-n-propoxy.bis(ethylacetoacetato)zirconium, di-i-propoxy.bis(ethylacetoacetato)zirconium, di-n-butoxy.bis(ethylacetoacetato) zirconium, di-sec-butoxy.bis(ethylacetoacetato)zirconium, di-t-butoxy. bis(ethylacetoacetato)zirconium, monoethoxy.tris(ethylacetoacetato)zirconium, mono-n-propoxy.tris(ethylacetoacetato)zirconium, mono-i-propoxy.tris(ethylacetoacetato) zirconium, mono-n-butoxy.tris(ethylacetoacetato)zirconium, mono-sec-butoxy. tris(ethylacetoacetato)zirconium, mono-t-butoxy.tris(ethylacetoacetato)zirconium, tetrakis(ethylacetoacetato)zirconium, mono(acetylacetonato)tris(ethylacetoacetato) zirconium, bis(acetylacetonato)bis(ethylacetoacetato)zirconium, and tris(acetylacetonato)mono(ethylacetoacetato)zirconium; and aluminum chelate compounds such as tris(acetylacetonato)aluminum and tris(ethylacetoacetato)aluminum. Of these, the chelate compounds of titanium or aluminum can be of note, of which the chelate compounds of titanium can be particularly of note. These metal chelate compounds may be used either singly or in combination II.I. Molar Ratio In the methods described herein, a molar ratio of Formula (Ia): Formula (Ia), Formula (Ia): Formula (II), Formula (Ia): Formula (III), Formula (III): Formula (II), Formula (Ia): Formula (IV), Formula (Ia): Formula (V); Formula (VI):(II) and Formula (Ia): Formula (VI) of about 99:1 to about 1:99, about 75:1 to about 1:99, about 50:1 to about 1:99, about 25:1 to about 1:99, about 15:1 to about 1:99, about 50:1 to about 1:50, about 25:1 to about 1:25 or about 15:1 to about 1:15 may be used. For example, molar ratios of about 3:2, about 4:1, about 4:3, about 5:1, about 2:3, about 1:1 5:2 and about 15:1 may be used. For example, a molar ratio of Formula (Ia): Formula (Ia) can be about 3:2. A molar ratio of Formula (Ia): Formula (II) can be about 2:3, about 4:3, about 4:1 or about 3:2. A molar ratio of Formula (Ia): Formula (III) can be about 2:3, and about 4:1. A molar ratio of Formula (III): Formula (II) can be about 5:2, about 1:1, about 1:2 or about 2:3. A molar ratio of Formula (Ia): Formula (IV) and Formula (Ia): Formula (V) can be about 15:1 or about 5:1. A molar ratio of Formula (Ia): Formula (VI) can be about 3:2. A molar ratio of Formula (VI): Formula (II) can be about 2:3.

For the sake of the following discussion, the compounds of Formula (Ia), (II) and (III) shall be referred to collectively as starting siloxane. Depending on the choice of starting materials, the solution may have a variety of compositions. For example, if base is used, the solution may have molar ratios of starting siloxane to $OH^-$ of from about 1:5 to about 1:20, such as from about 1:5 to about 1:15 or from about 1:5 to 1:10, or from about 1:6 to 1:20. If acid is used, the solution may have molar ratios of starting siloxane:$H^+$ of from about 50:1 to about 5:1, such as from about 45:1 to about 10:1. In both cases when acid or base is used, the molar ratios of starting siloxane to $H_2O$ may vary from about 1:50 to about 1:1000, such as from about 1:100 to about 1:500.

II.J. Coating the Support

The methods described herein can further comprise coating the solution onto a support to form a coated support. The coating may comprise any suitable method such as mounting the support (e.g., on a spin-coater) and pouring the solution onto the support. Examples of supports include, but are not limited to, a ceramic support (e.g. $TiO_2$), a polymer support, a mixed-matrix support, a metallic support, a silica support, a carbon support, a liquid/facilitated transport support, a zeolite support and combinations thereof. In particular the support may be a ceramic support, a carbon support or a metallic support. In a particular embodiment, the support is a zeolite support.

II.K. Aging the Coated Support

The coated support formed in the methods described herein can be aged for at least about 4 hours, at least about 6 hours, at least about 12 hours, at least about 18 hours, at least about 24 hours (1 day), at least about 30 hours, at least about 36 hours, at least about 42 hours, at least about 48 hours (2 days), at least about 54 hours, at least about 60 hours, at least about 66 hours, at least about 72 hours (3 days), at least about 96 hours (4 days), at least about 120 hours (5 days) or at least about 144 hours (6 days). In particular, the slurry can be aged for up to about 24 hours.

Additionally or alternatively, the coated support formed in the methods described herein can be aged for about 4 hours to about 144 hours (6 days), about 4 hours to about 120 hours (5 days), about 4 hours to about 96 hours (4 days), about 4 hours to about 72 hours (3 days), about 4 hours to about 66 hours, about 4 hours to about 60 hours, about 4 hours to about 54 hours, about 4 hours to about 48 hours (2 days), about 4 hours to about 42 hours, about 4 hours to about 36 hours, about 4 hours to about 30 hours, about 4 hours to about 24 hours (1 day), about 4 hours to about 18 hours, about 4 hours to about 12 hours, about 4 hours to about 6 hours, about 6 hours to about 144 hours (6 days), about 6 hours to about 120 hours (5 days), about 6 hours to about 96 hours (4 days), about 6 hours to about 72 hours (3 days), about 6 hours to about 66 hours, about 6 hours to about 60 hours, about 6 hours to about 54 hours, about 6 hours to about 48 hours (2 days), about 6 hours to about 42 hours, about 6 hours to about 36 hours, about 6 hours to about 30 hours, about 6 hours to about 24 hours (1 day), about 6 hours to about 18 hours, about 6 hours to about 12 hours, about 12 hours to about 144 hours (6 days), about 12 hours to about 120 hours (5 days), about 12 hours to about 96 hours (4 days), about 12 hours to about 72 hours (3 days), about 12 hours to about 66 hours, about 12 hours to about 60 hours, about 12 hours to about 54 hours, about 12 hours to about 48 hours (2 days), about 12 hours to about 42 hours, about 12 hours to about 36 hours, about 12 hours to about 30 hours, about 12 hours to about 24 hours (1 day), about 12 hours to about 18 hours, about 18 hours to about 144 hours (6 days), about 18 hours to about 120 hours (5 days), about 18 hours to about 96 hours (4 days), about 18 hours to about 72 hours (3 days), about 18 hours to about 66 hours, about 18 hours to about 60 hours, about 18 hours to about 54 hours, about 18 hours to about 48 hours (2 days), about 18 hours to about 42 hours, about 18 hours to about 36 hours, about 18 hours to about 30 hours, about 18 hours to about 24 hours (1 day), about 24 hours (1 day) to about 144 hours (6 days), about 24 (1 day) hours (1 day) to about 120 hours (5 days), about 24 hours (1 day) to about 96 hours (4 days), about 24 hours (1 day) to about 72 hours (3 days), about 24 hours (1 day) to about 66 hours, about 24 hours (1 day) to about 60 hours, about 24 hours (1 day) to about 54 hours, about 24 hours (1 day) to about 48 hours (2 days), about 24 hours (1 day) to about 42 hours, about 24 hours (1 day) to about 36 hours, about 24 hours (1 day) to about 30 hours, about 30 hours to about 144 hours (6 days), about 30 hours to about 120 hours (5 days), about 30 hours to about 96 hours (4 days), about 30 hours to about 72 hours (3 days), about 30 hours to about 66 hours, about 30 hours to about 60 hours, about 30 hours to about 54 hours, about 30 hours to about 48 hours (2 days), about 30 hours to about 42 hours, about 30 hours to about 36 hours, about 36 hours to about 144 hours (6 days), about 36 hours to about 120 hours (5 days), about 36 hours to about 96 hours (4 days), about 36 hours to about 72 hours (3 days), about 36 hours to about 66 hours, about 36 hours to about 60 hours, about 36 hours to about 54 hours, about 36 hours to about 48 hours (2 days), about 36 hours to about 42 hours, about 42 hours to about 144 hours (6 days), about 42 hours to about 120 hours (5 days), about 42 hours to about 96 hours (4 days), about 42 hours to about 72 hours (3 days), about 42 hours to about 66 hours, about 42 hours to about 60 hours, about 42 hours to about 54 hours, about 42 hours to about 48 hours (2 days), about 48 hours (2 days) to about 144 hours (6 days), about 48 hours (2 days) to about 120 hours (5 days), about 48 hours (2 days) to about 96 hours (4 days), about 48 hours (2 days) to about 72 hours (3 days), about 48 hours (2 days) to about 66 hours, about 48 hours (2 days) to about 60 hours, about 48 hours (2 days) to about 54 hours, about 54 hours to about 144 hours (6 days), about 54 hours to about 120 hours (5 days), about 54 hours to about 96 hours (4 days), about 54 hours to about 72 hours (3 days), about 54 hours to about 66 hours, about 54 hours to about 60 hours, about 60 hours to about 144 hours (6 days), about 60 hours to about 120 hours (5 days), about 60 hours to about 96 hours (4 days), about 60 hours to about 72 hours (3 days), about 60 hours to about 66 hours, about 66 hours to about 144 hours (6 days), about 66 hours to about 120 hours (5 days), about 66 hours to about 96 hours (4 days), about 66 hours to about 72 hours (3 days), about 72 hours (3 days) to about 144 hours (6 days), about 72 hours (3 days) to about 120 hours (5 days), about 72 hours (3 days) to about 96 hours (4 days), about 96 hours (4 days) to about 144 hours (6 days), about 96 hours (4 days) to about 120 hours (5 days), or about 120 hours (5 days) to about 144 hours (6 days).

Additionally or alternatively, the coated support formed in the method can be aged at temperature of at least about 10° C., at least about 20° C., at least about 30° C., at least about 40° C., at least about 50° C., at least about 60° C., at least about 70° C., at least about 80° C., at least about 90° C., at least about 100° C., at least about 110° C., at least about 120° C., at least about 125° C. at least about 130° C., at least about 140° C., at least about 150° C., at least about 175° C., at least about 200° C., at least about 250° C., or about 300° C.

Additionally or alternatively, the coated support formed in the method can be aged at temperature of about 10° C. to about 300° C., about 10° C. to about 250° C., about 10° C. to about 200° C., about 10° C. to about 175° C., about 10° C. to about 150° C., about 10° C. to about 140° C., about 10° C. to about 130° C., about 10° C. to about 120° C., about 10° C. to about 110° C., about 10° C. to about 100° C., about 10° C. to about 90° C., about 10° C. to about 80° C., about 10° C. to about 70° C., about 10° C. to about 60° C., about 10° C. to about 50° C., about 20° C. to about 300° C., about 20° C. to about 250° C., about 20° C. to about 200° C., about 20° C. to about 175° C., about 20° C. to about 150° C., about 20° C. to about 140° C., about 20° C. to about 130° C., about 20° C. to about 125° C., about 20° C. to about 120° C., about 20° C. to about 110° C., about 20° C. to about 100° C., about 20° C. to about 90° C., about 20° C. to about 80° C., about 20° C. to about 70° C., about 20° C. to about 60° C., about 20° C. to about 50° C., about 30° C. to about 300° C., about 30° C. to about 250° C., about 30° C. to about 200° C., about 30° C. to about 175° C., about 30° C. to about 150° C., about 30° C. to about 140° C., about 30° C. to about 130° C., about 30° C. to about 125° C., about 30° C. to about 120° C., about 30° C. to about 110° C., about 30° C. to about 100° C., about 30° C. to about 90° C., about 30° C. to about 80° C., about 30° C. to about 70° C., about 30° C. to about 60° C., about 30° C. to about 50° C., about 50° C. to about 300° C., about 50° C. to about 250° C., about 50° C. to about 200° C., about 50° C. to about 175° C., about 50° C. to about 150° C., about 50° C. to about 140° C., about 50° C. to about 130° C., about 50° C. to about 125° C., about 50° C. to about 120° C., about 50° C. to about 110° C., about 50° C. to about 100° C., about 50° C. to about 90° C., about 50° C. to about 80° C., about 50° C. to about 70° C., about 50° C. to about 60° C., about 70°

C. to about 300° C., about 70° C. to about 250° C., about 70° C. to about 200° C., about 70° C. to about 175° C., about 70° C. to about 150° C., about 70° C. to about 140° C., about 70° C. to about 130° C., about 70° C. to about 125° C., about 70° C. to about 120° C., about 70° C. to about 110° C., about 70° C. to about 100° C., about 70° C. to about 90° C., about 70° C. to about 80° C., about 80° C. to about 300° C., about 80° C. to about 250° C., about 80° C. to about 200° C., about 80° C. to about 175° C., about 80° C. to about 150° C., about 80° C. to about 140° C., about 80° C. to about 130° C., about 80° C. to about 125° C., about 80° C. to about 120° C., about 80° C. to about 110° C., about 80° C. to about 100° C., about 80° C. to about 90° C., about 90° C. to about 300° C., about 90° C. to about 250° C., about 90° C. to about 200° C., about 90° C. to about 175° C., about 90° C. to about 150° C., about 90° C. to about 140° C., about 90° C. to about 130° C., about 90° C. to about 125° C., about 90° C. to about 120° C., about 90° C. to about 110° C., about 90° C. to about 100° C., about 100° C. to about 300° C., about 100° C. to about 250° C., about 100° C. to about 200° C., about 100° C. to about 175° C., about 100° C. to about 150° C., about 100° C. to about 140° C., about 100° C. to about 130° C., about 100° C. to about 120° C., about 100° C. to about 110° C., about 110° C. to about 300° C., about 110° C. to about 250° C., about 110° C. to about 200° C., about 110° C. to about 175° C., about 110° C. to about 150° C., about 110° C. to about 140° C., about 110° C. to about 130° C., about 110° C. to about 120° C., about 120° C. to about 300° C., about 120° C. to about 250° C., about 120° C. to about 200° C., about 120° C. to about 175° C., about 120° C. to about 150° C., about 120° C. to about 140° C., about 120° C. to about 130° C., about 130° C. to about 300° C., about 130° C. to about 250° C., about 130° C. to about 200° C., about 130° C. to about 175° C., about 130° C. to about 150° C., or about 130° C. to about 140° C.

In particular, the coated support is aged for the amount of time described above (e.g., up to about 144 hours, etc.) at a temperature of about 20° C. to about 200° C.

Additionally or alternatively, the coated support may be aged in the presence of water, e.g., in a humidified chamber.

II.L. Drying the Coated Support

The methods described herein comprise drying the coated support to obtain a membrane comprising an organosilica material which is a polymer comprising independent units of Formula $[Z^3Z^4SiCH_2]_3$ (I), wherein each $Z^3$ represents a hydroxyl group, a $C_1$-$C_4$ alkoxy group or an oxygen atom bonded to a silicon atom of another unit and each $Z^4$ represents a hydroxyl group, a $C_1$-$C_4$ alkoxy group, a $C_1$-$C_4$ alkyl group, an oxygen atom bonded to a silicon atom of another unit or an active site on the support.

In some embodiments, the coated support formed in the method can be dried at a temperature of greater than or equal to about 15° C., greater than or equal to about 25° C., greater than or equal to about 50° C., greater than or equal to about 70° C., greater than or equal to about 80° C., greater than or equal to about 100° C., greater than or equal to about 110° C., greater than or equal to about 120° C., greater than or equal to about 150° C., greater than or equal to about 200° C., greater than or equal to about 250° C., greater than or equal to about 300° C., greater than or equal to about 350° C., greater than or equal to about 400° C., greater than or equal to about 450° C., greater than or equal to about 500° C., greater than or equal to about 550° C., or greater than or equal to about 600° C.

Additionally or alternatively, the coated support formed in the method can be dried at temperature of about 15° C. to about 600° C., about 15° C. to about 550° C., about 15° C. to about 500° C., about 15° C. to about 450° C., about 15° C. to about 400° C., about 15° C. to about 350° C., about 15° C. to about 300° C., about 15° C. to about 250° C., about 15° C. to about 200° C., about 15° C. to about 150° C., about 15° C. to about 120° C., about 15° C. to about 110° C., about 15° C. to about 100° C., about 15° C. to about 80° C., about 15° C. to about 70° C., 25° C. to about 600° C., about 25° C. to about 550° C., about 25° C. to about 500° C., about 25° C. to about 450° C., about 25° C. to about 400° C., about 25° C. to about 350° C., about 25° C. to about 300° C., about 25° C. to about 250° C., about 25° C. to about 200° C., about 25° C. to about 150° C., about 25° C. to about 120° C., about 25° C. to about 110° C., about 25° C. to about 100° C., about 25° C. to about 80° C., about 25° C. to about 70° C., about 50° C. to about 600° C., about 50° C. to about 550° C., about 50° C. to about 500° C., about 50° C. to about 450° C., about 50° C. to about 400° C., about 50° C. to about 350° C., about 50° C. to about 300° C., about 50° C. to about 250° C., about 50° C. to about 200° C., about 50° C. to about 150° C., about 50° C. to about 120° C., about 50° C. to about 110° C., about 50° C. to about 100° C., about 50° C. to about 80° C., about 50° C. to about 70° C., about 70° C. to about 600° C., about 70° C. to about 550° C., about 70° C. to about 500° C., about 70° C. to about 450° C., about 70° C. to about 400° C., about 70° C. to about 350° C., about 70° C. to about 300° C., about 70° C. to about 250° C., about 70° C. to about 200° C., about 70° C. to about 150° C., about 70° C. to about 120° C., about 70° C. to about 100° C., about 70° C. to about 80° C., about 80° C. to about 600° C., about 70° C. to about 550° C., about 80° C. to about 500° C., about 80° C. to about 450° C., about 80° C. to about 400° C., about 80° C. to about 350° C., about 80° C. to about 300° C., about 80° C. to about 250° C., about 80° C. to about 200° C., about 80° C. to about 150° C., about 80° C. to about 120° C., about 80° C. to about 110° C., or about 80° C. to about 100° C.

In a particular embodiment, the coated supported formed in the method can be dried at temperature from about 15° C. to about 200° C.

Additionally or alternatively, the coated supported formed in the method can be dried under a vacuum, in an oven, in an inert atmosphere (e.g., $N_2$, Ar), in a reducing atmosphere and/or in an air atmosphere.

In various aspects, the membrane on the support may have thickness of up to about 0.005 µm, up to about 0.006 µm, up to about 0.008 µm, up to about 0.01 µm, up to about 0.02 µm, up to about 0.04 µm, up to about 0.05 µm, up to about 0.06 µm, up to about 0.08 µm, up to about 0.1 µm, up to about 0.2 µm, up to about 0.4 µm, up to about 0.5 µm, up to about 0.6 µm, up to about 0.8 µm, up to about 0.9 µm, up to about 1 µm, up to about 2 µm, up to about 5 µm, up to about 10 µm, or up to about 20 µm. In particular, the coating on the support may have thickness of up to about 1 µm.

Additionally or alternatively, the membrane on the support may have thickness of about 0.005 µm to about 20 µm, about 0.005 µm to about 10 µm, about 0.005 µm to about 5 µm, about 0.005 µm to about 1 µm, about 0.01 µm to about 20 µm, about 0.01 µm to about 10 µm, about 0.01 µm to about 5 µm, about 0.01 µm to about 1 µm, about 0.05 µm to about 20 µm, about 0.05 µm to about 10 µm, about 0.05 µm to about 5 µm or about 0.05 µm to about 1 µm.

II.M. Optional Further Steps

In some embodiments, the method can further comprise calcining the organosilica material and/or membrane to obtain a silica material. The calcining can be performed in air or an inert gas, such as nitrogen or air enriched in nitrogen. Calcining can take place at a temperature of at least about 300° C., at least about 350° C., at least about 400° C., at least about 450° C., at least about 500° C., at least about 550° C., at least about 600° C., or at least about 650° C., for example at least about 400° C. Additionally or alternatively, calcining can be performed at a temperature of about 300° C. to about 650° C., about 300° C. to about 600° C., about 300° C. to about 550° C., about 300° C. to about 400° C., about 300° C. to about 450° C., about 300° C. to about 400° C., about 300° C. to about 350° C., about 350° C. to about 650° C., about 350° C. to about 600° C., about 350° C. to about 550° C., about 350° C. to about 400° C., about 350° C. to about 450° C., about 350° C. to about 400° C., about 400° C. to about 650° C., about 400° C. to about 600° C., about 400° C. to about 550° C., about 400° C. to about 500° C., about 400° C. to about 450° C., about 450° C. to about 650° C., about 450° C. to about 600° C., about 450° C. to about 550° C., about 450° C. to about 500° C., about 500° C. to about 650° C., about 500° C. to about 600° C., about 500° C. to about 550° C., about 550° C. to about 650° C., about 550° C. to about 600° C. or about 600° C. to about 650° C.

Additionally or alternatively, the method as described herein may not include a calcining step.

In some embodiments, the method can further comprise incorporating a catalyst metal within the pores of the organosilica material and/or the support material. Exemplary catalyst metals can include, but are not limited to, a Group 6 element, a Group 8 element, a Group 9 element, a Group 10 element or a combination thereof. Exemplary Group 6 elements can include, but are not limited to, chromium, molybdenum, and/or tungsten, particularly including molybdenum and/or tungsten. Exemplary Group 8 elements can include, but are not limited to, iron, ruthenium, and/or osmium. Exemplary Group 9 elements can include, but are not limited to, cobalt, rhodium, and/or iridium, particularly including cobalt. Exemplary Group 10 elements can include, but are not limited to, nickel, palladium and/or platinum.

The catalyst metal can be incorporated into the organosilica material and/or support material by any convenient method, such as by impregnation, by ion exchange, or by complexation to surface sites. The catalyst metal so incorporated may be employed to promote any one of a number of catalytic tranformations commonly conducted in petroleum refining or petrochemicals production. Examples of such catalytic processes can include, but are not limited to, hydrogenation, dehydrogenation, aromatization, aromatic saturation, hydrodesulfurization, olefin oligomerization, polymerization, hydrodenitrogenation, hydrocracking, naphtha reforming, paraffin isomerization, aromatic transalkylation, saturation of double/triple bonds, and the like, as well as combinations thereof.

Thus, in another embodiment, a catalyst material comprising the organosilica material described herein is provided. The catalyst material may optionally comprise a binder or be self-bound. Suitable binders, include but are not limited to active and inactive materials, synthetic or naturally occurring zeolites, as well as inorganic materials such as clays and/or oxides such as silica, alumina, zirconia, titania, silica-alumina, cerium oxide, magnesium oxide, or combinations thereof. In particular, the binder may be silica-alumina, alumina and/or a zeolite, particularly alumina. Silica-alumina may be either naturally occurring or in the form of gelatinous precipitates or gels including mixtures of silica and metal oxides. It should be noted it is recognized herein that the use of a material in conjunction with a zeolite binder material, i.e., combined therewith or present during its synthesis, which itself is catalytically active may change the conversion and/or selectivity of the finished catalyst. It is also recognized herein that inactive materials can suitably serve as diluents to control the amount of conversion if the present invention is employed in alkylation processes so that alkylation products can be obtained economically and orderly without employing other means for controlling the rate of reaction. These inactive materials may be incorporated into naturally occurring clays, e.g., bentonite and kaolin, to improve the crush strength of the catalyst under commercial operating conditions and function as binders or matrices for the catalyst. The catalysts described herein typically can comprise, in a composited form, a ratio of support material to binder material ranging from about 80 parts support material to 20 parts binder material to 20 parts support material to 80 parts binder material, all ratios being by weight, typically from 80:20 to 50:50 support material: binder material, prefer ably from 65:35 to 35:65. Compositing may be done by conventional means including mulling the materials together followed by extrusion of pelletizing into the desired finished catalyst particles.

In some embodiments, the method can further comprise incorporating cationic metal sites into the network structure of the organosilica material and/or the support material by any convenient method, such as impregnation or complexation to the surface, through an organic precursor, or by some other method. This organometallic material may be employed in a number of hydrocarbon separations conducted in petroleum refining or petrochemicals production. Examples of such compounds to be desirably separated from petrochemicals/fuels can include olefins, paraffins, aromatics, and the like.

Additionally or alternatively, the method can further comprise incorporating a surface metal within the pores of the organosilica material and/or the support material. The surface metal can be selected from a Group 1 element, a Group 2 element, a Group 13 element, and a combination thereof. When a Group 1 element is present, it can preferably comprise or be sodium and/or potassium. When a Group 2 element is present, it can include, but may not be limited to, magnesium and/or calcium. When a Group 13 element is present, it can include, but may not be limited to, boron and/or aluminum.

One or more of the Group 1, 2, 6, 8-10 and/or 13 elements may be present on an exterior and/or interior surface of the organosilica material and/or support material. For example, one or more of the Group 1, 2 and/or 13 elements may be present in a first layer on the organosilica material and one or more of the Group 6, 8, 9 and/or 10 elements may be present in a second layer, e.g., at least partially atop the Group 1, 2 and/or 13 elements. Additionally or alternatively, only one or more Group 6, 8, 9 and/or 10 elements may present on an exterior and/or interior surface of the organosilica material and/or the support material. The surface metal(s) can be incorporated into/onto the organosilica material and/or the support material by any convenient method, such as by impregnation, deposition, grafting, co-condensation, by ion exchange, and/or the like.

In some embodiments, the support may be pre-treated prior to coating. In various aspects, pre-treating the support may comprise applying a solution comprising an oxidizing agent and, optionally an inorganic acid as described herein. Examples of suitable oxidizing agents include, but are not limited to, hydrogen peroxide and sulfuric acid. One can use hydrogen peroxide or sulfuric acid to pre-treat. Alternatively one could use both hydrogen peroxide and sulfuric acid to pre-treat.

Additionally or alternatively, an alcohol may be added to the solution described herein. As used herein, the term "alcohol" refers to a hydroxy group (—OH) bound to a saturated carbon atom (i.e., an alkyl). Examples of the alkyl portion of the alcohol include, but are not limited to propyl, butyl, pentyl, hexyl, iso-propyl, iso-butyl, sec-butyl, tert-butyl, etc. The alcohol may be straight or branched. "Alcohol" is intended to embrace all structural isomeric forms of an alcohol. Examples of suitable alcohols include, but are not limited to, $C_1$-$C_6$ alcohols, such as methanol, ethanol, propanol, isopropanol, butanol, isobutanol, n-butanol, tert-butanol, n-pentanol or hexanol. Particularly, the alcohol may be ethanol. In some cases, addition of alcohol to the solution may slow condensation of slurry when coated on a support.

Additionally or alternatively, the methods described herein can further comprise adding an additional amount of any one of compounds of Formulas (Ia) and (II)-(VI) to the slurry. In particular, an additional amount of a compound of Formula (Ia) (e.g. 1,1,3,3,5,5-hexaethoxy-1,3,5-trisilacyclohexane) may be added to the slurry.

Additionally or alternatively, the methods described herein can further comprise supplying a purge gas to the support after coating. The purge gas may be any suitable inert gas (e.g. $N_2$, Ar, etc.).

III. Membranes

Membranes can be made by the methods described herein.

In various aspects, the membrane may comprise the organosilica material as a binder in an amount of about 1%, about 5%, about 10%, about 15%, about 20%, about 25%, about 30%, about 35%, about 40%, about 45%, about 50%, about 55%, about 60%, about 65%, about 70%, or about 75%. In particular, the membranes may comprise the organosilica material as a binder in an amount of about 1% to about 75%, about 1% to about 60%, about 1% to about 50% or about 10% to about 50%.

As described above, the membranes comprises the adsorbent material as a binder comprising an organosilica material which is a polymer comprising independent units of Formula $[Z^3Z^4SiCH_2]_3$ (I), wherein each $Z^3$ represents a hydroxyl group, a $C_1$-$C_4$ alkoxy group or an oxygen atom bonded to a silicon atom of another unit and each $Z^4$ represents a hydroxyl group, a $C_1$-$C_4$ alkoxy group, a $C_1$-$C_4$ alkyl group, an oxygen atom bonded to a silicon atom of another unit or an active site on the support.

In one embodiment, each $Z^3$ can be a hydroxyl group.

Additionally or alternatively, each $Z^3$ can be a $C_1$-$C_4$ alkoxy group, a $C_1$-$C_3$ alkoxy group, a $C_1$-$C_2$ alkoxy group, or methoxy.

Additionally or alternatively, each $Z^3$ can be an oxygen atom bonded to a silicon atom of another unit or an active site on the support.

Additionally or alternatively, each $Z^3$ can be a hydroxyl group, a $C_1$-$C_2$ alkoxy group, or an oxygen atom bonded to a silicon atom of another unit or an active site on the support.

Additionally or alternatively, each $Z^4$ can be a hydroxyl group.

Additionally or alternatively, each $Z^4$ can be a $C_1$-$C_4$ alkoxy group, a $C_1$-$C_3$ alkoxy group, a $C_1$-$C_2$ alkoxy group, or methoxy.

Additionally or alternatively, each $Z^4$ can be a $C_1$-$C_4$ alkyl group, a $C_1$-$C_3$ alkyl group, a $C_1$-$C_2$ alkyl group, or methyl.

Additionally or alternatively, each $Z^4$ can be an oxygen atom bonded to a silicon atom of another unit or an active site on the support.

Additionally or alternatively, each $Z^4$ can be a hydroxyl group, a $C_1$-$C_2$ alkoxy group, a $C_1$-$C_2$ alkyl group, or an oxygen atom bonded to a silicon atom of another unit or an active site on the support.

Additionally or alternatively, each $Z^3$ can be a hydroxyl group, a $C_1$-$C_2$ alkoxy group, or an oxygen atom bonded to a silicon atom of another unit or an active site on the support and each $Z^4$ can be a hydroxyl group, a $C_1$-$C_2$ alkyl group, a $C_1$-$C_2$ alkoxy group, or an oxygen atom bonded to a silicon atom of another unit or an active site on the support.

Additionally or alternatively, each $Z^3$ can be a hydroxyl group, ethoxy, or an oxygen atom bonded to a silicon atom of another unit or an active site on the support and each $Z^4$ can be a hydroxyl group, ethoxy, or an oxygen atom bonded to a silicon atom of another unit or an active site on the support.

Additionally or alternatively, each $Z^3$ can be a hydroxyl group or an oxygen atom bonded to a silicon atom of another unit or an active site on the support and each $Z^4$ can be a hydroxyl group, or an oxygen atom bonded to a silicon atom of another unit or an active site on the support.

If a compound of Formula (Ia) is used in the methods described herein, the organosilica material made can be a homopolymer comprising independent units of Formula I.

In a particular embodiment, if a compound of Formula (Ia), such as $[(EtO)_2SiCH_2]_3$, is used in the methods described herein, the organosilica material made can be a homopolymer comprising independent units of Formula (I), wherein each $Z^3$ can be a hydroxyl group, ethoxy, or an oxygen atom bonded to a silicon atom of another unit or an active site on the support and each $Z^4$ can be a hydroxyl group, ethoxy, or an oxygen atom bonded to a silicon atom of another unit or an active site on the support.

In another particular embodiment, if two compounds of Formula (Ia), such as $[(EtO)_2SiCH_2]_3$ and $[EtOCH_3SiCH_2]_3$, are used in the methods described herein, the organosilica material made can be a copolymer comprising: independent units of Formula I, wherein each $Z^3$ can be a hydroxyl group, ethoxy, or an oxygen atom bonded to a silicon atom of another unit or an active site on the support and each $Z^4$ can be a hydroxyl group, ethoxy, or an oxygen atom bonded to a silicon atom of another unit or an active site on the support; and independent units of Formula (I), wherein each $Z^3$ can be a hydroxyl group, ethoxy, or an oxygen atom bonded to a silicon atom of another unit or an active site on the support and each $Z^4$ can be methyl.

If a compound of Formula (Ia) and a compound of Formula (II) are used in the methods described herein, the organosilica material made can be a copolymer comprising independent units of Formula I and independent units of Formula $Z^{11}OZ^{12}Z^{13}Z^{14}$ (VI), wherein each $Z^{11}$ can be a hydrogen atom or a $C_1$-$C_4$ alkyl group or a bond to a silicon atom of another monomer or an active site on the support; and $Z^{12}$, $Z^{13}$ and $Z^{14}$ each independently can be selected from the group consisting of a hydroxyl group, a $C_1$-$C_4$ alkyl group, a $C_1$-$C_4$ alkoxy group, a nitrogen-containing $C_1$-$C_{10}$ alkyl group, a nitrogen-containing heteroalkyl group, a nitrogen-containing optionally substituted heterocycloalkyl group and an oxygen atom bonded to a silicon atom of another monomer or an active site on the support.

In another particular embodiment, if a compound of Formula (Ia), such as $[(EtO)_2SiCH_2]_3$, and a compound of Formula (II), such as tetraethyl orthosilicate (TEOS), are used in the methods described herein, the organosilica material made can be a copolymer comprising: independent units of Formula (I), wherein each $Z^3$ can be a hydroxyl group, ethoxy, or an oxygen atom bonded to a silicon atom of another monomer or an active site on the support and each $Z^4$ can be a hydroxyl group, ethoxy, or an oxygen atom bonded to a silicon atom of another unit or an active site on the support; and independent units of Formula (VI), wherein each $Z^{11}$ can be a hydrogen atom, ethyl or a bond to a silicon atom of another monomer or an active site on the support; and $Z^{12}$, $Z^{13}$ and $Z^{14}$ each independently can be selected from the group consisting of a hydroxyl group, ethoxy, and an oxygen atom bonded to a silicon atom of another monomer or an active site on the support.

In another particular embodiment, if a compound of Formula (Ia), such as $[(EtO)_2SiCH_2]_3$, and compound of Formula (II), such as methyltriethoxysilane (MTES), are used in the methods described herein, the organosilica material made can be a copolymer comprising: independent units of Formula (I), wherein each $Z^3$ can be a hydroxyl group, ethoxy, or an oxygen atom bonded to a silicon atom of another unit or an active site on the support and each $Z^4$ can be a hydroxyl group, ethoxy, or an oxygen atom bonded to a silicon atom of another unit or an active site on the support; and independent units of Formula (VI), wherein each $Z^{11}$ can be a hydrogen atom, ethyl or a bond to a silicon atom of another monomer; $Z^{12}$, $Z^{13}$ each independently can be selected from the group consisting of a hydroxyl group, ethoxy, and an oxygen atom bonded to a silicon atom of another monomer or an active site on the support; and each $Z^{14}$ can be methyl.

In another particular embodiment, if a compound of Formula (Ia), such as $[(EtO)_2SiCH_2]_3$, and compound of Formula (II), such as (N,N-dimethylaminopropyl)trimethoxysilane, are used in the methods described herein, the organosilica material made can be a copolymer comprising: independent units of Formula (I), wherein each $Z^3$ can be a hydroxyl group, ethoxy, or an oxygen atom bonded to a silicon atom of another unit or an active site on the support and each $Z^4$ can be a hydroxyl group, ethoxy, or an oxygen atom bonded to a silicon atom of another unit or an active site on the support; and independent units of Formula (VI), wherein each $Z^{11}$ can be a hydrogen atom, methyl or a bond to a silicon atom of another monomer or an active site on the support; $Z^{12}$, $Z^{13}$ each independently can be selected from the group consisting of a hydroxyl group, methoxy, and an oxygen atom bonded to a silicon atom of another monomer or an active site on the support; and $Z^{14}$ can be

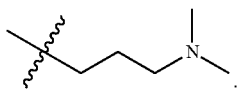

In another particular embodiment, if a compound of Formula (Ia), such as $[(EtO)_2SiCH_2]_3$, and compound of Formula (II), such as (N-(2-aminoethyl)-3-aminopropyltriethoxysilane, are used in the methods described herein, the organosilica material made can be a copolymer comprising: independent units of Formula (I), wherein each $Z^3$ can be a hydroxyl group, ethoxy, or an oxygen atom bonded to a silicon atom of another unit or an active site on the support and each $Z^4$ can be a hydroxyl group, ethoxy, or an oxygen atom bonded to a silicon atom of another unit or an active site on the support; and independent units of Formula (VI), wherein each $Z^{11}$ can be a hydrogen atom, ethyl or a bond to a silicon atom of another monomer or an active site on the support; $Z^{12}$, $Z^{13}$ each independently can be selected from the group consisting of a hydroxyl group, ethoxy, and an oxygen atom bonded to a silicon atom of another monomer or an active site on the support; and each $Z^{14}$ can be

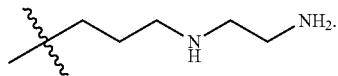 [SMILES: *CCCNCCN]

In another particular embodiment, if a compound of Formula (Ia), such as $[(EtO)_2SiCH_2]_3$, and compound of Formula (II), such as 4-methyl-1-(3-triethoxysilylpropyl)-piperazine, are used in the methods described herein, the organosilica material made can be a copolymer comprising: independent units of Formula (I), wherein each $Z^3$ can be a hydroxyl group, ethoxy, or an oxygen atom bonded to a silicon atom of another unit or an active site on the support and each $Z^4$ can be a hydroxyl group, ethoxy, or an oxygen atom bonded to a silicon atom of another unit or an active site on the support; and independent units of Formula (VI), wherein each $Z^{11}$ can be a hydrogen atom, ethyl or a bond to a silicon atom of another monomer; $Z^{12}$, $Z^{13}$ each independently can be selected from the group consisting of a hydroxyl group, ethoxy, and an oxygen atom bonded to a silicon atom of another monomer or an active site on the support; and each $Z^{14}$ can be

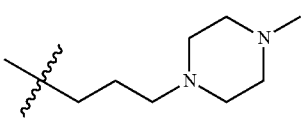

In another particular embodiment, if a compound of Formula (Ia), such as $[(EtO)_2SiCH_2]_3$, and compound of Formula (II), such as 4-(2-(triethoxysily)ethyl)pyridine, are used in the methods described herein, the organosilica material made can be a copolymer comprising: independent units of Formula (I), wherein each $Z^3$ can be a hydroxyl group, ethoxy, or an oxygen atom bonded to a silicon atom of another unit or an active site on the support and each $Z^4$ can be a hydroxyl group, ethoxy, or an oxygen atom bonded to a silicon atom of another unit or an active site on the support; and independent units of Formula (VI), wherein each $Z^{11}$ can be a hydrogen atom, ethyl or a bond to a silicon atom of another monomer; $Z^{12}$, $Z^{13}$ each independently can be selected from the group consisting of a hydroxyl group, ethoxy, and an oxygen atom bonded to a silicon atom of another monomer or an active site on the support; and each $Z^{14}$ can be

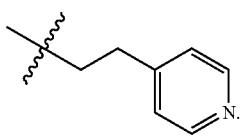 [SMILES: *CCc1ccncc1]

In another particular embodiment, if a compound of Formula (Ia), such as $[(EtO)_2SiCH_2]_3$, and compound of Formula (II), such as 1-(3-(triethoxysilyl)propyl)-4,5-dihydro-1H-imidazole, are used in the methods described herein, the organosilica material made can be a copolymer comprising: independent units of Formula (I), wherein each $Z^3$ can be a hydroxyl group, ethoxy, or an oxygen atom bonded to a silicon atom of another unit or an active site on the support and each $Z^4$ can be a hydroxyl group, ethoxy, or an oxygen atom bonded to a silicon atom of another unit or an active site on the support; and independent units of Formula (VI), wherein each $Z^{11}$ can be a hydrogen atom, ethyl or a bond to a silicon atom of another monomer; $Z^{12}$, $Z^{13}$ each independently can be selected from the group consisting of a hydroxyl group, ethoxy, and an oxygen atom bonded to a silicon atom of another monomer or an active site on the support; and each $Z^{14}$ can be

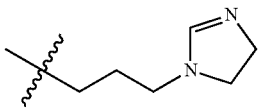

In another particular embodiment, if a compound of Formula (Ia), such as $[(EtO)_2SiCH_2]_3$, and compound of Formula (II), such as (3-aminopropyl)triethoxysilane, are used in the methods described herein, the organosilica material made can be a copolymer comprising: independent units of Formula (I), wherein each $Z^3$ can be a hydroxyl group, ethoxy, or an oxygen atom bonded to a silicon atom of another unit or an active site on the support and each $Z^4$ can be a hydroxyl group, ethoxy, or an oxygen atom bonded to a silicon atom of another unit or an active site on the support; and independent units of Formula (VI), wherein each $Z^{11}$ can be a hydrogen atom, ethyl or a bond to a silicon atom of another monomer; $Z^{12}$, $Z^{13}$ each independently can be selected from the group consisting of a hydroxyl group, ethoxy, and an oxygen atom bonded to a silicon atom of another monomer or an active site on the support; and each $Z^{14}$ can be

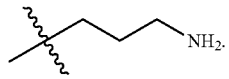

If a compound of Formula (Ia) and a compound of Formula (III) are used in the methods described herein, the organosilica material made can be a copolymer comprising independent units of Formula I and independent units of Formula $Z^{15}Z^{16}Z^{17}Si$—$R^5$—$SiZ^{15}Z^{16}Z^{17}$ (VII), wherein each $Z^{15}$ independently can be a hydroxyl group, a $C_1$-$C_4$ alkoxy group or an oxygen atom bonded to a silicon atom of another monome or an active site on the support; $Z^{16}$ and $Z^{17}$ each independently can be a hydroxyl group, a $C_1$-$C_4$ alkoxy group, a $C_1$-$C_4$ alkyl group or an oxygen atom bonded to a silicon atom of another monomer or an active site on the support; and each $R^5$ can be selected from the group consisting of a $C_1$-$C_8$ alkylene group, a $C_2$-$C_8$ alkenylene group, a $C_2$-$C_8$ alkynylene group, a nitrogen-containing $C_1$-$C_{10}$ alkylene group, an optionally substituted $C_6$-$C_{20}$ aralkyl and an optionally substituted $C_4$-$C_{20}$ heterocycloalkyl group.

In another particular embodiment, if a compound of Formula (Ia), such as $[(EtO)_2SiCH_2]_3$, and compound of Formula (III), such as (1,2-bis(methyldiethoxysilyl)ethane, are used in the methods described herein, the organosilica material made can be a copolymer comprising: independent units of Formula (I), wherein each $Z^3$ can be a hydroxyl group, ethoxy, or an oxygen atom bonded to a silicon atom of another unit or an active site on the support and each $Z^4$ can be a hydroxyl group, ethoxy, or an oxygen atom bonded to a silicon atom of another unit or an active site on the support; and independent units of Formula (VII), wherein each $Z^{15}$ can be a hydroxyl group, an ethoxy or an oxygen atom bonded to a silicon atom of another monomer or an active site on the support; each $Z^{16}$ can be a hydroxyl group, an ethoxy group or an oxygen atom bonded to a silicon atom of another monomer or an active site on the support; each $Z^{17}$ can be methyl; and each $R^5$ can be —$CH_2CH_2$—.

In another particular embodiment, if a compound of Formula (Ia), such as $[(EtO)_2SiCH_2]_3$, and compound of Formula (III), such as (bis(triethoxysilyl)methane, are used in the methods described herein, the organosilica material made can be a copolymer comprising: independent units of Formula (I), wherein each $Z^3$ can be a hydroxyl group, ethoxy, or an oxygen atom bonded to a silicon atom of another unit or an active site on the support and each $Z^4$ can be a hydroxyl group, ethoxy, or an oxygen bonded to a silicon atom of another unit or an active site on the support; and independent units of Formula (VII), wherein each $Z^{15}$ can be a hydroxyl group, an ethoxy or an oxygen atom bonded to a silicon atom of another monomer or an active site on the support; $Z^{16}$ and $Z^{17}$ can be each independently selected from the group consisting of a hydroxyl group, an ethoxy group or an oxygen atom bonded to a silicon atom of another monomer or an active site on the support; and each $R^5$ can be —$CH_2$—.

In another particular embodiment, if a compound of Formula (Ia), such as $[(EtO)_2SiCH_2]_3$, and compound of Formula (III), such as 1,2-bis(triethoxysilyl)ethylene, are used in the methods described herein, the organosilica material made can be a copolymer comprising: independent units of Formula (I), wherein each $Z^3$ can be a hydroxyl group, ethoxy, or an oxygen atom bonded to a silicon atom of another unit or an active site on the support and each $Z^4$ can be a hydroxyl group, ethoxy, or an oxygen atom bonded to a silicon atom of another unit or an active site on the support; and independent units of Formula (VII), wherein each $Z^{15}$ can be a hydroxyl group, an ethoxy or an oxygen atom bonded to a silicon atom of another monomer or an active site on the support; $Z^{16}$ and $Z^{17}$ can be each independently selected from the group consisting of a hydroxyl group, an ethoxy group or an oxygen atom bonded to a silicon atom of another monomer or an active site on the support; and each $R^5$ can be —HC═CH—.

In another particular embodiment, if a compound of Formula (Ia), such as $[(EtO)_2SiCH_2]_3$, and compound of Formula (III), such as N,N'-bis[(3-trimethoxysilyl)propyl] ethylenediamine, are used in the methods described herein, the organosilica material made can be a copolymer comprising: independent units of Formula (I), wherein each $Z^3$ can be a hydroxyl group, ethoxy, or an oxygen atom bonded to a silicon atom of another unit or an active site on the support and each $Z^4$ can be a hydroxyl group, ethoxy, or an oxygen atom bonded to a silicon atom of another unit or an active site on the support; and independent units of Formula (VII), wherein each $Z^{15}$ can be a hydroxyl group, an methoxy or an oxygen atom bonded to a silicon atom of another monomer or an active site on the support; each $Z^{16}$ and $Z^{17}$ can be each independently selected from the group consisting of a hydroxyl group, an methoxy group or an oxygen atom bonded to a silicon atom of another monomer or an active site on the support; and each $R^5$ can be

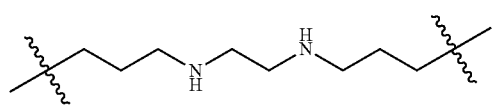

In another particular embodiment, if a compound of Formula (Ia), such as $[(EtO)_2SiCH_2]_3$, and compound of Formula (III), such as bis[(methyldiethoxysilyl)propyl]amine, are used in the methods described herein, the organosilica material made can be a copolymer comprising: independent units of Formula (I), wherein each $Z^3$ can be a hydroxyl group, ethoxy, or an oxygen atom bonded to a silicon atom of another unit or an active site on the support and each $Z^4$ can be a hydroxyl group, ethoxy, or an oxygen atom bonded to a silicon atom of another unit or an active site on the support; and independent units of Formula (VII), wherein each $Z^{15}$ can be a hydroxyl group, an ethoxy or an oxygen atom bonded to a silicon atom of another monomer or an active site on the support; each $Z^{16}$ can be a hydroxyl group, an ethoxy group or an oxygen atom bonded to a silicon atom of another monomer or an active site on the support; $Z^{17}$ can be methyl; and each $R^5$ can be

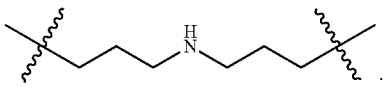 [SMILES: *CCCNCCC*]

In another particular embodiment, if a compound of Formula (Ia), such as $[(EtO)_2SiCH_2]_3$, and compound of Formula (III), such as bis[(methyldimethoxysilyl)propyl]-N-methylamine, are used in the methods described herein, the organosilica material made can be a copolymer comprising: independent units of Formula (I), wherein each $Z^3$ can be a hydroxyl group, ethoxy, or an oxygen atom bonded to a silicon atom of another unit or an active site on the support and each $Z^4$ can be a hydroxyl group, ethoxy, or an oxygen atom bonded to a silicon atom of another unit or an active site on the support; and independent units of Formula (VII), wherein each $Z^{15}$ can be a hydroxyl group, a methoxy or an oxygen atom bonded to a silicon atom of another monomer or an active site on the support; each $Z^{16}$ can be a hydroxyl group, a methoxy group or an oxygen atom bonded to a silicon atom of another monomer or an active site on the support; $Z^{17}$ can be methyl; and each $R^5$ can be

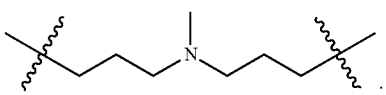 [SMILES: *CCCN(C)CCC*]

If a compound of Formula (Ia) and a compound of Formula (IV) are used in the methods described herein, the organosilica material made can be a copolymer comprising independent units of Formula I and independent units of Formula $M^3(OZ^{18})_3$ (VIII), wherein $M^3$ can be a Group 13 metal and each $Z^{18}$ independently can be a hydrogen atom, a $C_1$-$C_6$ alkyl or a bond to a silicon atom of another monomer or an active site on the support.

In another particular embodiment, if a compound of Formula (Ia), such as $[(EtO)_2SiCH_2]_3$, and compound of Formula (IV), such as aluminum tri-sec-butoxide, are used in the methods described herein, the organosilica material made can be a copolymer comprising: independent units of Formula (I), wherein $Z^3$ can be a hydroxyl group, ethoxy, or an oxygen atom bonded to a silicon atom of another unit or an active site on the support and $Z^4$ can be a hydroxyl group, ethoxy, or an oxygen atom bonded to a silicon atom of another unit or an active site on the support; and independent units of Formula (VIII), wherein $M^{13}$ can be a Group 13 metal and $Z^{18}$ can be a hydrogen atom, a sec-butyl or a bond to a silicon atom of another monomer or an active site on the support.

If a compound of Formula (Ia) and a compound of Formula (V) are used in the methods described herein, the organosilica material made can be a copolymer comprising independent units of Formula I and independent units of Formula $(Z^{19}O)_2M^4$—O—$Si(OZ^{20})_3$ (IX), wherein $M^4$ represents a Group 13 metal and $Z^{19}$ and $Z^{20}$ each independently represent a hydrogen atom, a $C_1$-$C_6$ alkyl group or a bond to a silicon atom of another monomer or an active site on the support.

If a compound of Formula (Ia) and a compound of Formula (VI) are used in the methods described herein, the organosilica material made can be a copolymer comprising independent units of Formula I and independent cyclic polyurea units of Formula

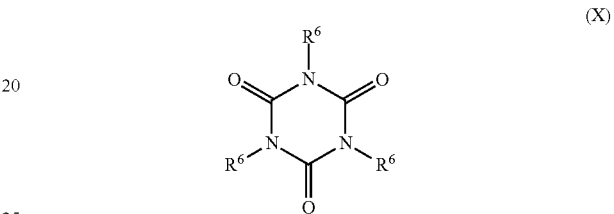

wherein each $R^6$ independently can be a $Z^{21}OZ^{22}Z^{23}SiZ^{24}$ group, wherein each $Z^{21}$ can be a hydrogen atom, a $C_1$-$C_4$ alkyl group, or a bond to a silicon atom of another monomer unit or an active site on the support; $Z^{22}$ and $Z^{23}$ each independently can be a hydroxyl group, a $C_1$-$C_4$ alkyl group, a $C_1$-$C_4$ alkoxy group or an oxygen atom bonded to a silicon atom of another monomer unit or an active site on the support; and each $Z^{24}$ can be a $C_1$-$C_8$ alkylene group bonded to a nitrogen atom of the cyclic polyurea.

In another particular embodiment, if only a compound of Formula (VI), such as tris(3-trimethoxysilylpropyl)isocyanurate is used in the methods described herein, the organosilica material made can be a homopolymer comprising: independent units of Formula (X), wherein each $Z^{21}$ can be a hydrogen atom, methyl, or a bond to a silicon atom of another monomer or an active site on the support; $Z^{22}$ and $Z^{23}$ each independently can be a hydroxyl group, methoxy or an oxygen atom bonded to a silicon atom of another monomer unit or an active site on the support; and $Z^{24}$ can be —$CH_2CH_2CH_2$— bonded to a nitrogen atom of the cyclic polyurea.

In another particular embodiment, if a compound of Formula (Ia), such as $[(EtO)_2SiCH_2]_3$, and compound of Formula (VI), such as tris(3-trimethoxysilylpropyl)isocyanurate, are used in the methods described herein, the organosilica material made can be a copolymer comprising: independent units of Formula (I), wherein each $Z^3$ can be a hydroxyl group, ethoxy, or an oxygen atom bonded to a silicon atom of another unit or an active site on the support and each $Z^4$ can be a hydroxyl group, ethoxy, or an oxygen atom bonded to a silicon atom of another unit or an active site on the support; and independent units of Formula (X), wherein each $Z^{21}$ can be a hydrogen atom, methyl, or a bond to a silicon atom of another monomer or an active site on the support; $Z^{22}$ and $Z^{23}$ each independently can be a hydroxyl group, methoxy or an oxygen atom bonded to a silicon atom of another monomer unit or an active site on the support; and $Z^{24}$ can be —$CH_2CH_2CH_2$— bonded to a nitrogen atom of the cyclic polyurea.

In another particular embodiment, if a compound of compound of Formula (II), such as tetraethyl orthosilicate (TEOS) and compound of Formula (VI), such as tris(3-trimethoxysilylpropyl)isocyanurate, are used in the methods described herein, the organosilica material made can be a copolymer comprising: independent units of Formula (VI), wherein each $Z^{11}$ can be a hydrogen atom, ethyl or a bond to a silicon atom of another monomer or an active site on the support; and $Z^{12}$, $Z^{13}$ and $Z^{14}$ each independently can be selected from the group consisting of a hydroxyl group, ethoxy, and an oxygen atom bonded to a silicon atom of another monomer or an active site on the support; and independent units of Formula (X), wherein each $Z^{21}$ can be a hydrogen atom, methyl, or a bond to a silicon atom of another monomer or an active site on the support; $Z^{22}$ and $Z^{23}$ each independently can be a hydroxyl group, methoxy or an oxygen atom bonded to a silicon atom of another monomer unit or an active site on the support; and $Z^{24}$ can be —$CH_2CH_2CH_2$— bonded to a nitrogen atom of the cyclic polyurea.

The organosilica materials made by the methods described herein can be characterized as described in the following sections.

III. A. X-Ray Diffraction Peaks

The organosilica materials made by the methods described herein can exhibit powder X-ray diffraction patterns with one broad peak between about 1 and about 4 degrees 2θ, particularly one broad peak between about 1 and about 3 degrees 2θ. Additionally or alternatively, the organosilica materials can exhibit substantially no peaks in the range of about 0.5 to about 10 degrees 2θ, about 0.5 to about 12 degrees 2θ range, about 0.5 to about 15 degrees 2θ, about 0.5 to about 20 degrees 2θ, about 0.5 to about 30 degrees 2θ, about 0.5 to about 40 degrees 2θ, about 0.5 to about 50 degrees 2θ, about 0.5 to about 60 degrees 2θ, about 0.5 to about 70 degrees 2θ, about 2 to about 10 degrees 2θ, about 2 to about 12 degrees 2θ range, about 2 to about 15 degrees 2θ, about 2 to about 20 degrees 2θ, about 2 to about 30 degrees 2θ, about 2 to about 40 degrees 2θ, about 2 to about 50 degrees 2θ, about 2 to about 60 degrees 2θ, about 2 to about 70 degrees 2θ, about 3 to about 10 degrees 2θ, about 3 to about 12 degrees 2θ range, about 3 to about 15 degrees 2θ, about 3 to about 20 degrees 2θ, about 3 to about 30 degrees 2θ, about 3 to about 40 degrees 2θ, about 3 to about 50 degrees 2θ, about 3 to about 60 degrees 2θ, or about 3 to about 70 degrees 2θ.

III. B. Silanol Content

In various aspects, the organosilica material herein can have a silanol content of greater than about 5%, greater than about 10%, greater than about 15%, greater than about 20%, greater than about 25%, greater than about 30%, greater than about 33%, greater than 35%, greater than about 40%, greater than about 41%, greater than about 44%, greater than about 45%, greater than about 50%, greater than about 55%, greater than about 60%, greater than about 65%, greater than about 70%, greater than about 75%, or about 80%. In certain embodiments, the silanol content can be greater than about 30% or greater than about 41%.

Additionally or alternatively, the organosilica material herein may have a silanol content of about 5% to about 80%, about 5% to about 75%, about 5% to about 70%, about 5% to about 65%, about 5% to about 60%, about 5% to about 55%, about 5% to about 50%, about 5% to about 45%, about 5% to about 44%, about 5% to about 41%, about 5% to about 40%, about 5% to about 35%, about 5% to about 33%, about 5% to about 30%, about 5% to about 25%, about 5% to about 20%, about 5% to about 15%, about 5% to about 10%, about 10% to about 80%, about 10% to about 75%, about 10% to about 70%, about 10% to about 65%, about 10% to about 60%, about 10% to about 55%, about 10% to about 50%, about 10% to about 45%, about 10% to about 44%, about 10% to about 41%, about 10% to about 40%, about 10% to about 35%, about 10% to about 33%, about 10% to about 30%, about 10% to about 25%, about 10% to about 20%, about 20% to about 80%, about 20% to about 75%, about 20% to about 70%, about 20% to about 65%, about 20% to about 60%, about 20% to about 55%, about 20% to about 50%, about 20% to about 45%, about 20% to about 44%, about 20% to about 41%, about 20% to about 40%, about 20% to about 35%, about 20% to about 33%, about 20% to about 30%, about 20% to about 25%, about 30% to about 80%, about 30% to about 75%, about 30% to about 70%, about 30% to about 65%, about 30% to about 60%, about 30% to about 55%, about 30% to about 50%, about 30% to about 45%, about 30% to about 44%, about 30% to about 41%, about 30% to about 40%, about 30% to about 35%, about 30% to about 33%, about 40% to about 80%, about 40% to about 75%, about 40% to about 70%, about 40% to about 65%, about 40% to about 60%, about 40% to about 55%, about 40% to about 50%, about 40% to about 45%, about 40% to about 44%, or about 40% to about 41%.

III.C. Pore Size

The organosilica material produced by the methods described herein r can advantageously be in a mesoporous form. As indicated previously, the term mesoporous refers to solid materials having pores with a diameter within the range of from about 2 nm to about 50 nm. The average pore diameter of the organosilica material can be determined, for example, using nitrogen adsorption-desorption isotherm techniques within the expertise of one of skill in the art, such as the BET (Brunauer Emmet Teller) method.

The organosilica material used as a binder can have an average pore diameter of about 0.2 nm, about 0.4 nm, about 0.5 nm, about 0.6 nm, about 0.8 nm, about 1.0 nm, about 1.5 nm, about 1.8 nm or less than about 2.0 nm.

Additionally or alternatively, the organosilica material can advantageously have an average pore diameter within the mesopore range of about 2.0 nm, about 2.5 nm, about 3.0 nm, about 3.1 nm, about 3.2 nm, about 3.3 nm, about 3.4 nm, about 3.5 nm, about 3.6 nm, about 3.7 nm, about 3.8 nm, about 3.9 nm about 4.0 nm, about 4.1 nm, about 4.5 nm, about 5.0 nm, about 6.0 nm, about 7.0 nm, about 7.3 nm, about 8 nm, about 8.4 nm, about 9 nm, about 10 nm, about 11 nm, about 13 nm, about 15 nm, about 18 nm, about 20 nm, about 23 nm, about 25 nm, about 30 nm, about 40 nm, about 45 nm, or about 50 nm.

Additionally or alternatively, the organosilica material can have an average pore diameter of 0.2 nm to about 50 nm, about 0.2 nm to about 40 nm, about 0.2 nm to about 30 nm, about 0.2 nm to about 25 nm, about 0.2 nm to about 23 nm, about 0.2 nm to about 20 nm, about 0.2 nm to about 18 nm, about 0.2 nm to about 15 nm, about 0.2 nm to about 13 nm, about 0.2 nm to about 11 nm, about 0.2 nm to about 10 nm, about 0.2 nm to about 9 nm, about 0.2 nm to about 8.4 nm, about 0.2 nm to about 8 nm, about 0.2 nm to about 7.3 nm, about 0.2 nm to about 7.0 nm, about 0.2 nm to about 6.0 nm, about 0.2 nm to about 5.0 nm, about 0.2 nm to about 4.5 nm, about 0.2 nm to about 4.1 nm, about 0.2 nm to about 4.0 nm, about 0.2 nm to about 3.9 nm, about 0.2 nm to about 3.8 nm, about 0.2 nm to about 3.7 nm, about 0.2 nm to about 3.6 nm, about 0.2 nm to about 3.5 nm, about 0.2 nm to about 3.4 nm, about 0.2 nm to about 3.3 nm, about 0.2 nm to about 3.2 nm, about 0.2 nm to about 3.1 nm, about 0.2 nm to about 3.0 nm, about 0.2 nm to about 2.5 nm, about 0.2 nm to about 2.0 nm, about 0.2 nm to about 1.0 nm, about 1.0 nm to about 50 nm, about 1.0 nm to about 40 nm, about 1.0 nm to about 30 nm, about 1.0 nm to about 25 nm, about 1.0 nm to about 23 nm, about 1.0 nm to about 20 nm, about 1.0 nm to about 18 nm, about 1.0 nm to about 15 nm, about 1.0 nm to about 13 nm, about 1.0 nm to about 11 nm, about 1.0 nm to about 10 nm, about 1.0 nm to about 9 nm, about 1.0 nm to about 8.4 nm, about 1.0 nm to about 8 nm, about 1.0 nm to about 7.3 nm, about 1.0 nm to about 7.0 nm, about 1.0 nm to about 6.0 nm, about 1.0 nm to about 5.0 nm, about 1.0 nm to about 4.5 nm, about 1.0 nm to about 4.1 nm, about 1.0 nm to about 4.0 nm, about 1.0 nm to about 3.9 nm, about 1.0 nm to about 3.8 nm, about 1.0 nm to about 3.7 nm, about 1.0 nm to about 3.6 nm, about 1.0 nm to about 3.5 nm, about 1.0 nm to about 3.4 nm, about 1.0 nm to about 3.3 nm, about 1.0 nm to about 3.2 nm, about 1.0 nm to about 3.1 nm, about 1.0 nm to about 3.0 nm or about 1.0 nm to about 2.5 nm.

In particular, the organosilica material can advantageously have an average pore diameter in the mesopore range of about 2.0 nm to about 50 nm, about 2.0 nm to about 40 nm, about 2.0 nm to about 30 nm, about 2.0 nm to about 25 nm, about 2.0 nm to about 23 nm, about 2.0 nm to about 20 nm, about 2.0 nm to about 18 nm, about 2.0 nm to about 15 nm, about 2.0 nm to about 13 nm, about 2.0 nm to about 11 nm, about 2.0 nm to about 10 nm, about 2.0 nm to about 9 nm, about 2.0 nm to about 8.4 nm, about 2.0 nm to about 8 nm, about 2.0 nm to about 7.3 nm, about 2.0 nm to about 7.0 nm, about 2.0 nm to about 6.0 nm, about 2.0 nm to about 5.0 nm, about 2.0 nm to about 4.5 nm, about 2.0 nm to about 4.1 nm, about 2.0 nm to about 4.0 nm, about 2.0 nm to about 3.9 nm, about 2.0 nm to about 3.8 nm, about 2.0 nm to about 3.7 nm, about 2.0 nm to about 3.6 nm, about 2.0 nm to about 3.5 nm, about 2.0 nm to about 3.4 nm, about 2.0 nm to about 3.3 nm, about 2.0 nm to about 3.2 nm, about 2.0 nm to about 3.1 nm, about 2.0 nm to about 3.0 nm, about 2.0 nm to about 2.5 nm, about 2.5 nm to about 50 nm, about 2.5 nm to about 40 nm, about 2.5 nm to about 30 nm, about 2.5 nm to about 25 nm, about 2.5 nm to about 23 nm, about 2.5 nm to about 20 nm, about 2.5 nm to about 18 nm, about 2.5 nm to about 15 nm, about 2.5 nm to about 13 nm, about 2.5 nm to about 11 nm, about 2.5 nm to about 10 nm, about 2.5 nm to about 9 nm, about 2.5 nm to about 8.4 nm, about 2.5 nm to about 8 nm, about 2.5 nm to about 7.3 nm, about 2.5 nm to about 7.0 nm, about 2.5 nm to about 6.0 nm, about 2.5 nm to about 5.0 nm, about 2.5 nm to about 4.5 nm, about 2.5 nm to about 4.1 nm, about 2.5 nm to about 4.0 nm, about 2.5 nm to about 3.9 nm, about 2.5 nm to about 3.8 nm, about 2.5 nm to about 3.7 nm, about 2.5 nm to about 3.6 nm, about 2.5 nm to about 3.5 nm, about 2.5 nm to about 3.4 nm, about 2.5 nm to about 3.3 nm, about 2.5 nm to about 3.2 nm, about 2.5 nm to about 3.1 nm, about 2.5 nm to about 3.0 nm, about 3.0 nm to about 50 nm, about 3.0 nm to about 40 nm, about 3.0 nm to about 30 nm, about 3.0 nm to about 25 nm, about 3.0 nm to about 23 nm, about 3.0 nm to about 20 nm, about 3.0 nm to about 18 nm, about 3.0 nm to about 15 nm, about 3.0 nm to about 13 nm, about 3.0 nm to about 11 nm, about 3.0 nm to about 10 nm, about 3.0 nm to about 9 nm, about 3.0 nm to about 8.4 nm, about 3.0 nm to about 8 nm, about 3.0 nm to about 7.3 nm, about 3.0 nm to about 7.0 nm, about 3.0 nm to about 6.0 nm, about 3.0 nm to about 5.0 nm, about 3.0 nm to about 4.5 nm, about 3.0 nm to about 4.1 nm, or about 3.0 nm to about 4.0 nm In one particular embodiment, the organo silica material produced by the methods described herein can have an average pore diameter of about 1.0 nm to about 30.0 nm, particularly about 1.0 nm to about 25.0 nm, particularly about 1.5 nm to about 25.0 nm, particularly about 2.0 nm to about 25.0 nm, particularly about 2.0 nm to about 20.0 nm, particularly about 2.0 nm to about 15.0 nm, or particularly about 2.0 nm to about 10.0 nm.

Using surfactant as a template to synthesize mesoporous materials can create highly ordered structure, e.g. well-defined cylindrical-like pore channels. In some circumstances, there may be no hysteresis loop observed from $N_2$ adsorption isotherm. In other circumstances, for instance where mesoporous materials can have less ordered pore structures, a hysteresis loop may be observed from $N_2$ adsorption isotherm experiments. In such circumstances, without being bound by theory, the hysteresis can result from the lack of regularity in the pore shapes/sizes and/or from bottleneck constrictions in such irregular pores.

III.D. Surface Area

The surface area of the organosilica material can be determined, for example, using nitrogen adsorption-desorption isotherm techniques within the expertise of one of skill in the art, such as the BET (Brunauer Emmet Teller) method. This method may determine a total surface area, an external surface area, and a microporous surface area. As used herein, and unless otherwise specified, "total surface area" refers to the total surface area as determined by the BET method. As used herein, and unless otherwise specified, "microporous surface area" refers to microporous surface are as determined by the BET method.

In various embodiments, the organosilica material can have a total surface area greater than or equal to about 100 $m^2/g$, greater than or equal to about 200 $m^2/g$, greater than or equal to about 300 $m^2/g$, greater than or equal to about 400 $m^2/g$, greater than or equal to about 450 $m^2/g$, greater than or equal to about 500 $m^2/g$, greater than or equal to about 550 $m^2/g$, greater than or equal to about 600 $m^2/g$, greater than or equal to about 700 $m^2/g$, greater than or equal to about 800 $m^2/g$, greater than or equal to about 850 $m^2/g$, greater than or equal to about 900 $m^2/g$, greater than or equal to about 1,000 $m^2/g$, greater than or equal to about 1,050 $m^2/g$, greater than or equal to about 1,100 $m^2/g$, greater than or equal to about 1,150 $m^2/g$, greater than or equal to about 1,200 $m^2/g$, greater than or equal to about 1,250 $m^2/g$, greater than or equal to about 1,300 $m^2/g$, greater than or equal to about 1,400 $m^2/g$, greater than or equal to about 1,450 $m^2/g$, greater than or equal to about 1,500 $m^2/g$, greater than or equal to about 1,550 $m^2/g$, greater than or equal to about 1,600 $m^2/g$, greater than or equal to about 1,700 $m^2/g$, greater than or equal to about 1,800 $m^2/g$, greater than or equal to about 1,900 $m^2/g$, greater than or equal to about 2,000 $m^2/g$, greater than or equal to greater than or equal to about 2,100 $m^2/g$, greater than or equal to about 2,200 $m^2/g$, greater than or equal to about 2,300 $m^2/g$ or about 2,500 $m^2/g$.

Additionally or alternatively, the organosilica material may have a total surface area of about 50 $m^2/g$ to about 2,500 $m^2/g$, about 50 $m^2/g$ to about 2,000 $m^2/g$, about 50 $m^2/g$ to about 1,500 $m^2/g$, about 50 $m^2/g$ to about 1,000 $m^2/g$, about 100 $m^2/g$ to about 2,500 $m^2/g$, about 100 $m^2/g$ to about 2,300 $m^2/g$, about 100 $m^2/g$ to about 2,200 $m^2/g$, about 100 $m^2/g$ to about 2,100 $m^2/g$, about 100 $m^2/g$ to about 2,000 $m^2/g$, about 100 $m^2/g$ to about 1,900 $m^2/g$, about 100 $m^2/g$ to about 1,800 $m^2/g$, about 100 $m^2/g$ to about 1,700 $m^2/g$, about 100 $m^2/g$ to about 1,600 $m^2/g$, about 100 $m^2/g$ to about 1,550 $m^2/g$, about 100 $m^2/g$ to about 1,500 $m^2/g$, about 100 $m^2/g$ to about 1,450 $m^2/g$, about 100 $m^2/g$ to about 1,400 $m^2/g$, about 100 $m^2/g$ to about 1,300 $m^2/g$, about 100 $m^2/g$ to about 1,250 $m^2/g$, about 100 $m^2/g$ to about 1,200 $m^2/g$, about 100 $m^2/g$ to about 1,150 $m^2/g$, about 100 $m^2/g$ to about 1,100 $m^2/g$, about 100 $m^2/g$ to about 1,050 $m^2/g$, about 100 $m^2/g$ to about 1,000 $m^2/g$, about 100 $m^2/g$ to about 900 m²/g, about 100 m²/g to about 850 m²/g, about 100 m²/g to about 800 m²/g, about 100 m²/g to about 700 m²/g, about 100 m²/g to about 600 m²/g, about 100 m²/g to about 550 m²/g, about 100 m²/g to about 500 m²/g, about 100 m²/g to about 450 m²/g, about 100 m²/g to about 400 m²/g, about 100 m²/g to about 300 m²/g, about 100 m²/g to about 200 m²/g, about 200 m²/g to about 2,500 m²/g, about 200 m²/g to about 2,300 m²/g, about 200 m²/g to about 2,200 m²/g, about 200 m²/g to about 2,100 m²/g, about 200 m²/g to about 2,000 m²/g, about 200 m²/g to about 1,900 m²/g, about 200 m²/g to about 1,800 m²/g, about 200 m²/g to about 1,700 m²/g, about 200 m²/g to about 1,600 m²/g, about 200 m²/g to about 1,550 m²/g, about 200 m²/g to about 1,500 m²/g, about 200 m²/g to about 1,450 m²/g, about 200 m²/g to about 1,400 m²/g, about 200 m²/g to about 1, 300 m²/g, about 200 m²/g to about 1,250 m²/g, about 200 m²/g to about 1,200 m²/g, about 200 m²/g to about 1,150 m²/g, about 200 m²/g to about 1,100 m²/g, about 200 m²/g to about 1,050 m²/g, about 200 m²/g to about 1,000 m²/g, about 200 m²/g to about 900 m²/g, about 200 m²/g to about 850 m²/g, about 200 m²/g to about 800 m²/g, about 200 m²/g to about 700 m²/g, about 200 m²/g to about 600 m²/g, about 200 m²/g to about 550 m²/g, about 200 m²/g to about 500 m²/g, about 200 m²/g to about 450 m²/g, about 200 m²/g to about 400 m²/g, about 200 m²/g to about 300 m²/g, about 500 m²/g to about 2,500 m²/g, about 500 m²/g to about 2,300 m²/g, about 500 m²/g to about 2,200 m²/g, about 500 m²/g to about 2,100 m²/g, about 500 m²/g to about 2,000 m²/g, about 500 m²/g to about 1,900 m²/g, about 500 m²/g to about 1,800 m²/g, about 500 m²/g to about 1,700 m²/g, about 500 m²/g to about 1,600 m²/g, about 500 m²/g to about 1,550 m²/g, about 500 m²/g to about 1,500 m²/g, about 500 m²/g to about 1,450 m²/g, about 500 m²/g to about 1,400 m²/g, about 500 m²/g to about 1,300 m²/g, about 500 m²/g to about 1,250 m²/g, about 500 m²/g to about 1,200 m²/g, about 500 m²/g to about 1,150 m²/g, about 500 m²/g to about 1,100 m²/g, about 500 m²/g to about 1,050 m²/g, about 500 m²/g to about 1,000 m²/g, about 500 m²/g to about 900 m²/g, about 500 m²/g to about 850 m²/g, about 500 m²/g to about 800 m²/g, about 500 m²/g to about 700 m²/g, about 500 m²/g to about 600 m²/g, about 500 m²/g to about 550 m²/g, about 1,000 m²/g to about 2,500 m²/g, about 1,000 m²/g to about 2,300 m²/g, about 1,000 m²/g to about 2,200 m²/g, about 1,000 m²/g to about 2,100 m²/g, about 1,000 m²/g to about 2,000 m²/g, about 1,000 m²/g to about 1,900 m²/g, about 1,000 m²/g to about 1,800 m²/g, about 1,000 m²/g to about 1,700 m²/g, about 1,000 m²/g to about 1,600 m²/g, about 1,000 m²/g to about 1,550 m²/g, about 1,000 m²/g to about 1,500 m²/g, about 1,000 m²/g to about 1,450 m²/g, about 1,000 m²/g to about 1,400 m²/g, about 1,000 m²/g to about 1, 300 m²/g, about 1,000 m²/g to about 1,250 m²/g, about 1,000 m²/g to about 1,200 m²/g, about 1,000 m²/g to about 1,150 m²/g, about 1,000 m²/g to about 1,100 m²/g, or about 1,000 m²/g to about 1,050 m²/g.

In one particular embodiment, the organo silica material described herein may have a total surface area of about 100 m²/g to about 2,500 m² g, particularly about 200 m²/g to about 2,500 m²/g, particularly about 200 m²/g to about 2,000 m²/g, particularly about 500 m²/g to about 2,000 m²/g, or particularly about 1,000 m²/g to about 2,000 m²/g.

III.E. Pore Volume

The pore volume of the organosilica material made by the methods described herein can be determined, for example, using nitrogen adsorption-desorption isotherm techniques within the expertise of one of skill in the art, such as the BET (Brunauer Emmet Teller) method.

In various embodiments, the organosilica material can have a pore volume greater than or equal to about 0.1 cm³/g, greater than or equal to about 0.2 cm³/g, greater than or equal to about 0.3 cm³/g, greater than or equal to about 0.4 cm³/g, greater than or equal to about 0.5 cm³/g, greater than or equal to about 0.6 cm³/g, greater than or equal to about 0.7 cm³/g, greater than or equal to about 0.8 cm³/g, greater than or equal to about 0.9 cm³/g, greater than or equal to about 1.0 cm³/g, greater than or equal to about 1.1 cm³/g, greater than or equal to about 1.2 cm³/g, greater than or equal to about 1.3 cm³/g, greater than or equal to about 1.4 cm³/g, greater than or equal to about 1.5 cm³/g, greater than or equal to about 1.6 cm³/g, greater than or equal to about 1.7 cm³/g, greater than or equal to about 1.8 cm³/g, greater than or equal to about 1.9 cm³/g, greater than or equal to about 2.0 cm³/g, greater than or equal to about 2.5 cm³/g, greater than or equal to about 3.0 cm³/g, greater than or equal to about 3.5 cm³/g, greater than or equal to about 4.0 cm³/g, greater than or equal to about 5.0 cm³/g, greater than or equal to about 6.0 cm³/g, greater than or equal to about 7.0 cm³/g, or about 10.0 cm³/g.

Additionally or alternatively, the organosilica material can have a pore volume of about 0.1 cm³/g to about 10.0 cm³/g, about 0.1 cm³/g to about 7.0 cm³/g, about 0.1 cm³/g to about 6.0 cm³/g, about 0.1 cm³/g to about 5.0 cm³/g, about 0.1 cm³/g to about 4.0 cm³/g, about 0.1 cm³/g to about 3.5 cm³/g, about 0.1 cm³/g to about 3.0 cm³/g, about 0.1 cm³/g to about 2.5 cm³/g, about 0.1 cm³/g to about 2.0 cm³/g, about 0.1 cm³/g to about 1.9 cm³/g, about 0.1 cm³/g to about 1.8 cm³/g, about 0.1 cm³/g to about 1.7 cm³/g, about 0.1 cm³/g to about 1.6 cm³/g, about 0.1 cm³/g to about 1.5 cm³/g, about 0.1 cm³/g to about 1.4 cm³/g, about 0.1 cm³/g to about 1.3 cm³/g, about 0.1 cm³/g to about 1.2 cm³/g, about 0.1 cm³/g to about 1.1, about 0.1 cm³/g to about 1.0 cm³/g, about 0.1 cm³/g to about 0.9 cm³/g, about 0.1 cm³/g to about 0.8 cm³/g, about 0.1 cm³/g to about 0.7 cm³/g, about 0.1 cm³/g to about 0.6 cm³/g, about 0.1 cm³/g to about 0.5 cm³/g, about 0.1 cm³/g to about 0.4 cm³/g, about 0.1 cm³/g to about 0.3 cm³/g, about 0.1 cm³/g to about 0.2 cm³/g, 0.2 cm³/g to about 10.0 cm³/g, about 0.2 cm³/g to about 7.0 cm³/g, about 0.2 cm³/g to about 6.0 cm³/g, about 0.2 cm³/g to about 5.0 cm³/g, about 0.2 cm³/g to about 4.0 cm³/g, about 0.2 cm³/g to about 3.5 cm³/g, about 0.2 cm³/g to about 3.0 cm³/g, about 0.2 cm³/g to about 2.5 cm³/g, about 0.2 cm³/g to about 2.0 cm³/g, about 0.2 cm³/g to about 1.9 cm³/g, about 0.2 cm³/g to about 1.8 cm³/g, about 0.2 cm³/g to about 1.7 cm³/g, about 0.2 cm³/g to about 1.6 cm³/g, about 0.2 cm³/g to about 1.5 cm³/g, about 0.2 cm³/g to about 1.4 cm³/g, about 0.2 cm³/g to about 1.3 cm³/g, about 0.2 cm³/g to about 1.2 cm³/g, about 0.2 cm³/g to about 1.1, about 0.5 cm³/g to about 1.0 cm³/g, about 0.5 cm³/g to about 0.9 cm³/g, about 0.5 cm³/g to about 0.8 cm³/g, about 0.5 cm³/g to about 0.7 cm³/g, about 0.5 cm³/g to about 0.6 cm³/g, about 0.5 cm³/g to about 0.5 cm³/g, about 0.5 cm³/g to about 0.4 cm³/g, about 0.5 cm³/g to about 0.3 cm³/g, 0.5 cm³/g to about 10.0 cm³/g, about 0.5 cm³/g to about 7.0 cm³/g, about 0.5 cm³/g to about 6.0 cm³/g, about 0.5 cm³/g to about 5.0 cm³/g, about 0.5 cm³/g to about 4.0 cm³/g, about 0.5 cm³/g to about 3.5 cm³/g, about 0.5 cm³/g to about 3.0 cm³/g, about 0.5 cm³/g to about 2.5 cm³/g, about 0.5 cm³/g to about 2.0 cm³/g, about 0.5 cm³/g to about 1.9 cm³/g, about 0.5 cm³/g to about 1.8 cm³/g, about 0.5 cm³/g to about 1.7 cm³/g, about 0.5 cm³/g to about 1.6 cm³/g, about 0.5 cm³/g to about 1.5 cm³/g, about 0.5 cm³/g to about 1.4 cm³/g, about 0.5 cm³/g to about 1.3 cm³/g, about 0.5 cm³/g to about 1.2 cm³/g, about 0.5 cm³/g to about 1.1, about 0.5 cm³/g to about 1.0 cm³/g, about 0.5 cm³/g to about 0.9 cm³/g, about 0.5 cm³/g to about 0.8 cm³/g, about 0.5 cm³/g to about 0.7 cm³/g, or about 0.5 cm³/g to about 0.6 cm³/g.

IV. Uses Of The Membranes

The membranes materials obtainable by the method of the present invention find uses in several areas.

In certain embodiments, the membranes described herein can be used to filter out various contaminants from petrochemical and chemical feeds. Such feedstreams can include crude oil, hydrocarbon feeds, diesel, kerosene, lubricating oil feedstreams, heavy coker gasoil (HKGO), de-asphalted oil (DAO), FCC main column bottom (MCB), steam cracker tar. Such feedstreams can also include other distillate feedstreams such as light to heavy distillates including raw virgin distillates, wax-containing feedstreams such as feeds derived from crude oils, shale oils and tar sands. Synthetic feeds such as those derived from the Fischer-Tropsch process can also be aromatically saturated using the hydrogenation catalyst described herein. Typical wax-containing feedstocks for the preparation of lubricating base oils have initial boiling points of about 315° C. or higher, and include feeds such as whole and reduced petroleum crudes, hydrocrackates, raffinates, hydrotreated oils, gas oils (such as atmospheric gas oils, vacuum gas oils, and coker gas oils), atmospheric and vacuum residues, deasphalted oils/residua (e.g., propane deasphalted residua, brightstock, cycle oil), dewaxed oils, slack waxes and Fischer-Tropsch wax, and mixtures of these materials. Such feeds may be derived from distillation towers (atmospheric and vacuum), hydrocrackers, hydrotreaters and solvent extraction units, and may have wax contents of up to 50% or more. Preferred lubricating oil boiling range feedstreams include feedstreams which boil in the range of 650-1100° F. Diesel boiling range feedstreams include feedstreams which boil in the range of 480-660° F. Kerosene boiling range feedstreams include feedstreams which boil in the range of 350-617° F. In particular, the membranes made according the methods described herein can be used for removal of contaminants from a hydrocarbon feedstream, such as a crude oil.

Examples of contaminants that may be removed using the membranes described herein include, but are not limited to, microcarbon residue (MCR), metals, asphaltenes, and combinations thereof In particular, the membranes made according the methods described herein can be used in methods for removal of a contaminant (e.g., microcarbon residue) from a hydrocarbon feedstream (e.g. a crude oil). The methods can comprise filtering a hydrocarbon feedstream (e.g. a crude oil) through the membranes described herein.

In various aspects, a hydrocarbon feedstream (e.g., a crude oil) comprising a contaminant (e.g., microcarbon residue) is filtered through a membrane described herein to produce a permeate product stream with a lower content of the contaminant (e.g., microcarbon residue) than in the hydrocarbon feedstream (e.g., a crude oil). Additionally or alternatively, a contaminant (e.g., microcarbon residue) wt. % content of a permeate product stream may be less than about 5%, less than about 10%, less than about 20%, less than about 30%, less than about 40%, less than about 50%, less than about 60%, less than about 70%, less than about 80%, less than about 90%, or less than about 95% of the contaminant (e.g., microcarbon residue) wt. % content of the hydrocarbon feedstream (e.g. crude oil). Additionally or alternatively, a contaminant (e.g., microcarbon residue) wt. % content of a permeate product stream may be less than about 5% to about 95%, less than about 10% to about 90%, or less than about 10% to about 50% of the contaminant (e.g., microcarbon residue) wt. % content of the hydrocarbon feedstream (e.g. crude oil).

Additionally or alternatively, the membranes described herein may have a membrane flux of at least about 0.1 gallons/ft²/day (GFD), at least about 0.5 GFD, at least about 1 GFD, at least about 5 GFD, at least about 10 GFD, at least about 20 GFD, at least about 30 GFD, at least about 40 GFD, at least about 50 GFD, at least about 60 GFD, or at least about 70 GFD. Additionally or alternatively, the membranes described herein may have a membrane flux of about 0.1 GFD to about 70 GFD, about 0.1 GFD to about 60 GFD, about 0.1 GFD to about 50 GFD, about 0.1 GFD to about 40 GFD, about 0.1 GFD to about 30 GFD, about 0.1 GFD to about 20 GFD, about 0.1 GFD to about 10 GFD, about 0.1 GFD to about 5 GFD, about 0.1 GFD to about 1 GFD, about 0.5 GFD to about 70 GFD, about 0.5 GFD to about 60 GFD, about 0.5 GFD to about 50 GFD, about 0.5 GFD to about 40 GFD, about 0.5 GFD to about 30 GFD, about 0.5 GFD to about 20 GFD, about 0.5 GFD to about 10 GFD, about 0.5 GFD to about 5 GFD, about 0.5 GFD to about 1 GFD, about 1 GFD to about 70 GFD, about 1 GFD to about 60 GFD, about 1 GFD to about 50 GFD, about 1 GFD to about 40 GFD, about 1 GFD to about 30 GFD, about 1 GFD to about 20 GFD, about 1 GFD to about 10 GFD, or about 1 GFD to about 5 GFD. In particular, the membranes described herein may have a membrane flux of about 0.5 GFD to about 50 GFD (0.85-85 liters/m²/hr (LMH)).

In various aspects, the methods for removing a contaminant (e.g., microcarbon residue) from a hydrocarbon feedstream (e.g. a crude oil) can be performed at temperatures of about 50° C. to about 400°, about 100° C. to about 300° or about 100° C. to about 200° C., and use a pressure differential up to about 1500 psig. For example, the pressure differential can be about 300 psig to about 1500 psig, about 300 psig to about 1200 psig, about 400 psig to about 1000 psig, about 400 psig to about 800 psig, or about 400 psig to about 600 psig.

V. Further Embodiments

The invention can additionally or alternatively include one or more of the following embodiments.

Embodiment 1. A method for fabricating a membrane, the method comprising:
(a) adding at least one compound of Formula $[Z^1Z^2SiCH_2]_3$ (Ia) into an aqueous mixture that contains essentially no structure directing agent or porogen to form a solution, wherein each $Z^1$ represents a hydroxyl group, a $C_1$-$C_4$ alkoxy group or an oxygen bonded to a silicon atom of another compound and each $Z^2$ represents, a hydroxyl group, a $C_1$-$C_4$ alkoxy group, a $C_1$-$C_4$ alkyl group or an oxygen bonded to a silicon atom of another compound;
(b) coating the solution onto a support to form a coated support;
(c) aging the coated support; and
(d) drying the coated support to obtain a membrane comprising an organosilica material which is a polymer comprising independent units of Formula $[Z^3Z^4SiCH_2]_3$ (I), wherein each $Z^3$ represents a hydroxyl group, a $C_1$-$C_4$ alkoxy group or an oxygen atom bonded to a silicon atom of another unit or an active site on the support and each $Z^4$ represents a hydroxyl group, a $C_1$-$C_4$ alkoxy group, a $C_1$-$C_4$ alkyl group, an oxygen atom bonded to a silicon atom of another unit or an active site on the support.

Embodiment 2. The method of embodiment 1, wherein each $Z^1$ represents a $C_1$-$C_2$ alkoxy group.

Embodiment 3. The method of embodiment 1 or 2, wherein each $Z^2$ represents a $C_1$-$C_4$ alkoxy group.

Embodiment 4. The method of any one of the previous embodiments, wherein each $Z^2$ represents a $C_1$-$C_2$ alkoxy group.

Embodiment 5. The method of any one of the previous embodiments, wherein each $Z^3$ represents a hydroxyl group, a $C_1$-$C_2$ alkoxy group, or an oxygen bonded to a silicon atom of another unit or an active site on the support and each $Z^4$ represents a hydroxyl group, a $C_1$-$C_2$ alkyl group, a $C_1$-$C_2$ alkoxy group, or an oxygen bonded to a silicon atom of another unit or an active site on the support.

Embodiment 6. The method of embodiment 5, wherein each $Z^3$ represents a hydroxyl group, ethoxy, or an oxygen bonded to a silicon atom of another unit or an active site on the support and $Z^4$ represents a hydroxyl group, ethoxy, or an oxygen bonded to a silicon atom of another unit or an active site on the support.

Embodiment 7. The method of any one of the previous embodiments, wherein the at least one compound of Formula (Ia) is 1,1,3,3,5,5-hexaethoxy-1,3,5-trisilacyclohexane.

Embodiment 8. The method of any one of the previous embodiments, further comprising adding to the aqueous mixture at least a second compound selected from the group consisting of:
(i) a further compound of Formula (Ia);
(ii) a compound of Formula $R^1OR^2R^3R^4Si$ (II), wherein each $R^1$ represents a $C_1$-$C_4$ alkyl group; and $R^2$, $R^3$, and $R^4$ are each independently selected from the group consisting of a $C_1$-$C_4$ alkyl group, a $C_1$-$C_4$ alkoxy group, a nitrogen-containing $C_1$-$C_{10}$ alkyl group, a nitrogen-containing heteroalkyl group, and a nitrogen-containing optionally substituted heterocycloalkyl group;
(iii) a compound of Formula $Z^5Z^6Z^7Si$—R—$SiZ^5Z^6Z^7$ (III), wherein each $Z^5$ independently represents a $C_1$-$C_4$ alkoxy group; each $Z^6$ and $Z^7$ independently represent a $C_1$-$C_4$ alkoxy group or a $C_1$-$C_4$ alkyl group; and R is selected from the group consisting a $C_1$-$C_8$ alkylene group, a $C_2$-$C_8$ alkenylene group, a $C_2$-$C_8$ alkynylene group, a nitrogen-containing $C_1$-$C_{10}$ alkylene group, an optionally substituted $C_6$-$C_{20}$ aralkyl and an optionally substituted $C_4$-$C_{20}$ heterocycloalkyl group;
(iv) a compound of Formula $M^1(OZ^8)_3$ (IV), wherein $M^1$ represents a Group 13 metal and each $Z^8$ independently represents a $C_1$-$C_6$ alkyl;
(v) a compound of Formula $(Z^9O)_2M^2$—O—$Si(OZ^{10})_3$ (V), wherein $M^2$ represents a Group 13 metal and $Z^9$ and $Z^{10}$ each independently represent a $C_1$-$C_6$ alkyl group;
(vi) a cyclic compound of Formula

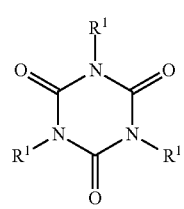

(VI)

wherein each $R^1$ independently is a $X^1OX^2X^3SiX^4$ group, wherein each $X^1$ represents a $C_1$-$C_4$ alkyl group; $X^2$ and $X^3$ each independently represent a $C_1$-$C_4$ alkyl group, a $C_1$-$C_4$ alkoxy group; and $X^4$ represents a $C_1$-$C_8$ alkylene group bonded to a nitrogen atom of the cyclic compound; and
(vii) a combination thereof.

Embodiment 9. The method of embodiment 8, wherein the second compound is a compound of Formula (Ia), wherein each $Z^1$ represents a $C_1$-$C_2$ alkoxy group and each $Z^2$ represents $C_1$-$C_2$ alkoxy group or a $C_1$-$C_2$ alkyl group.

Embodiment 10. The method of embodiment 9, wherein the compound of Formula (Ia) is 1,3,5-trimethyl-1,3,5-triethoxy-1,3,5-trisilacyclohexane.

Embodiment 11. The method of any one of embodiments 8-10, wherein the second compound is a compound of Formula (II), wherein each $R^1$ represents a $C_1$-$C_2$ alkyl group and $R^2$, $R^3$, and $R^4$ are each independently a $C_1$-$C_2$ alkyl group, $C_1$-$C_2$ alkoxy group, a nitrogen-containing $C_3$-$C_{10}$ alkyl group, a nitrogen-containing $C_4$-$C_{10}$ heteroaralkyl group, or a nitrogen-containing optionally substituted $C_4$-$C_{10}$ heterocycloalkyl group.

Embodiment 12. The method of embodiment 11, wherein the compound of Formula (II) is selected from the group consisting of tetraethyl orthosilicate, methyltriethoxysilane, (N,N-dimethyl-aminopropyl)trimethoxysilane, N-(2-aminoethyl)-3-aminopropyltriethoxysilane, 4-methyl-1-(3-triethoxysilylpropyl)-piperazine, 4-(2-(triethoxysily)ethyl)pyridine, 1-(3-(triethoxysilyl)propyl)-4,5-dihydro-1H-imidazole, and (3-aminopropyl)triethoxysilane.

Embodiment 13. The method of any one of embodiments 8-12, wherein the second compound is a compound of Formula (III), wherein $Z^5$ represents a $C_1$-$C_2$ alkoxy group; each $Z^6$ and $Z^7$ independently represent a $C_1$-$C_2$ alkoxy group, or a $C_1$-$C_2$ alkyl group; and R is selected from the group consisting of a $C_1$-$C_4$ alkylene group, a $C_2$-$C_4$ alkenylene group, a $C_2$-$C_4$ alkynylene group, and a nitrogen-containing $C_4$-$C_{10}$ alkylene group.

Embodiment 14. The method of embodiment 13, wherein the compound of Formula (III) is selected from the group consisting of 1,2-bis(methyldiethoxysilyl)ethane, bis(triethoxysilyl)methane, 1,2-bis-(triethoxysilyl)ethylene, N,N'-bis[(3-trimethoxysilyl)propyl]ethylenediamine, bis[(methyl-diethoxysilyl)propyl]amine, and bis[(methyldimethoxysilyl)propyl]-N-methylamine.

Embodiment 15. The method of any one of embodiments 8-14, wherein the second compound is a compound of Formula (IV), wherein $M^1$ is Al or B and each $Z^8$ represents a $C_1$-$C_4$ alkyl group.

Embodiment 16. The method of any one of embodiments 8-15, wherein the second compound is a compound of Formula (V), wherein $M^2$ is Al or B; and $Z^9$ and $Z^{10}$ each independently represent a $C_1$-$C_4$ alkyl group.

Embodiment 17. The method of embodiments 8 or 15, wherein the second compound is selected from the group consisting of aluminum trimethoxide, aluminum triethoxide, aluminum isopropoxide, and aluminum-tri-sec-butoxide.

Embodiment 18. The method of any one of embodiments 8-17, wherein the second compound is a compound of Formula (VI), wherein each $X^1$ represents a $C_1$-$C_2$ alkyl group; $X^2$ and $X^3$ each independently represent a $C_1$-$C_2$ alkyl group or a $C_1$-$C_2$ alkoxy group; and each $X^4$ represents a $C_1$-$C_4$ alkylene group bonded to a nitrogen atom of the cyclic compound.

Embodiment 19. The method of embodiment 18, wherein the compound of Formula (VI) is tris(3-trimethoxysilylpropyl)isocyanurate.

Embodiment 20. The method of any one of the previous embodiments, wherein the aqueous mixture comprises a base and has a pH from about 8 to about 15.

Embodiment 21. The method of embodiment 20, wherein the base is ammonium hydroxide or a metal hydroxide.

Embodiment 22. The method of any one of embodiments 1-19, wherein the aqueous mixture comprises an acid and has a pH from about 0.01 to about 6.0.

Embodiment 23. The method of embodiment 22, wherein the acid is an inorganic acid.

Embodiment 24. The method of embodiment 23, wherein the inorganic acid is hydrochloric acid.

Embodiment 25. The method of any one of the previous embodiments, wherein the coated support is aged for up to 144 hours at a temperature of about room temperature 20° C. to about 200° C.

Embodiment 26. The method of any one of the previous embodiments, wherein the coated support is dried at a temperature of about 15° C. to about 200° C.

Embodiment 27. The method of any one of the previous embodiments, wherein the support is a ceramic support, a polymer support, a mixed-matrix support, a metallic support, a silica support, a carbon support, a liquid/facilitated transport support, a zeolite support, or combinations thereof.

Embodiment 28. The method of any one of the previous embodiments, wherein step (c) comprises aging the coated support in the presence of water.

Embodiment 29. The method of any one of the previous embodiments, wherein the organosilica material has an average pore diameter of about 2.0 nm to about 25.0 nm.

Embodiment 30. The method of any one of the previous embodiments, wherein the organosilica material has a surface area of about 200 m$^2$/g to about 2500 m$^2$/g.

Embodiment 31. The method of any one of the previous embodiments, wherein the organosilica material has a pore volume of 0.1 cm$^3$/g about 3.0 cm$^3$/g.

Embodiment 32. The method of any one of the previous embodiments, wherein the method does not comprise a calcination step.

Embodiment 33. The method of any one of the previous embodiments further comprising adding a $C_1$-$C_6$ alcohol to the solution.

Embodiment 34. The method of embodiment 34, wherein the alcohol is ethanol

Embodiment 35. The method of any one of the previous embodiments, wherein the solution contains about 1 to about 20 wt. % of the compound of Formula (Ia).

Embodiment 36. The method of embodiment 35, wherein the solution contains about 4 to about 6 wt % of the compound of Formula (Ia).

Embodiment 37. The method of any one of the previous embodiments, wherein the membrane is no more than about 1 μm in thickness.

Embodiment 38. A membrane made according to the method of any one of the previous embodiments.

Embodiment 39. A method of removing microcarbon residue from a crude oil, the method comprising filtering a crude oil feedstream through the membrane of embodiment 38.

Embodiment 40. The method of embodiment 39, wherein membrane flux is 0.5 to 50 Gallons/ft$^2$/day (GFD)

Embodiment 41. The method of embodiment 39 or 40, wherein microcarbon residue wt. % content of a permeate product stream is less than about 10% to about 90% of microcarbon residue wt. % content of the crude oil feedstream.

EXAMPLES

The following examples are merely illustrative, and do not limit this disclosure in any way.
The following examples are merely illustrative, and do not limit this disclosure in any way.

General Methods

Nitrogen PorosimetryThe nitrogen adsorption/desorption analyses was performed with different instruments, e.g. TriStar 3000, TriStar II 3020 and Autosorb-1. All the samples were pre-treated at 120° C. in vacuum for 4 hours before collecting the $N_2$ isotherm. The analysis program calculated the experimental data and report BET surface area (total surface area), microporous surface area (SA), total pore volume, pore volume for micropores, average pore diameter (or radius), etc.

Example 1

Synthesis of Mesoporous Organosilica Membranes

FIG. 1 describes the parametric development of template-free mesoporous membranes synthesized from the reagent 1,1,3,3,5,5-Hexaethoxy-1,3,5-Trisilacyclohexane ("reagent 1"). Development of a defect-free membrane was found to be a non-trivial process with identification and careful tuning of various parameters. The first step in membrane development was the preparation of the sol which can be optimized by tuning parameters such as reagent concentration, sol pH and dilution with ethanol. It was found that minor variation in the reagent concentration had an impact on the sol viscosity and eventually on the coating quality. The second step in membrane fabrication involved selection of ceramic supports of appropriate pore size and optimization of the spin coating protocol. An upside-down technique was found to be valid for the mesoporous organosilica (MO) membrane fabrication. Gelation or condensation of MO reagent into cross-linked MO membrane required optimization of temperature, time and environment resulting in a mesoporous, uniformly coated membrane surface. The last step involved controlled drying of the condensed MO membrane to remove residual water, ethanol and catalyst ($NH_4OH$) from the membrane. Drying temperatures, ramp rates and time were optimized to ensure formation of defect-free MO coated discs. Further details regarding membrane synthesis are provided below.

1A. Synthesis of MO Membranes with 1,1,3,3,5,5-Hexaethoxy-1,3,5-Trisilacyclohexane The general procedure for synthesis of MO membranes is provided as follows.

Preparation of MO Sol Solution:

1. An aqueous mixture was made with 6.23 g 30% $NH_4OH$ (0.053 mol $NH_4OH$) and 7.92 g deionized ("DI") water.

2. 1.7 g (0.0043 mol) 1,1,3,3,5,5-Hexaethoxy-1,3,5-Trisilacyclohexane ("reagent 1") was added into the above aqueous mixture, and the solution was stirred for 1 day (20 to 30 hr) at room temperature (20-25° C.) to allow the reagent to hydrolyze creating an MO sol solution.

3. Ethanol was added to the MO sol solution, at 1:1 weight ratio. The MO so solution was stirred at room temperature (20-25° C.) till ready to coat.

Coating of Ceramic Disc:

1. A commercial ceramic ($TiO_2$/$ZrO_2$) disc from TAMI/Sterlitech (300 kD MW cut-off (15 nm pore diameter), 47 mm diameter, 2.5 mm thick) was gas tested with $N_2$ under pressure to ensure disc was free of gross defects (>2-5× pore size).

2. The disc was then mounted on a spin-coater and 1.5 cc of MO sol solution was filtered through a 0.45 μm filter and poured on the disc to uniformly cover the disc surface in an MO coating and an MO coated disc was obtained. The following disc spin coating protocol was used: step a) 500 rpm/30 s (ACL=1), step b) 3000 rpm/2 min (ACL=5), step c) 500 rpm/30 s (ACL=1), step d) stop.

Condensation/gelation and Drying:

1. The MO coated disc was then turned upside-down and mounted in a humidified chamber (glass container partially filled with water).

2. The glass container was then kept in an oven (no vacuum) at 60° C. for 24 hour, with heating rate 5° C./min up to 60° C. to allow MO coating to condense into a uniform coating layer.

3. The disc was then removed from the humidified chamber and dried in an oven at 120° C. for 24 hour with a heating rate of 3° C./min up to 120° C. to obtain an MO membrane on a ceramic disk.

Nitrogen Porosimetry Analysis of MO Membrane

Figures 2A, 2B:
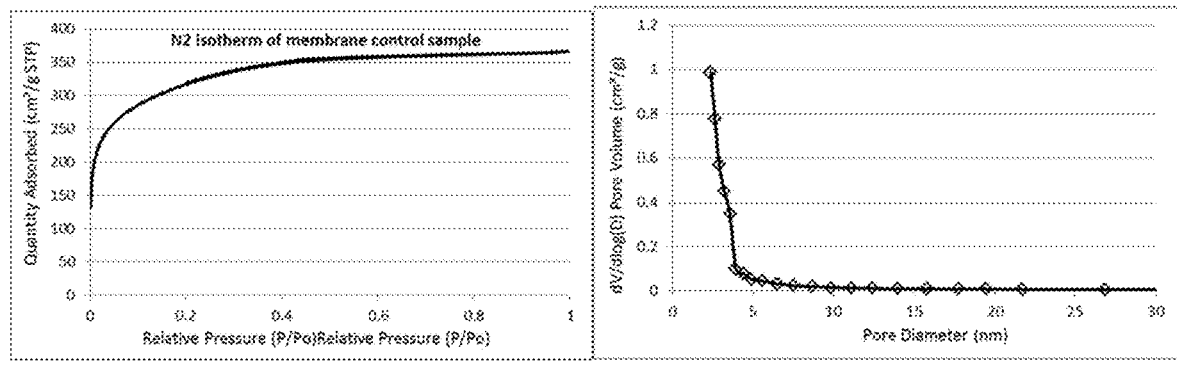
FIG. 2a illustrates $N_2$ adsorption isotherms for a control sample.
FIG. 2b illustrates a BET pore diameter distribution for a control sample.

The surface properties of the MO membrane once coated on a ceramic membrane were difficult to evaluate using $N_2$ physisorption. Hence, a control powder sample ("control sample") utilizing the above protocol without the coating steps 1 and 2 was prepared and evaluated as shown in FIG. 2 and Table 1 below. The control sample indicated an average pore size of around 2 nm with high BET surface area and broad pore size distribution (including both microporous and mesoporous structure).

TABLE 1

| | BET ($m^2/g$) | SA ($m^2/g$, micro) | Pore V (cc/g) | Average diameter (nm) |
|---|---|---|---|---|
| Control Sample | 1132 | 720 | 0.567 | 2 |

Effect of Reagent 1 Concentration on Coating Quality

Figures 3A, 3B, 3C:
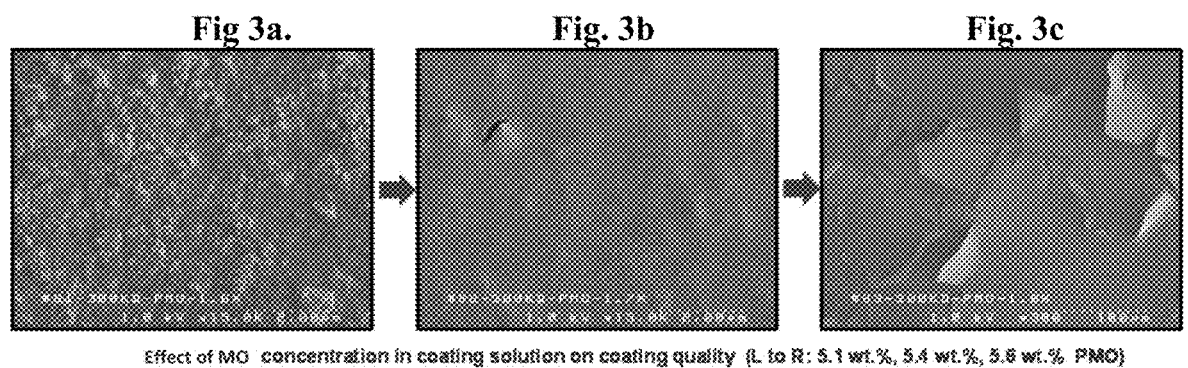
FIG. 3a illustrates a scanning electron microscope (SEM) image of the coating quality of an MO membrane prepared with a 5.1 wt. % 1,1,3,3,5,5-hexaethoxy-1,3,5-trisilacyclohexane.
FIG. 3b illustrates an SEM image of the coating quality of an MO membrane prepared with a 5.4 wt. % 1,1,3,3,5,5-hexaethoxy-1,3,5-Trisilacyclohexane.
FIG. 3c illustrates an SEM image of the coating quality of an MO membrane prepared with a 5.6 wt. % 1,1,3,3,5,5-hexaethoxy-1,3,5-Trisilacyclohexane.

Three MO membranes on 15 nm pore diameter (300 kD) commercial ceramic discs were synthesized with varying concentrations (5.1 wt. %, 5.4 wt. %, 5.6 wt. %) of Reagent 1. FIGS. 3a-3c demonstrate the effect of Reagent 1 concentration on coating quality on a 15 nm pore diameter (300 kD) commercial ceramic disc with 5.1 wt. % reagent concentration leading to partial filling of the pores (FIG. 3a), 5.4 wt. % concentration leading to a uniform, low-defect membrane film (FIG. 3b), while 5.6 wt. % concentration led to a highly defective membrane film (FIG. 3c).

1B. Synthesis of Mesoporous Organosilica Membranes with 1,1,3,3,5,5-Hexaethoxy-1,3,5-Trisilacyclohexane and (3-aminopropyl)triethoxysilane To make the sol solution, the following procedure is used:
  1. A solution with 6.23 g 30% $NH_4OH$ (0.053 mol $NH_4OH$) and 7.92 g DI water was made.
  2. 1,1,3,3,5,5-Hexaethoxy-1,3,5-Trisilacyclohexane and (3-aminopropyl)triethoxysilane (APTES) were added into the above solution at a weight ratio of 4:1 such that the solution had a total reagent wt. % of 3.6.
  3. The solution was stirred for 1 day at room temperature (20-25° C.) to allow the reagent to hydrolyze creating a APTES-MO sol solution.
  4. Ethanol was added to the sol solution, at 1:1 weight ratio. Solution was stirred at room temperature (20-25° C.) till ready to coat.

Figure 5A:
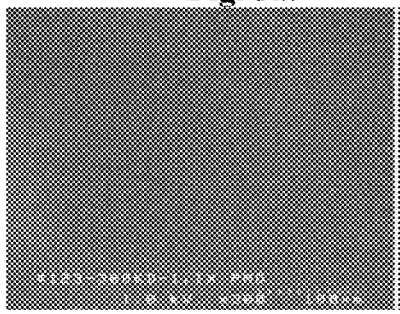
FIGS. 5a-5c illustrate SEM images of different views of a defect-free APTES-MO membrane formed on a 15 nm pore diameter ceramic support.
Figure 5B:
Figure 5C:
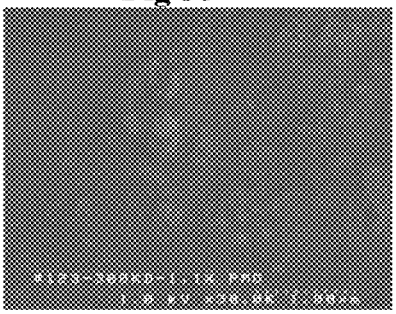

The same coating, condensation and drying procedure used in example 1A were followed to obtain APTES-MO membrane formed on a 15 nm ceramic disc FIGS. 5a-5c shows views of a defect-free APTES-MO membrane formed on a 15 nm pore diameter ceramic support.

Example 2

Effect of Sol pH on Membrane Quality

Example 2A

Synthesis in Basic Solution (pH=8 to 13.4)

Sol pH was found to have an effect on the surface area and pore volume of the MO material as shown in FIGS. 4a and 4b with basic pH providing a highly mesoporous structure. The surface properties of the MO membrane on a ceramic disc were difficult to evaluate using $N_2$ physisorption. Hence, control powder samples at various basic pHs utilizing the protocol detailed below were prepared.

1. Made a $NH_4OH$ solution (about 14 g) with DI water with different pHs (8-14)Added 1 g (2.5 mmol) to 2 g (5 mmol) reagent 1 into the above solution and stirred at 22° C. to 25° C. for 1 day;
2. Added ethanol to the above sol solution with weight ratio of 1:1 (ethanol:sol solution)
3. The MO solution kept in a humidified chamber (glass container partially filled with water).
4. The glass container was then kept in an oven (no vacuum) at 60° C. for 24 hour, with heating rate 5° C./min up to 60° C. to allow the MO solution to condense.
5. The MO solution was then removed from the humidified chamber and dried in an oven at 120° C. for 24 hour with a heating rate of 3° C./min up to 120° C. to obtain the samples.

Example 2B

Synthesis in Acidic Solution (pH=1.04 to 6.2)

Various control powder samples at various acidic pHs utilizing the protocol detailed below were prepared.

1. Make a HCl solution (about 14 g) with DI water with different pHs (0.01 to 6) Added 1 g (2.5 mmol) to 2 g (5 mmol) reagent 1 into the above solution, kept stirring at 22 to 25° C. for 1 day;
2. The MO solution kept in a humidified chamber (glass container partially filled with water).
3. The glass container was then kept in an oven (no vacuum) at 60° C. for 24 hour, with heating rate 5° C./min up to 60° C. to allow the MO solution to condense.
4. The MO solution was then removed from the humidified chamber and dried in an oven at 120° C. for 24 hour with a heating rate of 3° C./min up to 120° C. to obtain the samples.

Example 3

Gas Permeation Testing of Organosilica Membranes

The following gas permeation procedure was followed to test various membranes:

1. The membrane was mounted in a Millipore test cell and pressurized from the membrane coated size with $N_2$ at room temperature (20-25° C.) from 0-30 psig, with the permeate side maintained at atmospheric pressure
2. Gas flux on the permeate side was recorded for different feed pressures
3. Knudsen and viscous flow contributions were determined and compared to bare disc performance to determine coating quality The above procedure was performed for a membrane on ceramic disc (15 nm pore size) prepared according to the procedure in Example 1a ("Membrane 1"), a 2 nm pore diameter ceramic disc ("2 nm ceramic disc"), a 15 nm pore diameter ceramic disc ("15 nm ceramic disc"), an APTES-MO membrane formed on a ceramic disc (15 nm pore size) prepared according to the procedure in Example 1b ("Membrane 2"). All ceramic discs are commercially available and were obtained from the company TAMI.

Figure 6:
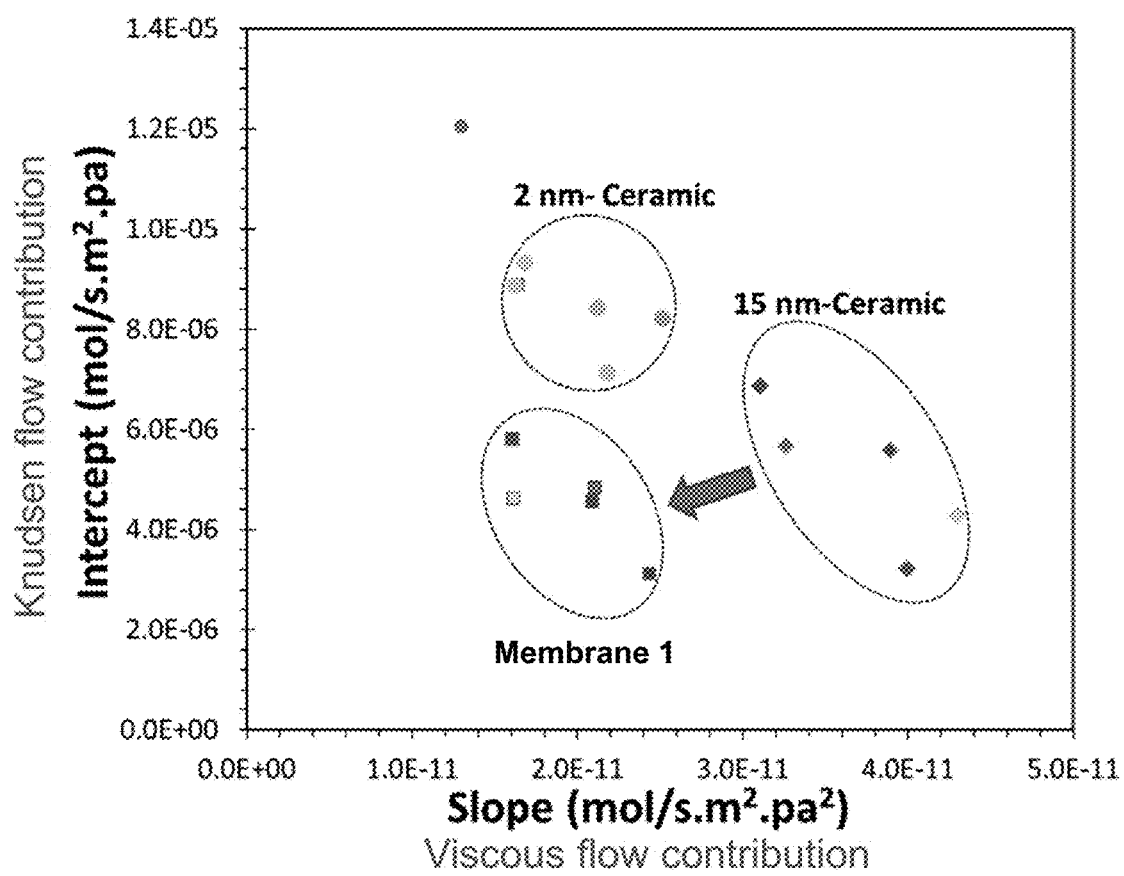
FIG. 6 illustrates gas permeance data comparing the viscous and Knudsen flow contributions of a 2 nm ceramic disc and a 15 nm ceramic disc with Membrane 1 measured using $N_2$ at room temperature (20-25° C.) and variable pressure (0-30 psig).

FIG. 6 shows the gas permeance data comparing the viscous and Knudsen flow contributions of the 2 nm ceramic disc and the 15 nm ceramic disc with Membrane 1 measured using $N_2$ at room temperature (20-25° C.) and variable pressure (0-30 psig). Permeance of the membranes (mol/s·m$^2$·pa) were plotted with respect to the average pressure ($P_{feed}+P_{erm}/2$) (graph not shown) to obtain the intercept and slope for each membrane and then plotted as shown in FIG. 6. Membranes with pores in 2-20 nm range exhibit Knudsen diffusion as the dominating separation mechanism. In Knudsen diffusion, the pore size of the membrane is of the same order as the mean free path of the gas molecule. Membranes with larger pores (>20 nm) exhibit viscous flow. The x-axis of the graph can be related to the viscous flow contribution of the membrane. As the pore size of the membrane is reduced, its viscous flow contribution reduces further as observed when comparing a 2 nm ceramic vs. 15 nm ceramic. It can also be observed that upon MO coating (average pore size≈2 nm) a 15 nm ceramic disc (Membrane 1) behaved similar to a 2 nm ceramic disc confirming that the flow was dominated by the defect-free MO member.

Figure 7:
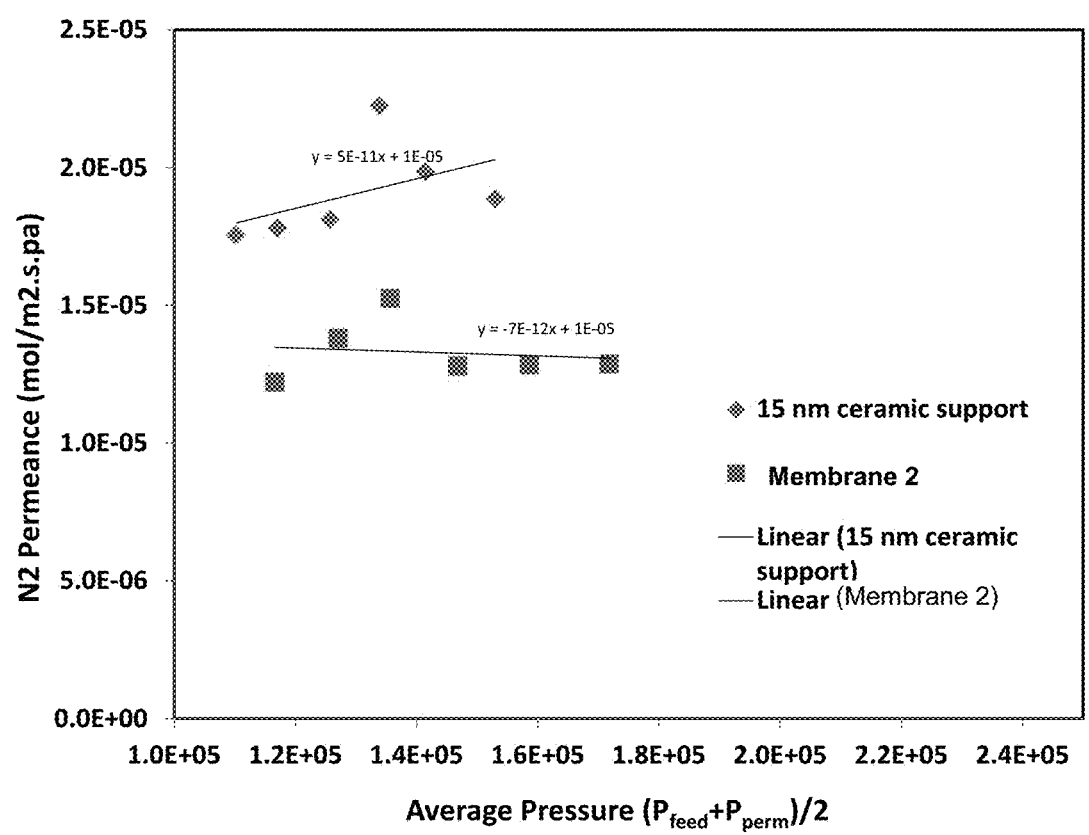
FIG. 7 illustrates gas permeance data comparing a 15 nm ceramic disc with Membrane 2.

FIG. 7 shows gas permeance data comparing a 15 nm ceramic disc with Membrane 2. $N_2$ gas at room temperature and variable pressure (0-30 psig) was used and the permeance of membranes (mol/s·m$^2$·pa) was plotted with respect to the average pressure a ($P_{feed}+P_{erm}/2$). A substantial decrease in slope (viscous flow contribution) can be observed, indicating that larger pores (>20 nm) have been filled with the APTES-MO coating.

Example 4

Crude Oil Separations Testing of Organosilica Membranes

The following crude oil separations testing procedure procedure was followed to test various membranes:

1. A membrane was mounted in a Sterlitech stirred vessel and 150 g of desalted Arab Light crude was charged into the batch test cell
2. The test cell was heated to desired temperature set point (100-200° C.) and desired trans-membrane pressure (400-600 psi) with atmospheric permeate and at a stirring rate of 400 rpm
3. Permeate was collected till a single stage-cut (permeate wt./feed wt.) of 70% was achieved
4. Permeate and retentate (reject) sample streams were sent for further analysis (MCR, Metals, Asphaltenes)

The above procedure was performed for a membrane on ceramic disc (15 nm pore size) prepared according to the procedure in Example 1a ("Membrane 3"), a 15 nm ceramic disc and a 2 nm ceramic disc at the conditions shown below in Table 2.

TABLE 2

| Membrane Conditions | 15 nm ceramic (TiO$_2$) disc | | | 2 nm ceramic (TiO$_2$) disc | | | Membrane 3 | | |
|---|---|---|---|---|---|---|---|---|---|
| | MCR Perm | % Reject | Run (hr) | MCR Perm | % Reject | Run (hr) | MCR Perm | % Reject | Run (hr) |
| 100° C./400 psi | 1.65 | 64 | 13 | 0.9 | 80 | 318 | 0.93 | 79.8 | 74 |
| 200° C./400 psi | 4.25 | 5.1 | 0.6 | 1.45 | 68.4 | 54 | 1.5 | 67.3 | 5.3 |

The run length and microcarbon residue ("MCR") wt. % in permeate were recorded, with the MCR rejection % by membrane estimated using the formula (MCR Reject %=1−MCR$_{perm}$/MCR$_{feed}$). The experiment varied the viscosity (temperature) and driving force (trans-membrane pressure) which in turn affects the rejection % and run length. Higher temperature and trans-membrane pressure were found to reduce the run length (improve flux) however at the expense of MCR rejection %. The performance of a commercial 15 nm ceramic was more severely affected by the operating parameters with rejection % dropping to 5%. Surprisingly, the Membrane 3 rejection % matched the performance of a 2 nm ceramic membrane, with a 4-10× reduction in run length (or ≈4-10× improvement in flux). During the prolonged study under harsh chemical (whole crude), thermal (up to 200° C.), and mechanical (ΔP=600 psi) conditions Membrane performance was found to be stable indicating its applicability as a platform for gas/hydrocarbon separations.

Example 5

Hydrothermal Stability Testing of Organosilica Membranes

Figure 8:
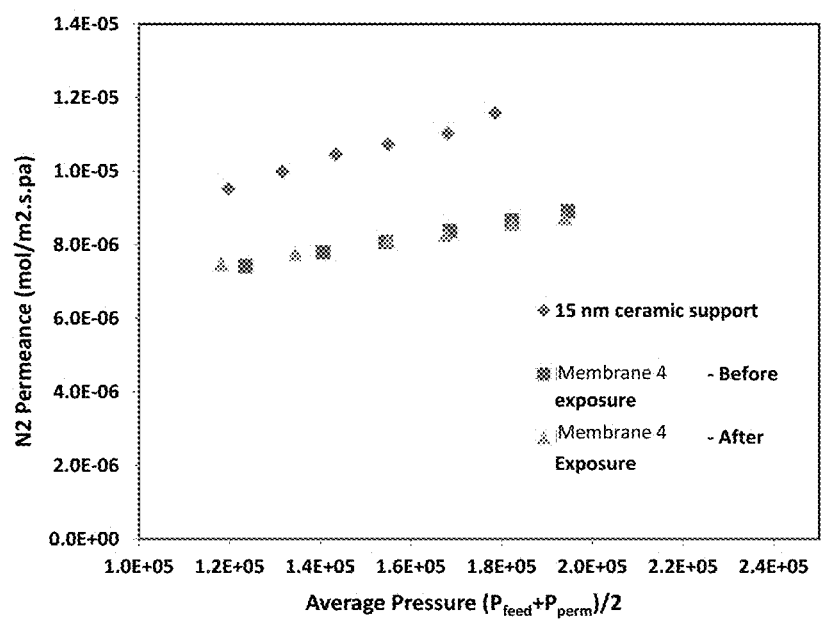
FIG. 8 illustrates the gas permeance data comparing a 15 nm ceramic discs with Membrane 4 before and after hydrothermal exposure.

Defect-free MO coated membranes prepared according to the procedure in example 1 ("Membrane 4") were exposed to 100% humidity at 90° C. for 3 days, followed by drying at 120° C., under vacuum for 24 hours (i.e. hydrothermal exposure). FIG. 8 shows the gas permeance data comparing a commercial 15 nm ceramic disc with Membrane 4 before and after hydrothermal exposure. $N_2$ gas at room temperature (20-25° C.) and variable pressure (0-30 psig) was used and the permeance of membranes (mol/s·m2·pa) was plotted with respect to the average pressure a ($P_{feed}+P_{erm}/2$). Surprisingly, Membrane 4 showed outstanding hydrothermal stability with the gas permeance and slope remaining unaffected before and after hydrothermal treatment. Hydrothermal exposure of conventional microporous silica on the other hand leads to collapse of the porous structure, yielding dense impermeable materials.

What is claimed is:

1. A method for fabricating a membrane, the method comprising:
   (a) adding at least one cyclic compound of Formula [$Z^1Z^2SiCH_2$]$_3$ (Ia) into an aqueous mixture to form a solution, wherein the aqueous mixture and the solution contain essentially no structure directing agent or porogen and wherein the aqueous mixture comprises an acid and has a pH from about 0.01 to about 6.0, each $Z^1$ represents a $C_1$-$C_4$ alkoxy group and each $Z^2$ represents, a $C_1$-$C_4$ alkoxy group or a $C_1$-$C_4$ alkyl group; wherein the solution contains about 5.1 to about 5.4 wt. % of the compound of Formula (Ia) based on the total weight of the solution; adding a $C_1$-$C_4$ alcohol to the solution;
   (b) coating the solution onto a support, wherein the support is a ceramic support, a polymer support, a mixed-matrix support, a metallic support, a silica support, a carbon support, a liquid/facilitated transport support, a zeolite support, or combinations thereof, to form a coated support;
   (c) aging the coated support; and
   (d) drying the coated support to obtain a membrane comprising an organosilica material which is a polymer comprising independent units of Formula [$Z^3Z^4SiCH_2$]$_3$ (I), wherein each $Z^3$ represents a hydroxyl group or an oxygen atom bonded to a silicon atom of another unit or an active site on the support and each $Z^4$ represents a hydroxyl group or an oxygen atom bonded to a silicon atom of another unit or an active site on the support, wherein the organosilica material has an X-ray diffraction spectrum exhibiting substantially no peaks above 6 degrees 2θ.

2. The method of claim 1, wherein each $Z^1$ represents a $C_1$-$C_2$ alkoxy group.

3. The method of claim 2, wherein each $Z^2$ represents a $C_1$-$C_4$ alkoxy group.

4. The method of claim 3, wherein each $Z^2$ represents a $C_1$-$C_2$ alkoxy group.

5. The method of claim 1, wherein the at least one compound of Formula (Ia) is 1,1,3,3,5,5-hexaethoxy-1,3,5-trisilacyclohexane.

6. The method of claim 1, further comprising adding to the aqueous mixture at least a second compound selected from the group consisting of:
   (i) a further compound of Formula (Ia);
   (ii) a compound of Formula $R^1OR^2R^3R^4Si$ (II), wherein each $R^1$ represents a $C_1$-$C_4$ alkyl group; and $R^2$, $R^3$, and $R^4$ are each independently selected from the group consisting of a $C_1$-$C_4$ alkyl group, a $C_1$-$C_4$ alkoxy group, a nitrogen-containing $C_1$-$C_{10}$ alkyl group, a nitrogen-containing heteroalkyl group, and a nitrogen-containing optionally substituted heterocycloalkyl group;
   (iii) a compound of Formula $Z^5Z^6Z^7Si$—R—$SiZ^5Z^6Z^7$ (III), wherein each $Z^5$ independently represents a $C_1$-$C_4$ alkoxy group; each $Z^6$ and $Z^7$ independently represent a $C_1$-$C_4$ alkoxy group or a $C_1C_4$ alkyl group; and R is selected from the group consisting a $C_1$-$C_8$ alkylene group, a $C_2$-$C_8$ alkenylene group, a $C_2$-$C_8$ alkynylene group, a nitrogen-containing $C_1$-$C_{10}$ alkylene group, an optionally substituted $C_6$-$C_{20}$ aralkyl and an optionally substituted $C_4$-$C_{20}$ heterocycloalkyl group;
   (iv) a compound of Formula $M^1(OZ^8)_3$ (IV), wherein $M^1$ represents a Group 13 metal and each $Z^8$ independently represents a $C_1$-$C_6$ alkyl;
   (v) a compound of Formula $(Z^9O)_2M^2$—O—$Si(OZ^{10})_3$ (V), wherein $M^2$ represents a Group 13 metal and $Z^9$ and $Z^{10}$ each independently represent a $C_1$-$C_6$ alkyl group;
   (vi) a cyclic compound of Formula

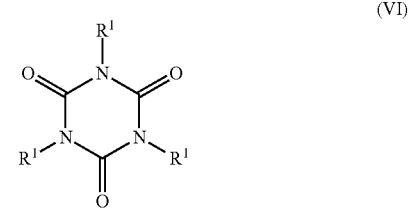

(VI)

wherein each $R^1$ independently is a $X^1OX^2X^3SiX^4$ group, wherein each $X^1$ represents a $C_1$-$C_4$ alkyl group; $X^2$ and $X^3$ each independently represent a $C_1$-$C_4$ alkyl group, a $C_1$-$C_4$ alkoxy group; and $X^4$ represents a $C_1$-$C_8$ alkylene group bonded to a nitrogen atom of the cyclic compound; and
   (vii) a combination thereof.

7. The method of claim 6, wherein the second compound is a compound of Formula (Ia), wherein each $Z^1$ represents a $C_1$-$C_2$ alkoxy group and each $Z^2$ represents $C_1$-$C_2$ alkoxy group or a $C_1$-$C_2$ alkyl group.

8. The method of claim 7, wherein the compound of Formula (Ia) is 1,3,5-trimethyl-1,3,5-triethoxy-1,3,5-trisilacyclohexane.

9. The method of claim 6, wherein the second compound is a compound of Formula (II), wherein each $R^1$ represents a $C_1$-$C_2$ alkyl group and $R^2$, $R^3$, and $R^4$ are each independently a $C_1$-$C_2$ alkyl group, $C_1$-$C_2$ alkoxy group, a nitrogen-containing $C_3$-$C_{10}$ alkyl group, a nitrogen-containing $C_4$-$C_{10}$ heteroaralkyl group, or a nitrogen-containing optionally substituted $C_4$-$C_{10}$ heterocycloalkyl group.

10. The method of claim 9, wherein the compound of Formula (II) is selected from the group consisting of tetraethyl orthosilicate, methyltriethoxysilane, (N,N-dimethylaminopropyl)trimethoxysilane, N-(2-aminoethyl)-3-aminopropyltriethoxysilane, 4-methyl-1-(3-triethoxysilylpropyl)-piperazine, 4-(2-(triethoxysily)ethyl)pyridine, 1-(3-(triethoxysilyl)propyl)-4,5-dihydro-1H-imidazole, and (3-aminopropyl)triethoxysilane.

11. The method of claim 6, wherein the second compound is a compound of Formula (III), wherein $Z^5$ represents a $C_1$-$C_2$ alkoxy group; each $Z^6$ and $Z^7$ independently represent a $C_1$-$C_2$ alkoxy group, or a $C_1$-$C_2$ alkyl group; and R is selected from the group consisting of a $C_1$-$C_4$ alkylene group, a $C_2$-$C_4$ alkenylene group, a $C_2$-$C_4$ alkynylene group, and a nitrogen-containing $C_4$-$C_{10}$ alkylene group.

12. The method of claim 11, wherein the compound of Formula (III) is selected from the group consisting of 1,2-bis(methyldiethoxysilyl)ethane, bis(triethoxysilyl)methane, 1,2-bis-(triethoxysilyl)ethylene, N,N'-bis [(3-trimethoxysilyl)propyl]ethylenediamine, bis[(methyl-diethoxysilyl)propyl]amine, and bis[(methyldimethoxysilyl)propyl]-N-methylamine.

13. The method of claim 6, wherein the second compound is a compound of Formula (IV), wherein $M^1$ is Al or B and each $Z^8$ represents a $C_1$-$C_4$ alkyl group.

14. The method of claim 6, wherein the second compound is a compound of Formula (V), wherein $M^2$ is Al or B; and $Z^9$ and $Z^{10}$ each independently represent a $C_1$-$C_4$ alkyl group.

15. The method of claim 13, wherein the second compound is selected from the group consisting of aluminum trimethoxide, aluminum triethoxide, aluminum isopropoxide, and aluminum-tri-sec-butoxide.

16. The method of claim 6, wherein the second compound is a compound of Formula (VI), wherein each $X^1$ represents a $C_1$-$C_2$ alkyl group; $X^2$ and $X^3$ each independently represent a $C_1$-$C_2$ alkyl group or a $C_1$-$C_2$ alkoxy group; and each $X^4$ represents a $C_1$-$C_4$ alkylene group bonded to a nitrogen atom of the cyclic compound.

17. The method of claim 16, wherein the compound of Formula (VI) is tris(3-trimethoxysilylpropyl)isocyanurate.

18. The method of claim 1, wherein the aqueous mixture comprises a base and has a pH from about 8 to about 15.

19. The method of claim 18, wherein the base is ammonium hydroxide or a metal hydroxide.

20. The method of claim 1, wherein the acid is an inorganic acid.

21. The method of claim 1, wherein the inorganic acid is hydrochloric acid.

22. The method of claim 1, wherein the coated support is aged for up to 144 hours at a temperature of about room temperature 20° C. to about 200° C.

23. The method of claim 1, wherein the coated support is dried at a temperature of about 15° C. to about 200° C.

24. The method of claim 1, wherein step (c) comprises aging the coated support in the presence of water.

25. The method of claim 1, wherein the organosilica material has an average pore diameter of about 2.0 nm to about 25.0 nm.

26. The method of claim 1, wherein the organosilica material has a surface area of about 200 $m^2$/g to about 2500 $m^2$/g.

27. The method of claim 1, wherein the organosilica material has a pore volume of 0.1 $cm^3$/g to about 3.0 $cm^3$/g.

28. The method of claim 1, wherein the method does not comprise a calcination step.

29. The method of claim 1, wherein the alcohol is ethanol.

30. The method of claim 1, wherein the membrane is no more than about 1 μm in thickness.

31. A membrane made according to the method of claim 1.

32. A method of removing microcarbon residue from a crude oil, the method comprising filtering a crude oil through the membrane of claim 31.

33. The method of claim 32, wherein membrane flux is 0.5 to 50 Gallons/$ft^2$/day (GFD).

34. The method of claim 32, wherein microcarbon residue wt. % content of a permeate product stream is less than about 10% to about 90% of microcarbon residue wt. % content of a hydrocarbon feed stream.

* * * * *